United States Patent
Beight et al.

(10) Patent No.: US 7,365,066 B2
(45) Date of Patent: Apr. 29, 2008

(54) PYRAZOLOPYRIDINE DERIVATIVES AS PHARMACEUTICAL AGENTS

(75) Inventors: Douglas Wade Beight, Frankfort, IN (US); Rosanne Bonjouklian, Zionsville, IN (US); Junkai Liao, Tewksbury, MA (US); William Thomas McMillen, Indianapolis, IN (US); Brandon Lee Parkhurst, Twin Rivers, NJ (US); Jason Scott Sawyer, Indianapolis, IN (US); Jonathan Michael Yingling, Fishers, IN (US); Jeremy Schulenburg York, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 451 days.

(21) Appl. No.: 10/524,577

(22) PCT Filed: Sep. 16, 2003

(86) PCT No.: PCT/US03/26297

§ 371 (c)(1), (2), (4) Date: Feb. 15, 2005

(87) PCT Pub. No.: WO2004/026871

PCT Pub. Date: Apr. 1, 2004

(65) Prior Publication Data

US 2005/0222197 A1    Oct. 6, 2005

Related U.S. Application Data

(60) Provisional application No. 60/411,560, filed on Sep. 17, 2002.

(51) Int. Cl.
- A61K 31/535 (2006.01)
- A61K 31/50 (2006.01)
- A01N 43/42 (2006.01)
- C07D 471/02 (2006.01)
- C07D 413/00 (2006.01)

(52) U.S. Cl. .............................. 514/231.2; 514/234.5; 514/252.01; 514/300; 546/121; 544/111; 544/253

(58) Field of Classification Search ................ 546/121; 544/111, 253; 514/300, 231.2, 252.01, 234.5
See application file for complete search history.

(56) References Cited

FOREIGN PATENT DOCUMENTS

| JP | 2001139575 | * | 5/2001 |
|----|------------|---|--------|
| WO | WO 02 062787 |  | 8/2002 |
| WO | WO 02 062794 |  | 8/2002 |
| WO | WO 02 066462 |  | 8/2002 |
| WO | WO 02 094833 |  | 11/2002 |

OTHER PUBLICATIONS

Dermer (Bio/Technology, 1994, 12:320).*
Freshney (Culture of Animal Cells, A Manual of Basic Technique, Alan R. Liss, Inc., 1983, New York, pp. 1-6).*

* cited by examiner

Primary Examiner—Margaret D. Seaman
Assistant Examiner—Niloofar Rahmani
(74) Attorney, Agent, or Firm—Tina M. Tucker; Danica L. Hostettler

(57) ABSTRACT

Novel pyrazolopyridine derivative compounds are disclosed and their use as pharmaceutical agents, in particular their use as TGF-beta signal transduction inhibitors useful in the treatment of cancer and other disease states influenced by TGF beta.

2 Claims, No Drawings

PYRAZOLOPYRIDINE DERIVATIVES AS PHARMACEUTICAL AGENTS

This is the national phase application, under 35 USC 371, for PCT/US2003/026297, filed 16 Sep. 2003, which claims the benefit, under 35 USC 119(e), of U.S. provisional application 60/411,560, filed 17 Sep. 2002.

The invention relates to new pyrazolopyridine derivative compounds and their use as pharmaceutical agents, in particular their use as TGF-beta signal transduction inhibitors.

BACKGROUND OF THE INVENTION

The transforming growth factor-beta (TGF-Beta)("TGF-$\beta$") polypeptides influence growth, differentiation, and gene expression in many cell types. The first polypeptide of this family that was characterized, TGF-$\beta$1, has two identical 112 amino acid subunits that are covalently linked. TGF-$\beta$1 is a highly conserved protein with only a single amino acid difference distinguishing humans from mice. There are two other members of the TGF-$\beta$ gene family that are expressed in mammals. TGF-$\beta$2 is 71% homologous to TGF-$\beta$1 (de Martin, et al. (1987) EMBO J. 6:3673-3677), whereas TGF-$\beta$3 is 80% homologous to TGF-$\beta$1 (Derynck, et al. (1988) EMBO J 7:3737-3743). The structural characteristics of TGF-$\beta$1 as determined by nuclear magnetic resonance (Archer, et al. (1993) Biochemistry 32:1164-1171) agree with the crystal structure of TGF-$\beta$2 (Daopin, et al. (1992) Science 257:369-374; Schlunegger and Grutter (1992) Nature 358:430-434).

There are at least three different extracellular TGF-$\beta$ receptors, Type I, II and III that are involved in the biological functions of TGF-$\beta$1, -$\beta$2 and -$\beta$3 (For reviews, see Derynck (1994) TIBS 19:548-553 and Massague (1990) Ann. Rev. Cell Biol. 6:597-641).

The Type I and Type II receptors are transmembrane serine/threonine kinases which in the presence of TGF-$\beta$ form a heteromeric signaling complex (Wrana, et al (1992) Cell 71: 1003-1014). The mechanism of activation of the heteromeric signaling complex at the cell surface has been elucidated (Wrana, et al. (1994) Nature 370: 341-347). TGF-$\beta$ first binds the type II receptor which is a constitutively active transmembrane serine/threonine kinase. The type I receptor is subsequently recruited into the complex, phosphorylated at the GS domain and activated to phosphorylate downstream signaling components (e.g. Smad proteins) to initiate the intracellular signaling cascade. A constitutively active type I receptor (T204D mutant) has been shown to effectively transduce TGF-$\beta$ responses, thus bypassing the requirement for TGF-$\beta$ and the type II receptor (Wieser, et al. (1995) EMBO J 14: 2199-2208). Although no signaling function has been discovered for the type III receptor, it does increase TGF-$\beta$2's affinity for the type II receptor making it essentially equipotent with TGF-$\beta$1 and TGF-$\beta$3 (Lopez-Casillas, et al. (1993) Cell 73: 1435-1444).

Vascular endothelial cells lack the Type III receptor. Instead endothelial cells express a structurally related protein called endoglin (Cheifetz, et al. (1992) J. Biol. Chem. 267:19027-19030), which only binds TGF-$\beta$1 and TGF-$\beta$3 with high affinity. Thus, the relative potency of the TGF-$\beta$'s reflect the type of receptors expressed in a cell and organ system. In addition to the regulation of the components in the multi-factorial signaling pathway, the distribution of the synthesis of TGF-$\beta$ polypeptides also affects physiological function. The distribution of TGF-$\beta$2 and TGF-$\beta$3 is more limited (Derynck, et al. (1988) EMBO J 7:3737-3743) than TGF-$\beta$1, e.g., TGF-$\beta$3 is limited to tissues of mesenchymal origin, whereas TGF-$\beta$1 is present in both tissues of mesenchymal and epithelial origin.

TGF-$\beta$1 is a multifunctional cytokine critical for tissue repair. High concentrations of TGF-$\beta$1 are delivered to the site of injury by platelet granules (Assoian and Sporn (1986) J. Cell Biol. 102:1217-1223). TGF-$\beta$1 initiates a series of events that promote healing including chemotaxis of cells such as leukocytes, monocytes and fibroblasts, and regulation of growth factors and cytokines involved in angiogenesis, cell division associated with tissue repair and inflammatory responses. TGF-$\beta$1 also stimulates the synthesis of extracellular matrix components (Roberts, et al. (1986) Proc. Natl. Acad. Sci. USA 83:4167-4171; Sporn, et al. (1983) Science 219:1329-1330; Massague (1987) Cell 49:437-438) and most importantly for understanding the pathophysiology of TGF-$\beta$1, TGF-$\beta$1 autoregulates its own synthesis (Kim, et al. (1989) J. Biol. Chem. 264:7041-7045).

A number of diseases have been associated with TGF-$\beta$1 over production. Fibrotic diseases associated with TGF-$\beta$1 overproduction can be divided into chronic conditions such as fibrosis of the kidney, lung and liver and more acute conditions such as dermal scarring and restenosis. Synthesis and secretion of TGF-$\beta$1 by tumor cells can also lead to immune suppression such as seen in patients with aggressive brain or breast tumors (Arteaga, et al. (1993) J. Clin. Invest. 92:2569-2576). The course of Leishmanial infection in mice is drastically altered by TGF-$\beta$1 (Barral-Netto, et al. (1992) Science 257:545-547). TGF-$\beta$1 exacerbated the disease, whereas TGF-$\beta$1 antibodies halted the progression of the disease in genetically susceptible mice. Genetically resistant mice became susceptible to Leishmanial infection upon administration of TGF-$\beta$1.

The profound effects of TGF-$\beta$1 on extracellular matrix deposition have been reviewed (Rocco and Ziyadeh (1991) in Contemporary Issues in Nephrology v. 23, Hormones, autocoids and the kidney. ed. Jay Stein, Churchill Livingston, New York pp. 391-410; Roberts, et al. (1988) Rec. Prog. Hormone Res. 44:157-197) and include the stimulation of the synthesis and the inhibition of degradation of extracellular matrix components. Since the structure and filtration properties of the glomerulus are largely determined by the extracellular matrix composition of the mesangium and glomerular membrane, it is not surprising that TGF-$\beta$1 has profound effects on the kidney. The Accumulation of Mesangial Matrix in Proliferate Glomerulonephritis (Border, et al. (1990) Kidney Int. 37:689-695) and diabetic nephropathy (Mauer, et al. (1984) J. Clin. Invest. 74:1143-1155) are clear and dominant pathological features of the diseases. TGF-$\beta$1 levels are elevated in human diabetic glomerulosclerosis (advanced neuropathy) (Yamamoto, et al. (1993) Proc. Natl. Acad. Sci. 90:1814-1818). TGF-$\beta$1 is an important mediator in the genesis of renal fibrosis in a number of animal models (Phan, et al. (1990) Kidney Int. 37:426; Okuda, et al. (1990) J. Clin. Invest. 86:453). Suppression of experimentally induced glomerulonephritis in rats has been demonstrated by antiserum against TGF-$\beta$1 (Border, et al. (1990) Nature 346:371) and by an extracellular matrix protein, decorin, which can bind TGF-$\beta$1 (Border, et al. (1992) Nature 360:361-363).

Too much TGF-$\beta$1 leads to dermal scar-tissue formation. Neutralizing TGF-$\beta$1 antibodies injected into the margins of healing wounds in rats have been shown to inhibit scarring without interfering with the rate of wound healing or the tensile strength of the wound (Shah, et al. (1992) Lancet 339:213-214). At the same time there was reduced angiogenesis, reduced number of macrophages and monocytes in the wound, and a reduced amount of disorganized collagen fiber deposition in the scar tissue.

TGF-β1 may be a factor in the progressive thickening of the arterial wall which results from the proliferation of smooth muscle cells and deposition of extracellular matrix in the artery afterballoon angioplasty. The diameter of the restenosed artery may be reduced 90% by this thickening, and since most of the reduction in diameter is due to extracellular matrix rather than smooth muscle cell bodies, it may be possible to open these vessels to 50% simply by reducing extensive extracellular matrix deposition. In uninjured pig arteries transfected in vivo with a TGF-β1 gene, TGF-β1 gene expression was associated with both extracellular matrix synthesis and hyperplasia (Nabel, et al. (1993) Proc. Natl. Acad. Sci. USA 90:10759-10763). The TGF-β1 induced hyperplasia was not as extensive as that induced with PDGF-BB, but the extracellular matrix was more extensive with TGF-β1 transfectants. No extracellular matrix deposition was associated with FGF-1 (a secreted form of FGF) induced hyperplasia in this gene transfer pig model (Nabel (1993) Nature 362:844-846).

There are several types of cancer where TGF-β1 produced by the tumor may be deleterious. MATLyLu rat cancer cells (Steiner and Barrack (1992) Mol. Endocrinol 6:15-25) and MCF-7 human breast cancer cells (Arteaga, et al. (1993) Cell Growth and Differ. 4:193-201) became more tumorigenic and metastatic after transfection with a vector expressing the mouse TGF-β1. In breast cancer, poor prognosis is associated with elevated TGF-β (Dickson, et al. (1987) Proc. Natl. Acad. Sci. USA 84:837-841; Kasid, et al. (1987) Cancer Res. 47:5733-5738; Daly, et al. (1990) J. Cell Biochem. 43:199-211; Barrett-Lee, et al. (1990) Br. J Cancer 61:612-617; King, et al. (1989) J. Steroid Biochem. 34:133-138; Welch, et al. (1990) Proc. Natl. Acad. Sci. USA 87:7678-7682; Walker, et al. (1992) Eur. J. Cancer 238:641-644) and induction of TGF-β1 by tamoxifen treatment (Butta, et al. (1992) Cancer Res. 52:4261-4264) has been associated with failure of tamoxifen treatment for breast cancer (Thompson, et al. (1991) Br. J. Cancer 63:609-614). Anti TGF-β1 antibodies inhibit the growth of MDA-231 human breast cancer cells in athymic mice (Arteaga, et al. (1993) J. Clin. Invest. 92:2569-2576), a treatment which is correlated with an increase in spleen natural killer cell activity. CHO cells transfected with latent TGF-β1 also showed decreased NK activity and increased tumor growth in nude mice (Wallick, et al. (1990) J. Exp. Med. 172:1777-1784). Thus, TGF-β secreted by breast tumors may cause an endocrine immune suppression. High plasma concentrations of TGF-β1 have been shown to indicate poor prognosis for advanced breast cancer patients (Anscher, et al. (1993) N. Engl. J. Med. 328:1592-1598). Patients with high circulating TGF-β before high dose chemotherapy and autologous bone marrow transplantation are at high risk for hepatic veno-occlusive disease (15-50% of all patients with a mortality rate up to 50%) and idiopathic interstitial pneumonitis (40-60% of all patients). The implication of these findings is 1) that elevated plasma levels of TGF-β1 can be used to identify at risk patients and 2) that reduction of TGF-1 could decrease the morbidity and mortality of these common treatments for breast cancer patients.

Many malignant cells secrete transforming growth factor-β (TGF-β), a potent immunosuppressant, suggesting that TGF-β production may represent a significant tumor escape mechanism from host immunosurveillance. Establishment of a leukocyte sub-population with disrupted TGF-β signaling in the tumor-bearing host offers a potential means for immunotherapy of cancer. Down regulation of TGF-β secretion in tumor cells results in restoration of immunogenicity in the host, while T-cell insensitivity to TGF-β results in accelerated differentiation and autoimmunity, elements of which may be required in order to combat self-antigen-expressing tumors in a tolerized host. The rationale, approaches, and potential pitfalls of this strategy will be discussed. Cancer: During the earliest stages of carcinogenesis, TGF-β1 can act as a potent tumor suppressor and may mediate the actions of some chemopreventive agents. However, at some point during the development and progression of malignant neoplasms, tumor cells appear to escape from TGF-β-dependent growth inhibition in parallel with the appearance of bioactive TGF-β in the microenvironment. Thus, the production of TGF-β1 by malignant cells in primary tumors appears to increase with advancing stages of tumor progression. Studies in many of the major epithelial cancers suggest that the increased production of TGF-β by human cancers occurs as a relatively late event during tumor progression. Further, this tumor-associated TGF-β provides the tumor cells with a selective advantage and promotes tumor progression. The effects of TGF-β on cell/cell and cell/stroma interactions result in a greater propensity for invasion and metastasis. Tumor-associated TGF-β may allow tumor cells to escape from immune surveillance since it is a potent inhibitor of the clonal expansion of activated lymphocytes. TGF-β has also been shown to inhibit the production of angiostatin. Cancer therapeutic modalities such as radiation therapy and chemotherapy induce the production of activated TGF-β in the tumor, thereby selecting outgrowth of malignant cells that are resistant to TGF-β growth inhibitory effects. Thus, these anticancer treatments increase the risk and hasten the development of tumors with enhanced growth and invasiveness. In this situation, agents targeting TGF-β1 itself might be a very effective therapeutic strategy. The resistance of tumor cells to TGF-β has been shown to negate much of the cytotoxic effects of radiation therapy and chemotherapy and the treatment-dependent activation of TGF-β in the stroma may even be detrimental as it can make the microenvironment more conducive to tumor progression and contributes to tissue damage leading to fibrosis. The development of a TGF-β1 neutralizing agent is likely to benefit the treatment of progressed cancer alone and in combination with other therapies.

Epithelial and hematopoietic cells have a high turnover and their progenitor cells divide continuously, making them prime targets for genetic and epigenetic changes that lead to cell transformation and tumorigenesis. The consequent changes in cell behavior and responsiveness result not only from genetic alterations such as activation of oncogenes or inactivation of tumor suppressor genes, but also from altered production of, or responsiveness to, stimulatory or inhibitory growth and differentiation factors.

Among these, transforming growth factor beta (TGF-beta) and its signaling effectors act as key determinants of carcinoma cell behavior. The autocrine and paracrine effects of TGF-beta on tumor cells and the tumor micro-environment exert both positive and negative influences on cancer development.

Accordingly, the TGF-beta signaling pathway has been considered as both a tumor suppressor pathway and a promoter of tumor progression and invasion. Derynck, R., Akhurst, R. & Balmain, A., TGF-beta signaling in tumor suppression and cancer progression, Nature Genetics, Vol. 29, October, 2001.

SUMMARY OF THE INVENTION

The invention herein disclosed is directed to compounds of the structure:

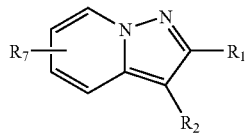

Formula I

Wherein:

R1 is unsubstituted or substituted pyridine; unsubstituted or substituted ffiryl; or unsubstituted or substituted thiophenyl; wherein the substitution may be one or more of the following: (C1-C6)alkyl, (C2-C6)alkenyl, (C1-C6)alkoxy, (C1-C6)alkylthio, trifluoromethyl, halo, N-morpholino, phenylthio;

R2 is unsubstituted or substituted quinoline; unsubstituted or substituted phenyl; unsubstituted or substituted naphthalene; unsubstituted or substituted pyridine; unsubstituted or substituted pyrimidine; unsubstituted or substituted quinazoline; unsubstituted or substituted cinnoline; unsubstituted or substituted indole; unsubstituted or substituted; unsubstituted or substituted benzofuran; unsubstituted or substituted dihydrobenzofuran; unsubstituted or substituted dihydrobenzo[1,4]dioxane; unsubstituted or substituted benzodioxolane; unsubstituted or substituted benzothiophene; unsubstituted or substituted 2-aminobenzimidazole; unsubstituted or substituted imidazo[1,2-a]pyridine; wherein the substitution may independently be one or more of the following: hydrogen, (C1-C6)alkyl, (C2-C6)alkenyl, (C2-C6)alkynyl, (C1-C6) alkylhalide, (C1-C6)alkoxy, (C2-C6) alkenyloxy, (C2-C6)alkynyloxy, (C1-C6)alkylthio, (C1-C6)alkylsulphinyl, (C1-C6)alkylsulphonyl, (C1-C6)alkylamino, di-[(C1-C6)alkyl]amino, (C1-C6)alkoxycarbonyl, N-(C1-C6)alkylcarbamoyl, N,N-di-[(C1-C6)alkyl]carbamoyl, aminooxy, N-(C1-C6)alkyl aminooxy, N,N-di-[(C1-C6)alkyl] aminooxy, (C2-C6)alkanoyl, (C2-C6)alkanoyloxy, (C2-C6)alkanoylamino, N-(C1-C6)alkyl-(C2-C6)alkanoylamino, (C3-C6)alkenoylamino, N-(C1-C6)alkyl-(C3-C6)alkenoylamino, (C3-C6)alkynoylamino, N-(C1-C6)alkyl-(C3-C6)alkynoylamino, sulphamoyl, N-(C1-C6)alkylsulphamoyl, N,N-di-[(C1-C6)alkyl]sulphamoyl, (C1-C6)alkanesulphonylamino, N-(C1-C6)alkyl-(C1-C6)alkanesulphonyl amino, carboxamide, ethylene, phenyl, thiophenyl, aminophenyl, phenylthio, halo, cyano, pyridinyl, arylalkyl, hydroxy, N-pyrrolidino, N-morpholino, carboxyl, [5-phenyl-1,2,4-oxadiazole-3-yl]methoxy, 6-methyl-pyridazin-3-yl-oxy, (5-oxo-2-pyrrolidinyl)methoxy, 2-(4,5-dihydro-1H-imidazolyl), N,N-dialkylcarbamoyloxy, 1-hydroxy-1-methyl-ethyl, 4-fluorophenyl, 3,4-methylenedioxyphenyl, trifluoromethyl, trifluoromethoxy, or a group of the formula:

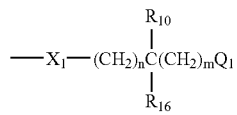

wherein: $X_1$ is O, N, S, $SO_2$, $NR_{13}$, C(O), or bond; $Q_1$ is hydrogen, phenyl, 5-(2,2-difluoro-1,3-benzodioxolyl), C(O)

$Q_5$, or pyridyl when m and n are independently 0-2, except when one is 0 the other cannot be 0; $Q_1$ is $OR_{11}$, $NR_{11}R_{12}$, halo, N-morpholino, N-piperazino-$N'R_{13}$, N-imidazolyl, N-pyrazolyl, N-triazolyl, N-(4-piperidinylpiperidine), $SO_2R_{14}$, $SOR_{14}$, $NHSO_2R_{15}$, acetamido, N-phthalimido, N-oxazolidino, N-imidazolino, N-benzoxazolidino, N-pyrolidinonyl, N(N'-methylbenzimidazolino), N,N-di(C1-C4)alkylamino(C1-C4)alkoxy, N-benzimidazolino; when m and n are independently 0-2, but one or the other of m or n is not 0; $Q_5$ is hydroxy, methoxy, amino, diethylamino, dimethylamino; $R_{10}$ is hydrogen, halo, (C1-C6)alkyl; $R_{11}$ and $R_{12}$ are independently hydrogen, (C1-C6)alkyl, (C1-C6)alkoxy, arylalkyl, (C3-C8)cycloalkyl, (C3-C8)cycloalkylmethyl, 4-(N-methylpiperidinyl), pyridyl, or $R_{11}$ and $R_{10}$ can be taken together to form a 4, 5, 6, or 7 membered ring, or $R_{11}$ and $R_{12}$ can be taken together to form a 3, 4, 5, 6, or 7 membered ring; $R_{13}$ is hydrogen, (C1-C6)alkyl, 2-methoxyphenyl, 2-pyridimidinyl; $R_{14}$ is 2-pyrimidinyl, N-methyl-2-imidazolyl, 4-chlorophenyl, 2-pyridylmethyl; $R_{15}$ is (C1-C6) alkyl, N-methyl-4-imidazolyl; $R_{16}$ is hydrogen, halo, arylalkyl, aryl, or a group of the formula:

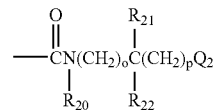

wherein: $Q_2$ is hydrogen, 4-imidazolyl, or $C(O)NR_{24}R_{25}$ when o and p are independently 0-2; $Q_2$ is $OR_{23}$, $NR_{24}R_{25}$, or N-morpholino, when o and p are independently 0-2, but one or the other of o or p is not 0; $R_{20}$ is hydrogen, or (C1-C6)alkyl; $R_{21}$ is hydrogen, (C1-C6)alkyl, or $R_{21}$ and $R_{20}$ can be taken together to form a 4, 5, 6, or 7 membered ring; $R_{22}$ is hydrogen, (C1-C6)alkyl, arylalkyl, aryl, or $R_{21}$ and $R_{22}$ can be taken together to be a 3, 4, 5, 6, 7 membered ring; $R_{23}$ is hydrogen or (C1-C6)alkyl; $R_{24}$ is hydrogen, (C1-C6)alkyl, or $R_{24}$ and $R_{25}$ can be taken together to form a 3, 4, 5, 6, or 7 membered ring, or $R_{24}$ and $R_{20}$ can be taken together to form a 6 or 7 membered ring; $R_{25}$ is hydrogen, (C1-C6)alkyl, or acetyl, or a group of the formula:

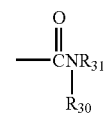

wherein: $R_{30}$ is hydrogen, or (C1-C6)alkyl; $R_{31}$ is hydrogen, (C1-C6)alkyl, 2-pyridyl, pyridylmethyl, amino, or hydroxy, or a group of the formula:

wherein: $R_{32}$ and $R_{33}$ are each independently hydrogen, (C1-C6)alkyl, acetyl, (C1-C4)alkylsulphonyl, or $R_{32}$ and $R_{33}$ can be taken together to form a 4, 5, 6, or 7 membered ring, or a group of the formula:

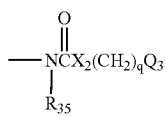

wherein: $X_2$ is $CH_2$, O, or N; q is 2-3 except when $Q_3$ is a bond, q is 0-3; $Q_3$ is $NR_{36}R_{37}$, or $OR_{38}$, and $R_{35}$ is hydrogen, or $R_{35}$ and $Q_3$ can be taken together to form a 5 membered ring; $R_{36}$, $R_{37}$, and $R_{38}$ are each independently hydrogen, or (C1-C6)alkyl, or a group of the formula:

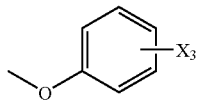

wherein: $X_3$ is cyano, carboxamide, N,N-dimethylcarboxamide, N,N-dimethylthiocarboxamide, N,N-dimethylaminomethyl, 4-methylpiperazin-1yl-methyl or carboxylate, or a group of the formula:

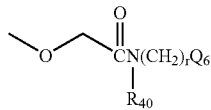

wherein: $Q_6$ is $NR_{41}R_{42}$; r is 2-3; $R_{40}$ is hydrogen, or (C1-C6)alkyl; $R_{41}$ and $R_{42}$ are hydrogen, (C1-C6)alkyl, or $R_{41}$ and $R_{40}$ can be taken together to form a 6 or 7 membered ring, or a group of the formula:

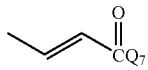

wherein: $Q_7$ is hydroxy, methoxy, dimethylamino, or N-piperidinyl;

and wherein $R_7$ is hydrogen; benzyl; aryl; $C_1$-$C_4$ alkyls; halogen; —$CO_2(C_1$-$C_4$ alkyl); —$CONR_6R_6$; —$C_1$-$C_4$ alcohol; —SO2(C1-C4 alkyl); —$COR_8$;

wherein $R_6$ is (C1-C4alkyl)$R_9$; $R_8$ is (C1-C4alkl) or (C2-C4alkenyl); and $R_9$ is $NR_3R_4$, wherein $R_3$ and $R_4$ are each independently (C1-C4alkyl);

and the pharmaceutically acceptable salts, esters and prodrugs thereof.

The compounds are useful for the treatment of cancer and other disease states influenced by TGF beta, such as fibrosis, atherosclerosis, Alzheimer's disease, wound healing, HIV infection and restenosis, and inflammation, including, but not limited to, for example, arthritis, inflammatory bowel disease, Crohn's disease, irritable bowel syndrome, ulcerative colitis, etc., by inhibiting TGF-β in a patient in need thereof by administering said compound(s) to said patient.

DETAILED DESCRIPTION OF THE INVENTION

The general chemical terms used herein have their usual meanings. For example, as used herein, the term "$C_1$-$C_4$ alkyl", alone or in combination, denotes a straight-chain or branched-chain $C_1$-$C_4$ alkyl group consisting of carbon and hydrogen atoms, examples of which are methyl, ethyl, propyl, isopropyl, butyl, sec-butyl, tert-butyl, and the like. The term "geminal dimethyl" represents two methyl groups attached at the same substitution position. The term "$C_3$-$C_6$ cycloalkyl" refers to cyclopropyl, cyclobutyl, cyclopentyl, and cyclohexyl. The term "spiro-fused $C_3$-$C_6$ cycloalkyl" refers to a $C_3$-$C_6$ cycloalkyl group as defined above bonded to a carbon atom through a spiro linkage.

The term "$C_1$-$C_4$ alkoxy", alone or in combination, denotes an alkyl group as defined earlier, which is attached via an oxygen atom, such as, for example, methoxy, ethoxy, propoxy, isopropoxy, butoxy, tert-butoxy, and the like. The term "$C_1$-$C_4$ alkylthio", alone or in combination, denotes an alkyl group as defined earlier and is attached via a sulfur atom, and includes methylthio, ethylthio, isobutylthio, and the like.

As used herein, the term "halo" or "halogen" represents fluorine, chlorine, bromine, or iodine. The term "hydroxy," alone or in combination, represents an —OH moiety. The term "carboxy" or "carboxyl" refers to a carboxylic acid. The term "carboxamide" refers to a carbonyl substituted with an —$NH_2$ moiety. The term "oxo" refers to a carbonyl group.

As used herein, the term "heteroaryl" means an aryl moiety, which contains 1-5 heteroatoms selected from O, S, and N. Examples of heteroaryl groups include pyrrolyl, pyrazolyl, pyranyl, thiopyranyl, furanyl, imidazolyl, pyridyl, thiazolyl, triazinyl, phthalimidyl, indolyl, purinyl, and benzothiazolyl.

As used herein, the term "aryl" represents a substituted or unsubstituted phenyl or naphthyl. Aryl may be optionally substituted with one or more groups independently selected from hydroxy, carboxy, $C_1$-$C_6$ alkoxy, $C_1$-$C_6$ alkyl, halogen, carboxamide, trifluoromethyl, hydroxymethyl, and hydroxy ($C_1$-$C_4$)alkyl.

The term "$C_3$-$C_8$ cycloalkyl" refers to cyclopropyl, cyclobutyl, cyclopentyl, cyclohexyl, cycloheptyl, and cyclooctyl. The term "optionally substituted $C_3$-$C_8$ cycloalkyl" refers to a $C_3$-$C_8$ cycloalkyl as defined herein unsubstituted or substituted with one or more groups independently selected from hydroxy, carboxy, $C_{1-6}$ alkoxy, $C_{1-6}$ alkyl, halogen, carboxamide, trifluoromethyl, hydroxymethyl, and hydroxy($C_1$-$C_4$)alkyl.

As used herein, the term "saturated heterocycle" is taken to be a 4-9 membered ring containing nitrogen and optionally one other atom selected from oxygen, nitrogen, and sulfur. The term "optionally substituted saturated heterocycle" is taken to be a saturated heterocycle as defined herein unsubstituted or substituted with one or more groups independently selected from hydroxy, carboxy, $C_{1-6}$ alkoxy, $C_{1-6}$ alkyl, halogen, carboxamide, trifluoromethyl, hydroxymethyl, and hydroxy($C_1$-$C_4$)alkyl.

As used herein, the term "$C_1$-$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$-$C_6$ alkyl" includes within its definition the terms "$C_1$-$C_4$ alkyl" and "$C_1$-$C_3$ alkyl."

"$C_1$-$C_6$ alkenyl" refers to a straight or branched, divalent, unsaturated aliphatic chain of 1 to 6 carbon atoms and includes, but is not limited to, methylenyl, ethylenyl, propylenyl, isopropylenyl, butylenyl, isobutylenyl, t-butylenyl, pentylenyl, isopentylenyl, hexylenyl.

"$C_1$-$C_6$ alkoxycarbonyl" represents a straight or branched $C_1$-$C_6$ alkoxy chain, as defined above, that is attached via the oxygen atom to a carbonyl moiety. Typical $C_1$-$C_6$ alkoxycarbonyl groups include methoxycarbonyl, ethoxycarbonyl, propoxycarbonyl, isopropoxycarbonyl, butoxycarbonyl, t-butoxycarbonyl and the like.

The term "di($C_1$-$C_6$ alkyl)amino" refers to a group of the formula:

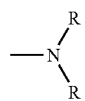

wherein each R group independently represents a "$C_1$-$C_6$ alkyl" group, as defined above.

An "optionally substituted phenyl" is a phenyl ring that is unsubstituted or substituted with 1 to 5 substituents, more preferably 1 to 3 substituents, for example: halo, $C_1$-$C_6$ alkyl, $C_1$-$C_6$ alkoxy, $C_1$-$C_6$ alkylamino, trifluoromethyl, nitro, and cyano.

An "optionally substituted benzyl" is a benzyl ring that is unsubstituted or substituted with 1 to 5 substituents, more preferably 1 to 3 substituents, for example: halo, $C_1$-$C_6$ alkyl, $C_1$-$C_6$ alkoxy, trifluoromethyl, nitro, and cyano.

"Phenoxycarbonyl" refers to the group: phenyl-O—C(O)—. "Aryl" refers to an unsaturated aromatic carbocyclic group of 6 to 14 carbon atoms having a single ring (e.g., phenyl) or multiple condensed (fused) rings (e.g., naphthyl or anthracenyl).

Unless otherwise constrained by the definition for the aryl substituent, such aryl groups can optionally be substituted with 1 to 5 substituents, more preferably 1 to 3 substituents, selected from the group consisting of halo, hydroxy, acetyl, nitro, cyano, $C_1$-$C_6$ alkyl, $C_1$-$C_6$ alkoxy, phenyl, di($C_1$-$C_6$ alkyl)amino, trifluoromethyl, trifluoromethoxy, —S(O)$_m$—($C_1$-$C_6$ alkyl), and —S(O)$_m$-(phenyl), wherein m can be 0, 1, or 2.

"Arylalkyl" refers to aryl groups attached to alkyl groups, preferably having 1 to 6 carbon atoms in the alkyl moiety and 6 to 10 carbon atoms in the aryl moiety. Such arylalkyl groups are exemplified by benzyl, phenethyl, and the like.

Unless otherwise constrained by the definition for arylalkyl, such arylalkyl groups can be optionally substituted with 1 to 5 substituents, more preferably 1 to 3 substituents, selected from the group consisting of halo, hydroxy, nitro, cyano, $C_1$-$C_6$ alkyl, $C_1$-$C_6$ alkoxy, di($C_1$-$C_6$ alkyl)amino, trifluoromethyl, trifluoromethoxy, carbamoyl, pyrrolidinyl, —S(O)$_m$—($C_1$-$C_6$ alkyl), and —S(O)$_m$-(phenyl), wherein m can be 0, 1, or 2. The arylalkyl groups may be optionally substituted on the aryl moiety, the alkyl moiety, or both the aryl moiety and the alkyl moiety.

The term "heterocycle" represents an unsubstituted or substituted 5- to 7-membered monocyclic, or 7- to 11-membered bicyclic heterocyclic ring that is saturated or unsaturated and that consists of carbon atoms and from one to five heteroatoms selected from the group consisting of nitrogen, oxygen or sulfur, and including a bicyclic group in which any of the above-defined heterocyclic rings is fused to a benzene ring to another heterocycle as defined above.

The term "heteroaryls" represents the above-defined heterocylic rings that are fused to a benzene ring to another heterocylce as defined above.

Unless otherwise constrained by the definition for the heterocyclic substituent, such heterocycles can be optionally substituted with 1 to 8 substituents selected from the group consisting of halo, nitro, cyano, hydroxy, acetyl, $C_1$-$C_6$ alkyl, $C_1$-$C_6$ alkoxy, $C_3$-$C_{10}$ cycloalkyl, optionally substituted phenyl, phenethyl, phenoxy, phenoxycarbonyl, optionally substituted benzyl, 1,1-diphenylmethyl, oxo, $C_1$-$C_6$ alkoxycarbonyl, ($C_1$-$C_6$ alkoxy)$C_1$-$C_6$ alkyl-, trifluoromethyl, pyridyl, (pyrrolidinyl)$C_1$-$C_6$ alkyl-, and (pyridyl)$C_1$-$C_6$ alkyl-, di($C_1$-$C_6$ alkyl)amino, trifluoromethyl, trifluoromethoxy, —S(O)$_m$—($C_1$-$C_6$ alkyl), and —S(O)$_m$-(phenyl), wherein m can be 0, 1, or 2.

Examples of such heterocycles include azepinyl, azetidinyl, benzazepinyl, benzimidazolyl, benzoazolyl, benzodioxolyl, benzodioxanyl, benzopyranyl, benzothiazolyl, benzothienyl, dihydropyrazolooxazinyl, dihydropyrazolooxazolyl, furyl, imidazolyl, imidazolinyl, imidazolidinyl, indolinyl, indolyl, isoindolinyl, isoquinolinyl, isothiazolidinyl, isothiazolyl, isoxazolidinyl, isoxazolyl, morpholinyl, napthyridinyl, oxadiazolyl, oxazolyl, oxazolidinyl, phthalimidyl, piperazinyl, piperidinyl, pyrazinyl, pyridyl, pyrazinyl, pyrazolidinyl, pyrazolinyl, pyrazolyl, pyridyl, pyrimidinyl, pyridazinyl, pyrrolidinyl, pyrrolopyrazolyl, pyrrolyl, quinazolinyl, quinolinyl, quinuclidinyl, tetrahydrofuryl, tetrahydropyranyl, tetrahydroisoquinolinyl, tetrahydroquinolinyl, thiazolyl, thiazolinyl, thiazolidinyl, thiadiazolyl, thienyl, thiomorpholinyl, triazolyl, and the like.

Preferred heterocycles include: benzodioxolyl, dihydropyrrolopyrazolyl, pyridyl, quinolinyl.

The preceding paragraphs may be combined to define additional preferred classes of compounds.

The compounds of Formula I are useful for the treatment of disorders of mammals, and the preferred mammal is a human.

The skilled artisan will appreciate that the introduction of certain substituents will create asymmetry in the compounds of Formula I. The present invention contemplates all enantiomers and mixtures of enantiomers, including racemates. It is preferred that the compounds of the invention containing chiral centers are single enantiomers. The present invention further contemplates all diastereomers.

COMPOUNDS EXEMPLIFIED IN THE APPLICATION INCLUDE THE FOLLOWING

4-[2-(6-Ethyl-pyridin-2-yl)-pyrazolo[1,5-a]pyridin-3-yl]-quinoline,

[2-(6-Methyl-pyridin-2-yl)-pyrazolo[1,5-a]pyridin-3-yl]-quinoline-7-carboxylic acid methyl ester, 4-[2-(6-Methyl-pyridin-2-yl)-pyrazolo[1,5-a]pyridin-3-yl]-quinoline-6-carboxylic acid methyl ester, 4-(5-Benzyl-2-pyridin-2-yl-pyrazolo[1,5-a]pyridin-3-yl)-quinoline-7-carboxylic acid methyl ester, 3-(4-Fluoro-phenyl)-2-(6-methyl-pyridin-2-yl)-pyrazolo[1,5-a]pyridine-6-carboxylic acid (2-dimethylamino-ethyl)-amide, 4-[2-(6-Methyl-pyridin-2-yl)-pyrazolo[1,5-a]pyridin-3-yl]-quinoline-6-carboxylic acid (2-dimethylamino-ethyl)-amide, 4-[2-(6-Methyl-pyridin-2-yl)-pyrazolo[1,5-a]pyridin-3-yl]-quinoline-7-carboxylic acid (2-dimethylamino-ethyl)-amide, 5-[2-(6-Methyl-pyridin-2-yl)-pyrazolo[1,5-a]pyridin-3-yl]-benzofuran-2-carboxylic acid (2-dimethyl amino-ethyl)-amide, 4-[2-(6-Methyl-pyridin-2-yl)-pyrazolo[1,5-a]pyridin-3-yl]-quinoline-7-carboxylic acid[3-(4-methyl-piperazin-1-yl)-propyl]-amide, 4-[2-(6-Methoxy-pyridin-2-yl)-pyrazolo[1,5-a]pyridin-3-yl]-quinoline, 4-[2-(6-Ethoxy-pyridin-2-yl)-pyrazolo[1,5-a]pyridin-3-yl]-quinoline, 3-(4-Fluoro-phenyl)-2-(6-methoxy-pyridin-2-yl)-pyrazolo[1,5-a]pyridine, 2-(6-Ethoxy-pyridin-2-yl)-3-(4-fluoro-phenyl)-pyrazolo[1,5-a]pyridine, 7-Benzyl-4-[2-(6-methyl-pyridin-2-yl)-pyrazolo[1,5-a]pyridin-3-yl]-quinoline, 3-{4-[2-(6-Methyl-pyridin-2-yl)-pyrazolo[1,5-a]pyridin-3-yl]-quinolin-7-yl}-acrylic acid methyl ester, 3-{4-[2-(6-Methyl-pyridin-2-yl)-pyrazolo[1,5-a]pyridin-3-yl]-quinolin-7-yl}-acrylic acid, 4-[2-(6-Ethylsulfanyl-pyridin-2-yl)-pyrazolo[1,5-a]-pyridin-3-yl]-quinoline, 4-[2-(6-Phenylsulfanyl-pyridin-2-yl)-pyrazolo[1,5-a]pyridin-3-yl]-quinoline, 4-[2-(6-Morpholin-4-yl-pyridin-2-yl)-pyrazolo[1,5-a]pyridin-3-yl]-quinoline, 3-(4-Fluoro-phenyl)-2-(6-methylsulfanyl-pyridin-2-yl)-pyrazolo[1,5-a]pyridine, 3-(4-Methylsulfanyl-phenyl)-2-(6-methylsulfanyl-pyridin-2-yl)-pyrazolo[1,5-a]pyridine, Dimethyl-(2-{4-[2-(6-methyl-pyridin-2-yl)-pyrazolo[1,5-a]pyridin-3-yl]-quinolin-7-ylsulfanyl}-ethyl)-amine, 2-(Pyridin-2-yl)-3-(quinolin-4-yl)-pyrazolo[1,5-a]pyridine-5-carboxylic acid dimethylamide, 2-(Pyridin-2-yl)-3-(quinolin-4-yl)-pyrazolo[1,5-a]pyridine-6-carboxylic acid dimethylamide, 4-[2-(6-Vinyl-pyridin-2-yl)-pyrazolo[1,5-a]pyridin-3-yl]-quinoline, 6-[2-(6-Methyl-pyridin-2-yl)-pyrazolo[1,5-a]pyridin-3-yl]-imidazo[1,2-a]pyridin-2-yl-amine, 6-[2-(6-Methyl-pyridin-2-yl)-pyrazolo[1,5-a]pyridin-3-yl]-1H-benzoimidazol-2-yl-amine,

[3-(4-Fluoro-phenyl)-2-(6-methyl-pyridin-2-yl)-pyrazolo[1,5-a]pyridin-6-yl]-methanol, 6-Allyloxymethyl-3-(4-fluoro-phenyl)-2-(6-methyl-pyridin-2-yl)-pyrazolo[1,5-a]pyridine, 4-[2-(6-Methyl-pyridin-2-yl)-pyrazolo[1,5-a]pyridin-3-yl]-quinoline-7-carboxylic acid (3-pyrrolidin-1-yl-propyl)-amide, 3-{4-[2-(6-Methyl-pyridin-2-yl)-pyrazolo[1,5-a]pyridin-3-yl]-quinolin-7-yl}-propionamide, 3-{4-[2-(6-Methyl-pyridin-2-yl)-pyrazolo[1,5-a]pyridin-3-yl]-quinolin-7-yl}-N-(3-pyrrolidin-1-yl-propyl)-propionamide, N-(2-Dimethylamino-ethyl)-3-{4-[2-(6-methyl-pyridin-2-yl)-pyrazolo[1,5-a]pyridin-3-yl]-quinolin-7-yl}-propionamide, 2-Pyridin-2-yl-3-quinolin-4-yl-pyrazolo[1,5-a]pyridine-5-carboxylic acid (3-dimethylamino-propyl)-amide, 4-[2-(6-Methyl-pyridin-2-yl)-pyrazolo[1,5-a]pyridin-3-yl]-quinoline-7-carboxylic acid (2-hydroxy-ethyl)-amide, 4-[2-(6-Methyl-pyridin-2-yl)-pyrazolo[1,5-a]pyridin-3-yl]-quinoline-7-carboxylic acid hydrazide, 4-[2-(6-Methyl-pyridin-2-yl)-pyrazolo[1,5-a]pyridin-3-yl]-quinoline-7-carboxylic acid (3-hydroxy-propyl)-amide, 4-[2-(6-Methyl-pyridin-2-yl)-pyrazolo[1,5-a]pyridin-3-yl]-quinoline-7-carboxylic acid methylamide, 4-[2-(6-Methyl-pyridin-2-yl)-pyrazolo[1,5-a]pyridin-3-yl]-quinoline-7-carboxylic acid (3-ethoxy-propyl)-amide, 4-[2-(6-Methyl-pyridin-2-yl)-pyrazolo[1,5-a]pyridin-3-yl]-quinoline-7-carboxylic acid (3-morpholin-4-yl-propyl)-amide, 4-[2-(6-Methyl-pyridin-2-yl)-pyrazolo[1,5-a]pyridin-3-yl]-quinoline-7-carboxylic acid (3-imidazol-1-yl-propyl)-amide, 4-[2-(6-Methyl-pyridin-2-yl)-pyrazolo[1,5-a]pyridin-3-yl]-quinoline-7-carboxylic acid (3-dimethylamino-propyl)-amide, 4-[2-(6-Methyl-pyridin-2-yl)-pyrazolo[1,5-a]pyridin-3-yl]-quinoline-7-carboxylic acid[2-(2-methoxy-phenyl)-ethyl]-amide, 4-[2-(6-Methyl-pyridin-2-yl)-pyrazolo[1,5-a]pyridin-3-yl]-quinoline-7-carboxylic acid (2-morpholin-4-yl-ethyl)-amide, 4-[2-(6-Methyl-pyridin-2-yl)-pyrazolo[1,5-a]pyridin-3-yl]-quinoline-7-carboxylic acid amide, Dimethyl-(3-{4-[2-(6-methyl-pyridin-2-yl)-pyrazolo[1,5-a]pyridin-3-yl]-quinolin-7-yloxy}-propyl)-amine, 4-[2-(6-Methyl-pyridin-2-yl)-pyrazolo[1,5-a]pyridin-3-yl]-7-(2-morpholin-4-yl-ethoxy)-quinoline, Diisopropyl-(2-{4-[2-(6-methyl-pyridin-2-yl)-pyrazolo[1,5-a]pyridin-3-yl]-quinolin-7-yloxy}-ethyl)-amine, 4-[2-(6-Methyl-pyridin-2-yl)-pyrazolo[1,5-a]pyridin-3-yl]-7-(2-pyrrol-1-yl-ethoxy)-quinoline, Dimethyl-(1-methyl-2-{4-[2-(6-methyl-pyridin-2-yl)-pyrazolo[1,5-a]pyridin-3-yl]-quinolin-7-yloxy}ethyl)-amine, Methyl-(3-{4-[2-(6-methyl-pyridin-2-yl)-pyrazolo[1,5-a]pyridin-3-yl]-quinolin-7-yl-oxy}-propyl)-amine, 4-[2-(6-Methyl-pyridin-2-yl)-pyrazolo[1,5-a]pyridin-3-yl]-7-(2-piperidin-1-yl-ethoxy)-quinoline, Diethyl-(2-{4-[2-(6-methyl-pyridin-2-yl)-pyrazolo[1,5-a]pyridin-3-yl]-quinolin-7-yloxy}-ethyl)-amine, Dimethyl-{3-[4-(2-pyridin-2-yl-pyrazolo[1,5-a]pyridin-3-yl)-quinolin-7-yloxy]-propyl}-amine, 7-(2-Morpholin-4-yl-ethoxy)-4-(2-pyridin-2-yl-pyrazolo[1,5-a]pyridin-3-yl)-quinoline, Diisopropyl-{2-[4-(2-pyridin-2-yl-pyrazolo[1,5-a]pyridin-3-yl)-quinolin-7-yloxy]-ethyl}-amine, 4-[2-(6-Methyl-pyridin-2-yl)-pyrazolo[1,5-a]pyridin-3-yl]-7-(3-morpholin-4-yl-propoxy)-quinoline, 1-(3-{4-[2-(6-Methyl-pyridin-2-yl)-pyrazolo[1,5-a]pyridine-3-yl]-quinolin-7-yloxy}-propyl)-1,3-dihydro-benzoimidazol-2-one 3-{4-[2-(6-Methyl-pyridin-2-yl)-pyrazolo[1,5-a]pyridin-3-yl]-quinolin-7-yl}-propionic acid methyl ester, Diethyl-{3-[4-(2-pyridin-2-yl-pyrazolo[1,5-a]pyridin-3-yl)-quinolin-7-yloxy]-propyl}-amine, Ethyl-methyl-{3-[4-(2-pyridin-2-yl-pyrazolo[1,5-a]pyridin-3-yl)-quinolin-7-yloxy]-propyl}-amine, 4-(2-Pyridin-2-yl-pyrazolo[1,5-a]pyridin-3-yl)-7-(3-pyrrolidin-1-yl-propoxy)-quinoline, 7-(3-Piperidin-1-yl-propoxy)-4-(2-pyridin-2-yl-pyrazolo[1,5-a]pyridin-3-yl)-quinoline, Diethyl-{2-[4-(2-pyridin-2-yl-pyrazolo[1,5-a]pyridin-3-yl)-quinolin-7-yloxy]-ethyl}-amine, Dimethyl-{2-[4-(2-pyridin-2-yl-pyrazolo[1,5-a]pyridin-3-yl)-quinolin-7-yloxy]-ethyl}-amine, and the pharmaceutically acceptable salts, esters and prodrugs thereof.

The compounds exemplified above are merely representative of the invention and are not limiting in any fashion.

The compounds of the present invention can be prepared by a variety of procedures, some of which are illustrated in the Schemes below. It will be recognized by one of skill in the art that the individual steps in the following schemes may be varied to provide the compounds of Formula I. Some of these variations are discussed below.

The particular order of steps required to produce the compounds of Formula I is dependent upon the particular compound being synthesized, the starting compound, and the relative lability of the substituted moieties. Some substituents have been eliminated in the following schemes for the sake of clarity, and are not intended to limit the teaching of the schemes in any way.

SCHEME I

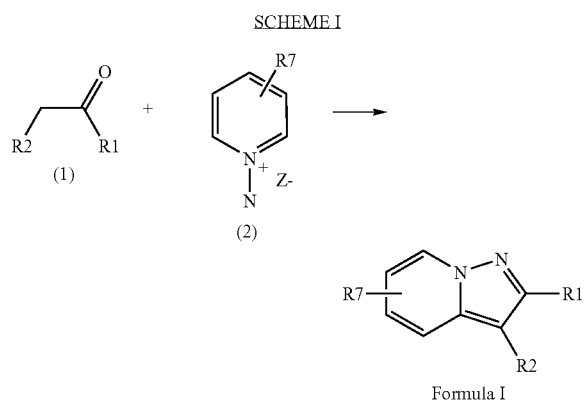

Formula I

Scheme I, depicts a cyclization of optionally substituted 1-amino-pyridinium salts of formula (2), and optionally substituted ethanones of formula (1) in the formation of Formula I. Cyclization reaction of the optionally substituted ethanones of formula (1) with the 1-amino-pyridinium salt, in which the counter-anion, Z, can be a halogen or a trialkyl-benzenesulfonate, are generally done with an organic base, such as triethylamine, DBU, or preferably diisopropylethylamine, in a suitable solvent such as ethanol under elevated temperatures. The product of Formula I can be isolated and purified by techniques well known in the art, such as precipitation, filtration, extraction, evaporation, trituration, chromatography, and recrystallization.

SCHEME II

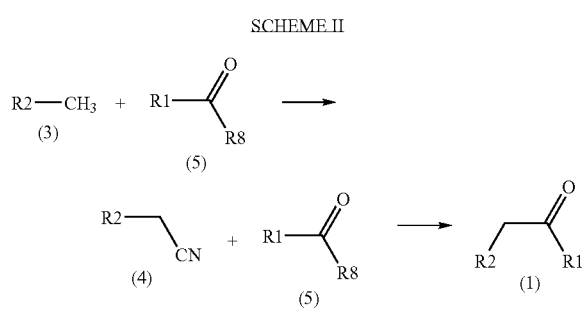

Scheme II depicts an acylation of an appropriate aromatic and/or heteroaromatic compound of formula (3) and an appropriate carbonyl compound of formula (5) to give a compound of formula (1). The aromatic and/or heteroaromatic compounds of formula (3) are commercially available or can be produced by methods known in the art. The acylation of formula (3) requires that R8, of formula (5), be a suitable leaving group, such as C1-C6 alkoxy, disubstituted amino, halo, C1-C6 thioether, preferably disubstituted amino. The reaction is typically carried out in the presence of a suitable base that can create an anion of the compound of formula (3), such as lithium diisopropylamide, potassium bis(trimethylsilyl)amide, lithium bis(trimethylsilyl)amide, sodium bis(trimethylsilyl)amide, sodium hydride, lithium hydride, potassium hydride, sodium alkoxides (sodium methoxide, or sodium ethoxide) or potassium alkoxides (potassium methoxide, or potassium ethoxide), with potassium bis(trimethylsilyl)amide being the preferred base. Generally, the reaction is carried out in suitable solvents, such as tetrahydrofuran and toluene or a combination of such, at temperatures of about −78° C. to ambient temperature. The product, formula (1), can be isolated and purified by techniques well known in the art, such as precipitation, filtration, extraction, evaporation, trituration, chromatography, and recrystallization. Another variation of the acylation is to use a nitrile compound of formula (4) in place of the aromatic- or heteroaromatic-methyl compounds of formula (3). The intermediate, cyanoketone, can be transformed to formula (1) by hydrolysis of the nitrile group and then subsequent decarboxylation. Generally, the cyanoketone is dissolved in a hydrogen halide acid solution, preferably hydrogen chloride. The reaction is carried out at temperatures of about ambient to refluxing for about 24 hours. This type of reaction is well known and appreciated in the art (Larock, R. C., *Comprehensive Organic Transformations*, copyright 1989, VCH, pp 993). Compounds of formula (4) can be acquired by treatment of an appropriate substituted aromatic- or heteroaromatic-methyl group with a halogenating reagent, such as N-halosuccinimides, preferably N-bromosuccinimide in carbon tetrachloride and subsequently reacting the aromatic-halomethylene intermediate with a nitrile source, such as lithium cyanide, potassium cyanide, or trimethylsilyl cyanide, preferably sodium cyanide. The reaction is carried out at ambient temperatures for about 24 hours to afford the acetonitrile compounds of formula (4), (Larock, R. C., *Comprehensive Organic Transformations*, copyright 1989, VCH, pp 313; Eur. J. Org. Chem. 1999, 2315-2321).

SCHEME III

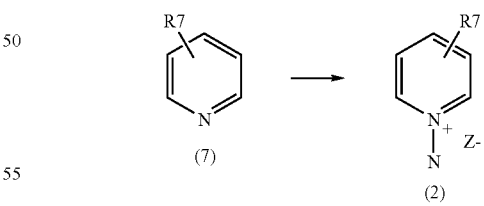

In Scheme I, optionally substituted 1-amino-pyridium salts of formula (2) are employed in the formation of Formula I. These salts are either commercially available or may be prepared by generally combining the appropriate substituted pyridine of formula (7) with a trialkyl-benzenesulfononylhydroxylamine preferably O-(2,4,6-trimethylbenzenesulfonyl)-hydroxylamine in a suitable solvent such as diciforomethane. These salts can be isolated and purified by precipitation with a nonpolar solvent such as hexanes.

SCHEME IV

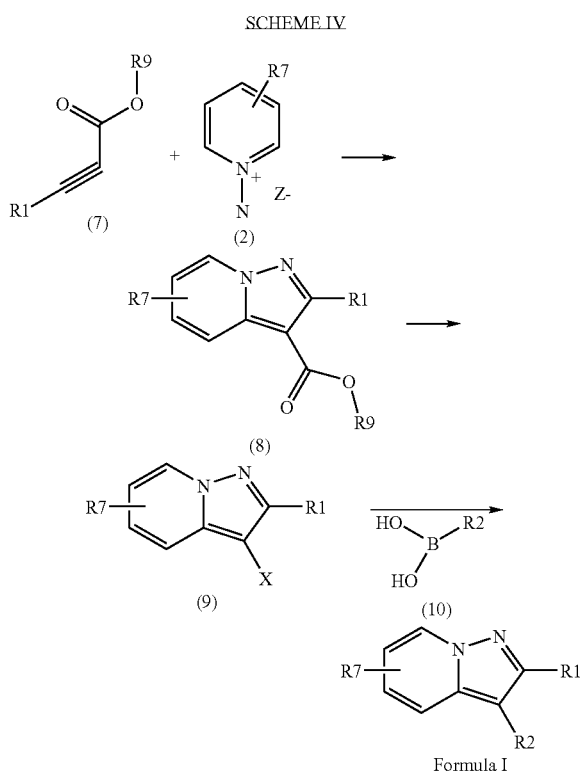

To further elaborate substitution for compounds of Formula I at the R2 functionality, Scheme IV can be followed. Scheme IV depicts the formation of the pyrazolopyridine nucleus by cyclization of an appropriate substituted propynoic carboxyl-ester, followed by a typical hydrolysis of the ester (Larock, R. C., Comprehensive Organic Transformations, $2^{nd}$ Ed., copyright 1999, John Wiley & Sons, pp 1959-1968) to the carboxylic acid, and a halodecarboxylation Reference to give formula (9), where X is a halogen. The cyclization procedure is similar to the one previously described in Scheme I, with the exception that the preferable base is DBU and the solvent should be acetonitrile. With a halogen at the C3 position of the pyrazolopyridine ring a coupling reaction with a boronic acid derivative of formula (10) can be conducted. This type of coupling reaction is well known in the art (Larock, R. C., Comprehensive Organic Transformations, $2^{nd}$ Ed., copyright 1999, John Wiley & Sons, pp 104-107).

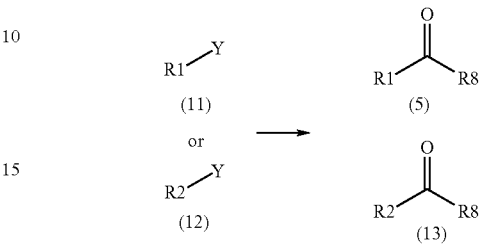

Scheme V, depicts a carbonylation reaction for the formation of compounds of formula (5) and (13), where R8 is a suitable leaving group such as C1-C6 alkoxy, disubstituted amino, halo, C1-C6 thioether, preferably C1-C6 alkoxy. Compounds of formula (11) and (12) are used in the formation of formula (5) and (13), respectively. The carbonyl group of formula (5) and (13) can further undergo a synthetic transformation to interconvert between the leaving groups R8, where R8 is previously described. The Y group can be an aromatic or heteroaromatic halide and the reaction can be carried out in the presence of carbon monoxide, a suitable nucleophile, such as an amine or an alcohol, with a palladium (0) or palladium (II) catalyst, such as 1,1'-bis (diphenylphosphino) ferrocene]dichloropalladium(II): dichloromethane, tetrakis(triphenylphosphine)-palladium (0), bis(triphenylphosphine)palladium (II) chloride or palladium(II) acetate, tetrakis(triphenylphosphine)palladium(0), tris-(benzylideneacetone)dipalladium(0), palladium dichloride, palladium bis(trifluoroacetate), or preferably 1,1'-bis (diphenylphosphino) ferrocene]dichloropalladium(II): dichloromethane. All reagents of the reagents are combined in a suitable solvent, typically terahydrofuran, toluene or ethylene glycol dimethyl ether, stirred at temperatures of about 0 to 80° C. All products can be isolated and purified by techniques described above.

SCHEME VI

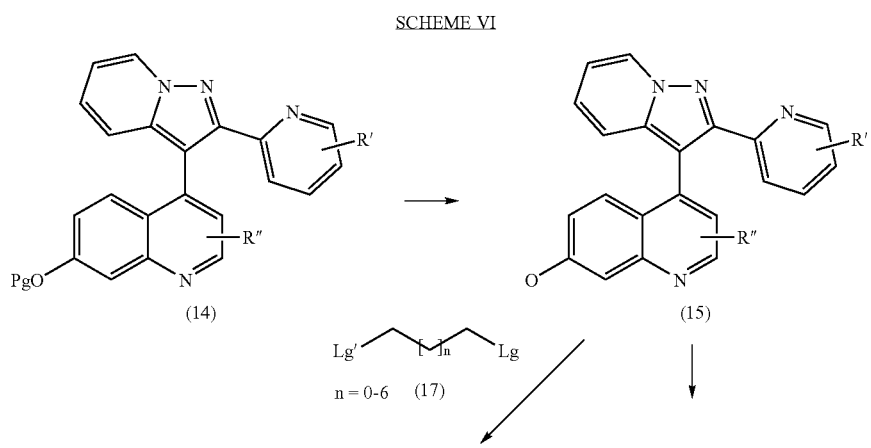

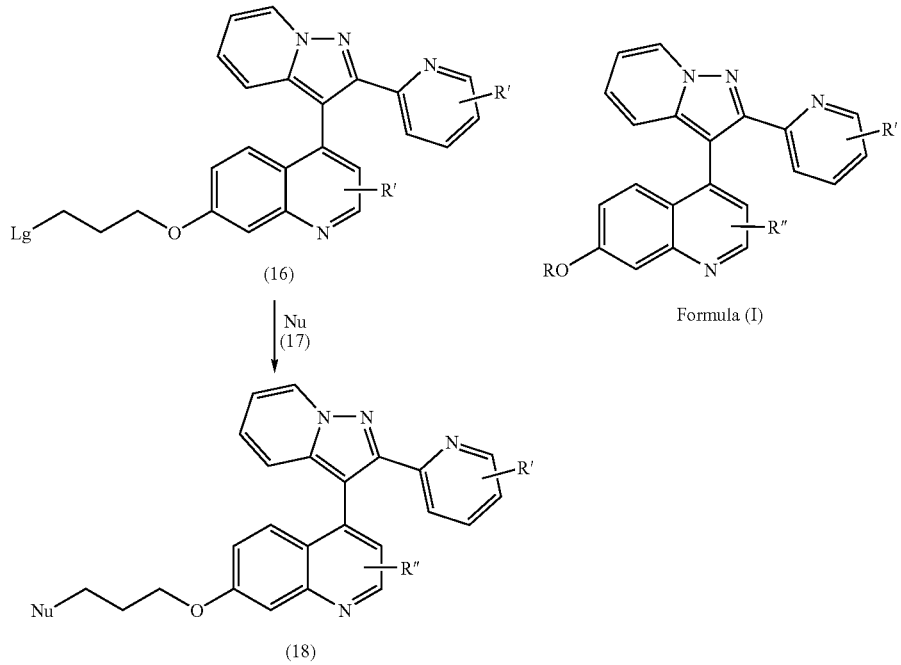

Scheme VI depicts the manipulation of hydroxy-aryl compounds of formula (15) for further alkylations and transformations to enable the scope of this invention, where the R group(s) are previously described. Representative conversions are shown in Scheme VI.

Scheme VI, depicts the deprotection of a protected aromatic-hydroxy group of formula (14) to give a compound of formula (15), where the "Pg" can be an alkoxide. The deprotection is well known and appreciated in the art (Greene T. W., Wuts, P. G. M. *Protective Groups in Organic Synthesis*, copyright 1991, John Wiley and Sons, Inc., pp 146-149). The product of formula (15) can be isolated and purified by techniques previously described.

Scheme VI also depicts the transformation of an aryl ether compound of formula (15) to give the compounds of Formula (I). The formation of an aryl ether is well known and appreciated in the art (March, J., *Advanced Organic Chemistry*, copyright 1985, John Wiley and Sons, Inc., pp 342-343, 589. and Mundy, B. P., Ellerd, M. G. *Name Reactions and Reagents in Organic Synthesis*, copyright 1988, John Wiley and Sons, Inc., pp 242, 530; Sawyer, J. S., Schmittling, E. A., Palkowitz, J. A., Smith, III, W. J., J. Org. Chem., 1998, 63, 6338-6343). The products can be isolated and purified by techniques described above.

Scheme VI furthermore depicts an alkyation of a compound of formula (15) to give a variably substituted compound of formula (16), where the leaving group(s) "Lg" and "Lg'" can include such leaving groups, but are not limited to, halides, oxonium ions, alkyl perchlorates, ammuonioalkanesulfonate esters, alkyl fluorosulfonates, nonaflates, tresylates, triflates, and sulfonic esters, preferably the mesylate or tosylate, given "Lg" and "Lg'" are not the same group. Typically, the appropriate compound of formula (15) is reacted with a suitable base that can form the anion of the phenol, such as lithium carbonate, sodium carbonate, potassium carbonate, cesium carbonate, sodium hydride, lithium hydride, potassium hydride, with cesium carbonate being the preferred base, in the presence of a compound of formula (17). The reaction is carried out in a suitable solvent, such as tetrahydrofuran, dimethylsulfoxide, dimethyl acetamide or toluene, or preferably N,N-dimethylformamide at temperatures of about 0 to 100° C. The products can be isolated and purified by techniques described above.

Finally, Scheme VI, depicts the nucleophilic substitution of leaving group "Lg", by a nucleophile to form a compound of the formula (16). Nucleophilic substitution is well known and appreciated in the art (March, J., *Advanced Organic Chemistry*, copyright 1985, John Wiley and Sons, Inc., pp 255-446). Typically, the compound of formula (16) is reacted with a nucleophile of formula (17), which is typically, but not limited to, primary amines, secondary amines, alcohols or thiols. The reaction is carried out in a suitable solvent, such as tetrahydrofuran, dimethylsulfoxide, dimethyl acetamide or toluene, or preferably N,N-dimethylformamide at temperatures of about 0 to 100° C. The products can be isolated and purified by techniques described above.

A skilled artisan can appreciate several transformations that can be applied to the synthetic process for production of useful and reactive intermediates. Further elaboration can be completed by transformation of the appropriate functional groups, such as transformation of a carboxylester to an amide, halogen alkoxy exchange (Larock, R. C., Comprehensive Organic Transformations, $2^{nd}$ Ed., copyright 1999, John Wiley & Sons, pp 893-894), hydrolysis of a carboxylester (Larock, R. C., Comprehensive Organic Transformations, $2^{nd}$ Ed., copyright 1999, John Wiley & Sons, pp 1959-1968), palladium promoted additions (Larock, R. C., Comprehensive Organic Transformations, $2^{nd}$ Ed., copyright 1999, John Wiley & Sons, pp 1685-1687), O-alkylations (Larock, R. C., Comprehensive Organic Transformations, $2^{nd}$ Ed., copyright 1999, John Wiley & Sons, pp 890-893) and a nucleophilic exchange of aromatic-halogens (Larock, R. C., Comprehensive Organic Transformations, $2^{nd}$ Ed., copyright 1999, John Wiley & Sons, pp 779-780). These types of transformations of functional groups are well known and appreciated in the art.

A skilled artisan would also appreciate that amine containing intermediates can be protected with various protecting groupssuch as a formyl group, acetyl, or preferably a tert-butoxycarbonyl moiety. Techniques for the introduction of these groups are well known to the skilled artisan. The skilled artisan will appreciate that the nitrogen-protecting groups may be removed at any convenient point in the synthesis of the compounds of the present invention. Methods of formation and removal of an amino-protecting group are well known in the art (for example, see: T. W. Greene, "Protective Groups in Organic Synthesis," John Wiley and Sons, New York, N.Y., 1991, Chapter 7).

The skilled artisan would appreciate that appropriate leaving groups for the hydroxy intermediates could include halides, oxonium ions, alkyl perchlorates, ammonio-alkanesulfonate esters, alkyl fluorosulfonates, nonaflates, tresylates, triflates, and sulfonic esters, preferably the mesylate or tosylate. Techniques for the introduction of these groups are well known to the skilled artisan. (See for example: March, "Advanced Organic Chemistry," John Wiley and Sons, New York, N.Y., 1992, pg. 352-362). The hydroxy compound is then dissolved in an appropriate solvent, such as tetrahydrofuran, diethyl ether or N,N-dimethylformamide and is reacted with a strong base, such as potassium hydride or sodium hydride. The reaction is conducted under nitrogen at about 0° C. and stirred for 30-120 minutes. These compounds can be isolated and purified by standard techniques.

Many of the compounds of the present invention are not only inhibitors of TGF-beta, but are also usefull intermediates for the preparation of additional compounds of the present invention. For example, secondary amines may be acylated, alkylated or coupled with simple carboxylic acids or amino acids under standard conditions. Furthermore, ester moieties may be reduced to the corresponding alcohols. These alcohols may then be activated and displaced by a number of nucleophiles to provide other compounds of the invention. The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired. Furthermore, the skilled artisan will appreciate that in many circumstances, the order in which moieties are introduced is not critical.

The following preparations and examples further illustrate the preparation of compounds of the present invention and should not be interpreted in any way as to limit the scope. Those skilled in the art will recognize that various modifications may be made while not departing from the spirit and scope of the invention. All publications mentioned in the specification are indicative of the level of those skilled in the art to which this invention pertains.

The terms and abbreviations used in the instant Preparations and Examples have their normal meanings unless otherwise designated. For example "° C.", "N", "mmol", "g", "mL", "M", "HPLC", "IR", "MS(FD)", "MS(IS)", "MS(FIA)", "MS(FAB)", "MS(EI)", "MS(ES)", "UV", and "$^1$H NMR", refer to degrees Celsius, normal or normality, millimole or millimoles, gram or grams, milliliter or milliliters, molar or molarity, high performance liquid chromatography, infrared spectrometry, field desorption mass spectrometry, ion spray mass spectrometry, flow injection analysis mass spectrometry, fast atom bombardment mass spectrometry, electron impact mass spectrometry, electron spray mass spectrometry, ultraviolet spectrometry, and proton nuclear magnetic resonance spectrometry, respectively. In addition, the absorption maxima listed for the IR spectra are only those of interest and not all of the maxima observed.

PREPARATION 1

2-Ethynyl-6-methyl-pyridine

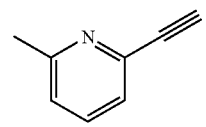

2-Bromo-6-methylpyridine (0.5 g, 2.9 mmol) and trimethylsilylacetylene (0.29 g, 2.9 mmol) in Et$_3$N (15 mL) is purged with argon. Then CuI (11 mg, 0.06 mmol) and (PPh$_3$)$_2$PdCl$_2$ (42 mg, 0.06 mmol) are added and the reaction stirred under argon at room temp for 2 hours. The solvent is removed in vacuo and the residue diluted in EtOAc (50 mL) and water (50 mL). The organic is separated and washed with brine. The solvent is removed to afford a dark oil. This oil is diluted in MeOH (50 mL) and treated with a 1 N NaOH solution (10 mL) and stirred for 3 hours at room temp. The aqueous is then acidified to pH=4 with 1 N HCl and extracted with dichloromethane. The solvent is removed in vacuo to afford 1.16 g (24%) as a light yellow oil used as is in following reactions. $^1$H NMR (CDCl$_3$) δ: 7.54 (t, 1H), 7.29 (d, 1H), 7.12 (d, 1H), 3.12 (s, 1H), 2.55 (s, 1H). MS ES$^+$ m/e 118.1 (M+1).

By method in PREPARATION 1 the following compounds were synthesized:

| PREP # | Product (Chemical Name) | Starting Material A | Starting Material B | Physical Data | Comments |
|---|---|---|---|---|---|
| 2 | 2-Ethynyl-pyridine | 2-Bromopyridine | | MS ES$^+$ m/e 103.9 (M + 1). | |
| 3 | 2-Ethyl-6-ethynyl-pyridine | 2-Bromo-6-ethylpyridine | | MS ES$^+$ m/e 133.0 (M + 1). | |

PREPARATION 4

(6-Methyl-pyridin-2-yl)-propynoic acid ethyl ester

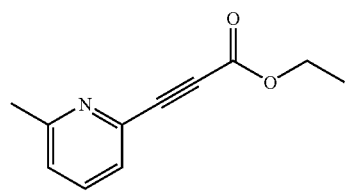

A solution of 2-Ethynyl-6-methyl-pyridine (0.5 g, 4.3 mmol) in THF (20 mL) is cooled to −78° C. and treated with 1.6 M n-butyllithium in hexanes (2.9 mL, 4.7 mmol) and stirred for 0.5 hours. This solution is then treated with ethyl chloroformate (2.85 mL, 30 mmol) and stirred for 3 hours while the solution warms to room temperature The reaction is diluted with saturated aqueous ammonium chloride and extracted with EtOAc. The solvent is concentrated to afford 0.67 g (83%) of desired product as a light yellow oil. UV (95% EtOH) $\lambda_{max}$ 286 nm ($\epsilon$ 10977), 238 nm ($\epsilon$ 9757). TOF MS ES$^+$ exact mass calculated for $C_{11}H_{11}NO_2$ (p+1): M/z=190.0868. Found: 190.0864.

By method in PREPARATION 4 the following compounds were synthesized:

| PREP # | Product (Chemical Name) | Starting Material A | Starting Material B | Physical Data | Comments |
|---|---|---|---|---|---|
| 5 | Pyridin-2-yl-propynoic acid ethyl ester | 2-Ethynyl-pyridine (Prep. 2) | | MS ES$^+$ m/e 176.2 (M + 1). | |
| 6 | (6-Ethyl-pyridin-2-yl)-propynoic acid ethyl ester | 2-Ethyl-6-ethynyl-pyridine (Prep. 3) | | MS ES$^+$ m/e 204.1 (M + 1). | |

PREPARATION 7

2-(6-Methyl-pyridin-2-yl)-pyrazolo[1,5-a]pyridine-3-carboxylic acid ethyl ester

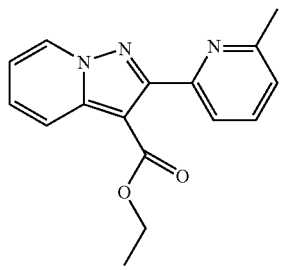

A solution of (6-methyl-pyridin-2-yl)-propynoic acid ethyl ester (0.62 g, 3.3 mmol) and 1-aminopyridinium iodide (0.8 g, 3.6 mmol) in acetonitrile (15 mL) is treated with DBU (0.5 mL, 3.3 mmol) and heated to reflux for 0.5 hours. The reaction is concentrated to a dark solid and purified by silica gel column chromatography (1:1 hexane/ethyl acetate) to afford 0.224 g (24%) of desired product as a yellow solid. MS ES$^+$ m/e 282.2 (M+1). UV (95% EtOH) $\lambda_{max}$ 275 nm ($\epsilon$ 13005), 234 nm ($\epsilon$ 26550), 225 nm ($\epsilon$ 26057). TOF MS ES$^+$ exact mass calculated for $C_{11}H_{11}NO_2$ (p+1): m/z=282.1243. Found: 282.1244. Anal. Calcd for $C_{16}H_{15}N_3O_2$: C, 68.31; H, 5.37; N, 14.94. Found: C, 68.04; H, 5.28; N, 14.65.

| PREP # | Product (Chemical Name) | Starting Material A | Starting Material B | Physical Data | Comments |
|---|---|---|---|---|---|
| 8 | 2-(6-Methyl-pyridin-2-yl)-6-phenyl-pyrazolo[1,5-a]pyridine-3-carboxylic acid ethyl ester (Isomer 1) and 2-(6-Methyl-pyridin-2-yl)-4-phenyl-pyrazolo[1,5-a]pyridine-3-carboxylic acid ethyl ester (Isomer 2) | (6-Methyl-pyridin-2-yl)-propynoic acid ethyl ester (Prep. 4) | 1-Amino-3-phenyl pyridinium | $^1$H NMR of Isomer 1 (CDCl$_3$) δ 8.79(s, 1H), 8.27(d, 1H), 7.73-7.59(m, 5H), 7.53-7.42 (m, 3H), 7.23 (d, 1H), 4.31 (q, 2H), 2.68 (s, 3H), 1.30(t, 3H) and $^1$H NMR of Isomer 2 δ 8.54(d, 1H), 7.74(d, 1H), 7.65(t, 1H), 7.44(m, 5H), 7.16(m, 2H), 6.96(t, 1H), 3.69(q, 2H), 2.57(s, 3H), 0.92(t, 3H) | When treated with 3-substituted aminated pyridine, reaction gave mixture of products with 4 or 6 substitution |
| 9 | 6-Methanesulfonyl-2-(6-methyl-pyridin-2-yl)-pyrazolo[1,5-a]pyridine-3-carboxylic acid ethyl ester and 4-Methanesulfonyl-2-(6-methyl-pyridin-2-yl)-pyrazolo[1,5- | (6-Methyl-pyridin-2-yl)-propynoic acid ethyl ester (Prep. 4) | 1-Amino-3-methanesulfonyl pyridinium iodide | MS ES$^+$ m/e 360.1 (M + 1). | When treated with 3-substituted aminated pyridine, reaction gave mixture of products with 4 or 6 substitution. Mixture could be separated by chromatography |

| PREP # | Product (Chemical Name) | Starting Material A | Starting Material B | Physical Data | Comments |
|---|---|---|---|---|---|
| | a]pyridine-3-carboxylic acid ethyl ester | | | | |
| 10 | 2-Pyridin-2-yl-pyrazolo[1,5-a]pyridine-3-carboxylic acid ethyl ester | Pyridin-2-yl-propynoic acid ethyl ester (Prep. 5) | 1-Aminopyridinium iodide | MS ES+ m/e 268.1 (M + 1). | |
| 11 | 2-(6-Ethyl-pyridin 2-yl)-pyrazolo[1,5-a]pyridine-3-carboxylic acid ethyl ester | (6-Ethyl-pyridin-2-yl)-propynoic acid ethyl ester (Prep. 6) | 1-Aminopyridinium iodide | MS ES+ m/e 296.1 (M + 1). | |

PREPARATION 12

2-(6-Methyl-pyridin-2-yl)-pyrazolo[1,5-a]pyridine-3-carboxylic acid

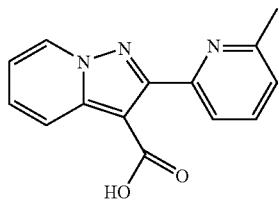

A solution of 2-(6-methyl-pyridin-2-yl)-pyrazolo[1,5-a]pyridine-3-carboxylic acid ethyl ester (0.18 g, 0.6 mmol) in EtOH (10 mL) is treated with a 2N NaOH solution (3 mL) and refluxed for 3 hours. The reaction is concentrated to a yellow solid and diluted with 1N HCl (30 mL). The aqueous is extracted with $CH_2Cl_2$ (3×10 mL) and the organic solution dried over $Na_2SO_4$. The solution is filtered and the solvent removed in vacuo to afford 0.152 g (94%) of desired product as a white solid. MS ES+ m/e 254.1 (M+1). UV (95% EtOH) $\lambda_{max}$ 284 nm ($\epsilon$ 23625), 244 nm ($\epsilon$ 24036). TOF MS ES+ exact mass calculated for $C_{14}H_{11}N_3O_2$ (p+1): m/z=254.0930. Found: 254.0919. Anal. Calcd for $C_{14}H_{11}N_3O_2$: C, 66.40; H, 4.38; N, 16.59. Found: C, 66.22; H, 4.42; N, 16.25.

| PREP # | Product (Chemical Name) | Starting Material A | Starting Material B | Physical Data | Comments |
|---|---|---|---|---|---|
| 13 | 2-(6-Methyl-pyridin-2-yl)-6-phenyl-pyrazolo[1,5-a]pyridine-3-carboxylic acid and 2-(6-Methyl-pyridin-2-yl)-4-phenyl-pyrazolo[1,5-a]pyridine-3-carboxylic acid | 2-(6-Methyl-pyridin-2-yl)-6-phenyl-pyrazolo[1,5-a]pyridine-3-carboxylic acid ethyl ester (Isomer 1) and 2-(6-Methyl-pyridin-2-yl)-4-phenyl-pyrazolo[1,5-a]pyridine-3-carboxylic acid ethyl ester(Isomer 2) (Prep. 8) | | MS ES− m/e 328.1 (M − 1). | Product was isolated as a mixture |
| 14 | 6-Methanesulfonyl-2-(6-methyl-pyridin-2-yl)-pyrazolo[1,5-a]pyridine-3-carboxylic acid | PREP. 9 | | MS ES+ m/e 332.1 (M + 1), MS ES− m/e 330.2 (M − 1). | |
| 15 | 2-Pyridin-2-yl-pyrazolo[1,5-a]pyridine-3-carboxylic acid | PREP. 10 | | MS ES− m/e 238 (M − 1). | |
| 16 | 2-(6-Ethyl-pyridin-2-yl)-pyrazolo[1,5-a]pyridine-3-carboxylic acid | PREP. 11 | | MS ES− m/e 266.1 (M − 1). | |

PREPARATION 17

3-Bromo-2-(6-methyl-pyridin-2-yl)-pyrazolo[1,5-a]pyridine

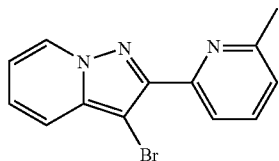

A solution of 2-(6-methyl-pyridin-2-yl)-pyrazolo[1,5-a]pyridine-3-carboxylic acid (0.92 g, 3.6 mmol), sodium bicarbonate (1.04 g, 12.4 mmol), and N-bromosuccinimide (0.71 g, 4.0 mmol) in DMF (25 mL) is stirred for 2 hours at room temperature. The reaction is then diluted with water (50 mL) and extracted with EtOAc (3×15 mL). The organic layer is washed with brine and dried over sodium sulfate. The solvent is removed in vacuo to afford 0.91 g (87%) of desired product as a dark green solid. UV (95% EtOH) $\lambda_{max}$ 282 nm ($\epsilon$ 12089), 233 nm ($\epsilon$ 21813). TOF MS ES$^+$ exact mass calculated for $C_{13}H_{10}BrN_3$ (p+1): m/z=288.0136. Found: 287.0058. Anal. Calcd for $C_{13}H_{10}BrN_3$: C, 54.19; H, 3.50; N, 14.58. Found: C, 54.10; H, 3.60; N, 14.48.

| PREP # | Product (Chemical Name) | Starting Material A | Starting Material B | Physical Data | Comments |
|---|---|---|---|---|---|
| 18 | 3-Bromo-2-(6-methyl-pyridin-2-yl)-6-phenyl-pyrazolo[1,5-a]pyridine | 2-(6-Methyl-pyridin-2-yl)-6-phenyl-pyrazolo[1,5-a]pyridine-3-carboxylic acid and 2-(6-Methyl-pyridin-2-yl)-4-phenyl-pyrazolo[1,5-a]pyridine-3-carboxylic acid (Prep. 13) | | MS ES$^+$ m/e 364.1, 366.1 (M + 1). | Mixture was separated by Silica Gel chromatography: (hexanes, EtOAc) |
| 19 | 3-Bromo-2-(6-methyl-pyridin-2-yl)-4-phenyl-pyrazolo[1,5-a]pyridine | 2-(6-Methyl-pyridin-2-yl)-6-phenyl-pyrazolo[1,5-a]pyridine-3-carboxylic acid and 2-(6-Methyl-pyridin-2-yl)-4-phenyl-pyrazolo[1,5-a]pyridine-3-carboxylic acid (Prep. 13) | | MS ES$^+$ m/e 364.1, 366.1. (M + 1). | Mixture was separated by chromatography, as above |
| 20 | 3-Bromo-6-methanesulfonyl-2-(6-methyl-pyridin-2-yl)-pyrazolo[1,5-a]pyridine | 6-Methanesulfonyl-2-(6-methyl-pyridin-2-yl)-pyrazolo[1,5-a]pyridine-3-carboxylic acid (Prep. 14) | | Exact Mass calculated 365.9912, found 365.9923 | |
| 21 | 3-Bromo-2-pyridin-2-yl-pyrazolo[1,5-a]pyridine | 2-Pyridin-2-yl-pyrazolo[1,5-a]pyridine-3-carboxylic acid (Prep. 15) | | MS ES$^+$ m/e 273.9, 275.9 (M + 1). | |
| 22 | 3-Bromo-2-(6-ethyl-pyridin-2-yl)-pyrazolo[1,5-a]pyridine | 2-(6-Ethyl-pyridin-2-yl)-pyrazolo[1,5-a]pyridine-3-carboxylic acid (Prep. 16) | | MS ES$^+$ m/e 302.0, 304.0 (M + 1). | |

PREPARATION 23

3-Methanesulfonyl-pyridine

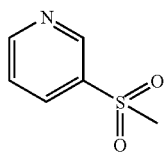

To a solution of 3-bromopyridine (20 g, 127 mmol) in THF (200 ml) at room temperature is added a solution of 2M isopropylmagnesium chloride in THF (64 ml, 127 mmol). The resulting mixture is stirred for 2 hours, treated with triethylamine (20 ml), immediately followed by methanesulfonylchloride (10 ml, 127 mmol) and the resulting mixture stirred for 18 hours at room temperature. The mixture is diluted with water (200 ml) and extracted with EtOAc (3×100 ml). The mixture is concentrated in vacuo and purified on Silica gel (eluting with 50/50 Hexane/EtOAc). $^1$H-NMR (CDCl$_3$) δ: 9.17 (s, 1H), 8.90 (d, 1H), 8.25 (dd, 1H), 7.55 (m, 1H), 3.12 (s, 3H).

PREPARATION 24

6-Ethoxy-4-methyl-quinoline

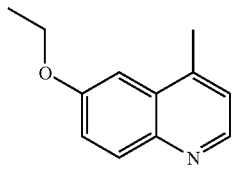

4-Ethoxyaniline (15 g, 109 mmol) in dissolved in dioxane (1 L) and cooled to 0° C. in an ice bath. To this mixture is added H$_2$SO$_4$ (12 mL, 219 mmol) dropwise with stirring and heating at 100° C. Water (2 mL) is added followed by methyl vinyl ketone (13 mL, 163 mmol, in 125 mL of dioxane) dropwise over 2 hours. The mixture is heated for 1 hour after addition and then cooled. To the residue is added 1.5 eq of 1M aqueous Na$_2$CO$_3$ until the pH is 8. The organic layer is separated, condensed to an oil, and purified on silica gel (eluting with 50/50 hexane/EtOAc).

The desired product is isolated as a solid 6 g (30%). TOF MS ES$^+$ (M+1) 188.1079.

PREPARATION 25

2-(6-Ethoxy-quinolin-4-yl)-1-(6-methyl-pyridin-2-yl)-ethanone

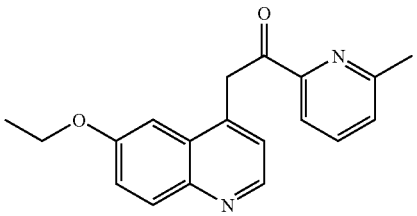

To a solution of 6-ethoxy-4-methyl-quinoline (360 mg, 2.0 mmol) in THF at −78° C. add 1.5M lithium diisopropylamide (4.6 ml, 7.0 mmol) dropwise and stir for 1 hour. 6-Methyl-pyridine-2-carboxylic acid methoxy-methyl-amide (430 mg, 2.4 mmol) is then added, and the mixture stirred for 30 minutes at −78° C. before quenching with 1N HCl (5 ml). Neutralize with saturated aqueous NaHCO$_3$ and extract with EtOAc (3×50 ml). The organic phase is then dried with MgSO$_4$ and concentrated in vacuo. The crude product was chromatographed on silica gel (elute with 50/50 Hexane/EtOAc) to give 120 mg (20%) of the title compound. MS ES$^+$ m/e 307.1 (M+1).

PREPARATION 26

4-Benzyl-pyridin-1-yl-ammonium 2,4,6-trimethyl-benzenesulfonate

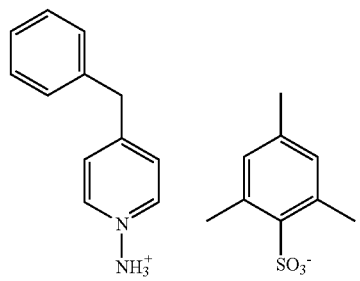

A solution of 4-benzyl pyridine (0.6 g, 3.5 mmol) in methylene chloride (5 ml) is cooled with ice bath. Freshly prepared O-(2,4,6-trimethyl-benzenesulfonyl)hydroxylamine (0.92 g, 4.2 mmol) in methylene chloride (5 ml) is added dropwise with stirring. The ice bath is removed and the mixture stirred for 1 hour, then concentrated in vacuo. The residue is dissolved in methylene chloride and precipitated with hexanes. The hexane layer is decanted. Concentration provides 1.0 g (62%) of the title compound as a viscous oil.

$^1$H NMR (CD$_3$OD) δ 8.63-8.53 (m, 2H), 7.84-7.71 (m, 2H), 7.41-7.22 (m, 5H), 6.85 (s, 2H), 4.21 (s, 2H), 2.60 (s, 6H), 2.22 (s, 3H).

By the method of PREPARATION 26 the following compounds were prepared:

| Prep. # | Product Name | Physical Data |
|---|---|---|
| 27 | 1-Amino-3-phenyl-pyridinium-2,4,6-trimethyl-benzenesulfonic acid anion | $^1$H-NMR(CDCl$_3$): δ 9.24(s, 1H), 9.01 (d, 1H, J=4Hz), 7.97(d, 1H, J=2Hz), 7.68(t, 1H, J=2Hz), 7.56(d, 2H, J=4Hz), 7.38(m, 2H), 6.79(s, 2H), 2.63(s, 6H), 2.19(s, 3H). |
| 28 | 1-Amino-4-phenyl-pyridinium-2,4,6-trimethyl-benzenesulfonic acid anion | $^1$H-NMR(CDCl$_3$): δ 8.97(d, 2H, J=4Hz), 8.04(d, 2H, J=4Hz), 7.72(d, 2H, J=6Hz), 7.26(m, 3H), 2.81(s, 2H), 2.64(s, 6H), 2.20(s, 3H). |
| 29 | 1-Amino-3-methanesulfonyl-pyridinium-2,4,6-trimethyl-benzenesulfonic acid anion | $^1$H-NMR(CDCl$_3$): δ 9.30(s, 1H), 8.97 (d, 1H), 8.72(d, 1H), 8.16(t, 1H), 6.88 (s, 2H), 2.61(s, 6H), 2.37(s, 3H). |
| 30 | 1-Amino-3-methoxycarbonyl-pyridinium-2,4,6-trimethyl-benzenesulfonic acid anion | $^1$H-NMR(CDCl$_3$): δ 9.43(s, 2H), 8.40 (d, 1H), 7.78(t, 1H), 6.82(s, 2H), 3.93 (s, 3H), 2.63(s, 6H), 2.24(s, 3H) |
| 31 | 4-Methoxycarbonyl-pyridin-1-yl-ammonium 2,4,6-trimethyl-benzenesulfonate | $^1$H NMR(CD$_3$OD): δ 8.84-8.79(m, 2H), 8.39-8.31(m, 2H), 6.84(s, 2H), 4.01(s, 3H), 2.59(s, 6H), 2.22(s, 3H) |
| 32 | 3-Ethoxycarbonyl-pyridin-1-yl-ammonium 2,4,6-trimethyl-benzenesulfonate | $^1$H NMR(CD$_3$OD): δ 9.24(s, 1H), 8.09-8.85(m, 1H), 8.75-8.66(m, 1H), 8.10-8.01(m, 1H), 6.85(s, 2H), 4.53-4.43(m, 2H), 2.61(s, 6H), 2.22(s, 3H), 1.48-1.36(m, 3H) |
| 33 | 1-Amino-3-iodo-pyridinium-2,4,6-trimethyl-benzenesulfonic acid anion | $^1$H-NMR(CDCl$_3$): δ 9.06(s, 1H), 8.71 (d, 1H), 8.57(d, 1H), 7.67(t, 1H), 6.86 (s, 2H), 2.61(s, 6H), 2.23(s, 3H). |

PREPARATION 34

2-(4-Fluorophenyl)-1-pyridin-2-yl-ethanone

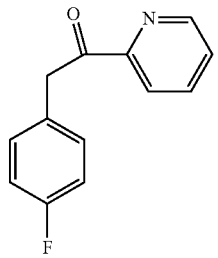

Combine a solution of 4-fluorophenylacetonitrile (1.00 g, 7.4 mmol) and ethyl picolinate (1.12 g, 7.4 mmol) in absolute ethyl alcohol (15 mL) under N$_2$ with 21 wt % sodium ethoxide solution in denatured ethyl alcohol (4.2 mL, 11.1 mmol) and heat to reflux for 2 hours, then pour onto ice. Adjust the pH to 4 with concentrated hydrochloric acid and collect the precipitate by vacuum filtration. Dissolve the residue in 48% aqueous hydrobromic acid (25 mL) and heat to reflux for 2 hours. Pour the solution onto ice and adjust the pH to 7 with 5N aqueous sodium hydroxide solution. Extract the aqueous solution three times with CH$_2$Cl$_2$. Combine the organic extracts, dry (Na$_2$SO$_4$), filter, and concentrate in vacuo to afford the title compound 668 mg (42%) as a brown amorphous solid. MS FAB$^+$ m/z=216.1

By the method of PREPARATION 34 the following compounds were prepared:

| Prep. # | Product Name | Physical |
|---|---|---|
| 35 | 1-(6-Ethyl-pyridin-2-yl)-2-(4-fluoro-phenyl)-ethanone | $^1$H-NMR(CDCl$_3$) δ: 7.84(d, 1H), 7.72(t, 1H), 7.34-7.31(m, 3H), 7.09-6.96(m, 2H), 4.50(s, 2H), 2.90(q, 2H), 1.37(t, 3H) |
| 36 | 2-(4-Fluoro-phenyl)-1-(6-propyl-pyridin-2-yl)-ethanone | $^1$H-NMR(CDCl$_3$) δ: 7.85(d, 1H), 7.72(t, 1H), 7.31(m, 3H), 7.00(m, 2H), 4.51(s, 2H), 2.85(t, 2H), 1.83(m, 2H), 1.00(t, 3H) |
| 37 | 1-(6-Ethyl-pyridin-2-yl)-2-(4-fluoro-naphthalen-1-yl)-ethanone | MS ES$^+$ m/e 294.1 (M + 1). |
| 38 | 2-(4-Fluoro-phenyl)-1-(6-methyl-pyridin-2-yl)-ethanone | MS ES$^+$ m/e 230.09 (M + 1). |
| 39 | 2-(4-Methoxy-phenyl)-1-pyridin-2-yl-ethanone | MS ES$^+$ m/e 228.09 (M + 1). |
| 40 | 1-Pyridin-2-yl-2-(4-trifluoromethyl-phenyl)-ethanone | MS ES$^+$ m/e 266.07 (M + 1). |
| 41 | 2-(3-Chloro-4-fluoro-phenyl)-1-(6-methyl-pyridin-2-yl)-ethanone | $^1$H NMR(CDCl$_3$) δ 7.86-7.83(m, 1H), 7.73-7.71(m, 1H), 7.42-7.33(m, 2H), 7.26-7.04 (m, 2H), 4.49(s, 2H), 2.65(s, 3H). |

| Prep. # | Product Name | Physical |
|---|---|---|
| 42 | 1-(6-Methyl-pyridin-2-yl)-2-(2,4,5-trifluoro-phenyl)-ethanone | $^1$H NMR(CDCl$_3$) δ 7.87-7.85(m, 1H), 7.75-7.70(m, 1H), 7.37-7.34(m, 1H), 7.15-7.07 (m, 1H), 6.98-6.89(m, 1H), 4.55(s, 2H), 2.64(s, 3H) |
| 43 | 2-(4-Fluoro-3-trifluoromethyl-phenyl)-1-(6-methyl-pyridin-2-yl)-ethanone | $^1$H NMR(CDCl$_3$) δ 7.86-7.84(m, 1H), 7.74-7.62(m, 2H), 7.53-7.49(m, 1H), 7.36-7.33 (m, 1H), 7.16-7.10(m, 1H), 4.55(s, 2H), 2.65(s, 3H) |
| 44 | 1-(6-Chloro-pyridin-2-yl)-2-(4-fluoro-phenyl)-ethanone | $^1$H NMR(CDCl$_3$) δ 8.01-7.92(m, 1H), 7.86-7.75(m, 1H), 7.57-7.50(m, 1H), 7.35-7.22(m, 2H), 7.08-6.93(m, 2H), 4.47 (s, 2H). TLC (SiO$_2$): R$_f$0.57(30% ethyl acetate/hexanes) |

PREPARATION 45

1-Pyridin-2-yl-2-quinolin-4-yl-ethanone

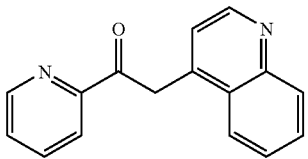

To a solution of diisopropylamine (44.9 mL, 320 mmol) in THF (500 mL) at −78° C. add 1.6 M n-butyl lithium in hexane (200 mL, 320 mmol). Stir for 10 minutes and add dropwise a solution of lepidine (42.9 g, 300 mmol) in THF (200 mL) over 20 minutes at −78° C. and quickly add a solution of ethyl picolinate (48.3 g, 320 mmol). Allow the reaction to warm slowly to 0° C. and quench by pouring into water (1 L). Add ethyl acetate (1 L). Dissolve residual solids by adding Acetic acid (20 mL). Separate the layers and extract the aqueous layer with one portion of ethyl acetate (100 mL). Combine the organic extracts, dry over sodium sulfate, and concentrate in vacuo. Triturate the crude oil with hexane/ether to give 36 g of the title compound. Concentrate the filtrate. Chromatograph the residue on silica gel (elute with 10:9:1 CH$_2$Cl$_2$, ether, MeOH). Precipitate the purified product from ether/hexane to give 21 g of the title compound. Combined yield: 57 g (76%) of title compound as a yellow crystalline solid. MS ES$^+$ m/e 249.0 (M+1).

By the method of PREPARATION 45 the following compounds were prepared:

| Prep. # | Product Name | Physical data | Comments |
|---|---|---|---|
| 46 | 2-(6,7-Dimethoxy-quinolin-4-yl)-1-(6-methyl-pyridin-2-yl)-ethanone | MS ES$^+$ m/e 323.1 (M + 1). | |
| 47 | 2-(6-Ethoxy-quinolin-4-yl)-1-(6-methyl-pyridin-2-yl)-ethanone | MS ES$^+$ m/e 307.1 (M + 1). | |
| 48 | 1-Pyridin-2-yl-2-quinolin-4-yl-ethanone | MS ES$^+$ m/e 251 (M + 1). | |
| 49 | 2-(7-Ethoxy-quinolin-4-yl)-1-pyridin-2-yl-ethanone | $^1$H-NMR(CDCL$_3$): δ 8.74(d, 1H, J=4Hz), 7.97(d, 1H, J=8Hz), 7.84(d, 1H, J=8Hz), 7.71(t, 1H, J=8Hz), 7.42(d, 1H, J=8Hz), 7.36(s, 1H, J=4Hz), 7.26(m, 1H, J=4Hz), 7.18(d, 1H, J=4Hz), 4.97(s, 2H, J=4Hz), 4.18(q, 2H, J=5Hz), 2.60(s, 3H, J=4Hz), 1.48(t, 3H, J=7Hz) | |
| 50 | 2-(7-Ethoxy-quinolin-4-yl)-1-(6-methyl-pyridin-2-yl)-ethanone | MS ES$^+$ m/e 307.1 (M + 1). | |
| 51 | 1-(6-Methyl-pyridin-2-yl)-2-quinolin-4-yl-ethanone | MS ES$^+$ m/e 263.1 (M + 1). | |
| 52 | 1-(6-Ethyl-pyridin-2-yl)-2-quinolin-4-yl-ethanone | MS ES$^+$ m/e 277.33 (M + 1). | |
| 53 | 1-Furan-2-yl-2-quinolin-4-yl-ethanone | TOF MS exact mass m/z = 238.0868. Found: 238.0888. | |
| 54 | 2-Quinolin-4-yl-1-thiophen-2-yl-ethanone | TOF MS exact mass m/z = 254.0640. Found: 254.0657. | |
| 55 | 1-Pyridin-2-yl-2-pyridin-4-yl-ethanone | MS ES$^+$ m/e 199.2 (M + 1). | KHMDS |

-continued

| Prep. # | Product Name | Physical data | Comments |
|---|---|---|---|
| 56 | 2-(6-Ethoxy-quinolin-4-yl)-1-(6-methyl-pyridin-2-yl)-ethanone | MS ES$^+$ m/e 307.1 (M + 1). | |
| 57 | 1-(6-Chloro-pyridin-2-yl)-2-quinolin-4-yl-ethanone | $^1$H NMR(CDCl$_3$): δ 8.81(m, 1H), 8.08(m, 1H), 7.96(m, 2H), 7.76(m, 1H), 7.63(m, 1H), 7.41 (m, 2H), 7.34(m, 1H), 4.94(s, 2H). | |
| 58 | 1-(6-Fluoro-pyridin-2-yl)-2-quinolin-4-yl-ethanone | MS APCI$^+$ m/e 267(M + 1). TLC (SiO$_2$): R$_f$ 0.30(1:2 acetone/hexanes) | |
| 59 | 1-(5-Butyl-pyridin-2-yl)-2-quinolin-4-yl-ethanone | TLC (SiO$_2$): R$_f$ 0.40(1:1 acetone/hexanes) | |
| 60 | 2-(8-Fluoro-quinolin-4-yl)-1-(6-methyl-pyridin-2-yl)-ethanone | $^1$H NMR(CDCl$_3$) δ 8.90-8.85 (m, 1H), 7.90-7.70(m, 2H), 7.50-7.30(m, 3H), 5.05(s, 2H), 2.70(s, 3H). | KHMDS |
| 61 | 1-(6-Methyl-pyridin-2-yl)-2-(6-trifluoromethyl-quinolin-4-yl)-ethanone | $^1$H NMR(CDCl$_3$) δ 8.97-8.94 (m, 1H), 8.55-8.51(m, 1H), 8.25-8.20(m, 1H), 7.98-7.93(m, 1H), 7.89-7.83(m, 1H), 7.77-7.69(m, 1H), 7.54-7.50(m, 1H), 7.41-7.32(m, 1H), 5.00(s, 2H), 2.69(s, 3H). | |
| 62 | 2-(7-Bromo-quinolin-4-yl)-1-(6-methyl-pyridin-2-yl)-ethanone | $^1$H NMR(CDCl$_3$) δ 8.85(m, 1H), 8.30(s, 1H), 8.00-7.60(m, 4H), 7.45-7.35(m, 2H), 5.05(s, 2H), 2.65(s, 3H). | |
| 63 | 2-(7-Trifluoromethyl-quinolin-4-yl)-1-(6-methyl-pyridin-2-yl)-ethanone | $^1$H NMR(CDCl$_3$) δ 8.88(m, 1H), 8.15-8.10(m, 1H), 8.00(s, 1H), 7.98-7.80(m, 2H), 7.75-7.65(m, 1H), 7.50(m, 1H), 7.35-7.33(m, 1H), 5.00(s, 2H), 2.70(s, 3H) | |
| 64 | 2-(6-Bromo-quinolin-4-yl)-1-(6-methyl-pyridin-2-yl)-ethanone | $^1$H NMR(CDCl$_3$) δ 8.89-8.81 (m, 1H), 8.40(s, 1H), 8.03-7.99 (m, 1H), 7.90-7.85(m, 1H), 7.79-7.67(m, 2H), 7.49-7.38(m, 2H), 4.97(s, 2H), 2.71(s, 3H) | |
| 65 | 1-Pyridin-2-yl-2-quinolin-4-yl-ethanone | $^1$H NMR(CDCl$_3$) δ 8.85-8.80 (m, 1H), 8.10-8.00(m, 2H), 7.85-7.87(m, 1H), 7.73-7.60(m, 2H), 7.50-7.43(m, 1H), 7.40-7.30(m, 2H), 5.00(s, 2H) | KHMDS |
| 66 | 2-(7-Bromo-quinolin-4-yl)-1-pyridin-2-yl-ethanone | $^1$H NMR(CDCl$_3$) δ 8.85(m, 1H), 8.30(s, 1H), 8.00-7.60 (m, 4H), 7.45-7.35(m, 3H), 5.05 (s, 2H) | KHMDS |
| 67 | 2-(7-Methoxy-quinolin-4-yl)-1-(6-methyl-pyridin-2-yl)-ethanone | $^1$H NMR(CDCl$_3$) δ 8.79-8.72 (m, 1H), 8.01-7.96(m, 1H), 7.90-7.83(m, 1H), 7.79-7.70 (m, 1H), 7.49-7.42(m, 1H), 7.40-7.37(m, 1H), 7.30-7.24(m, 1H), 7.23-7.20(m, 1H), 5.05(s, 2H), 3.94(s, 3H), 2.70(s, 3H). | KHMDS |
| 68 | 2-(7-Methoxy-quinolin-4-yl)-1-pyridin-2-yl-ethanone | MS APCI$^+$ m/e 279 (M + 1). | KHMDS |
| 69 | 2-(7-Chloro-quinoline-4-yl)-1-(6-methyl-pyridin-2-yl)-ethanone | mp 88-90° C. EA Calcd. for C$_{17}$H$_{13}$ClN$_2$O: C, 68.81; H, 4.41; O, 9.44; Found: C, 48.48; H, 4.38; N, 9.63 | |
| 70 | 2-(6,7-di-Fluoro-quinoline-4-yl)-1-(6-methyl-pyridin-2-yl)-ethanone | MS ES$^+$ m/e 299 (M + 1). | |
| 71 | 2-(6,7-di-Chloro-quinolin-4-yl)-1-6-ethyl-pyridin-2-yl)-ethanone | MS ES$^-$ m/e 343 (M − 1). | |

PREPARATION 72

2-(6-Methyl-pyridin-2-yl)-pyrazolo[1,5-a]pyridine-3-boronic acid

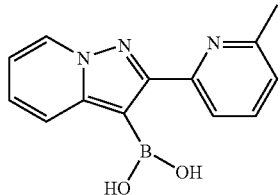

A solution of 3-bromo-2-(6-methyl-pyridin-2-yl)-pyrazolo[1,5-a]pyridine (PREP. 17, 0.2 g, 0.69 mmol) in THF (10 mL) is cooled to −78° C. and treated with tert-butyllithium (1.7 M in pentane, 1.6 mL, 2.8 mmol). This solution is stirred for 30 minutes at −78° C., treated with triisopropyl borate (0.39 g, 2.08 mmol), and stirred for 2 hr at −78° C. The reaction is then quenched with 1N HCl and stirred for 30 minutes at room temp. Evaporation leads to the solid crude product that is used without further purification. MS ES$^+$ m/e 253.9 (M+1).

PREPARATION 73

Methyl 6-chloropicolinate

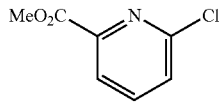

Add thionyl chloride (3.7 mL, 50.8 mmol) to a solution of 6-chloropicolinic acid (4.0 g, 25.4 mmol) in methanol (85 mL) at 0° C. Stir the resultant solution for 15 minutes at 0° C., 0.5 hours at room temperature, and 6 hours at 50° C. Concentrate the reaction in vacuo and dilute with CHCl$_3$ (150 mL). Wash the organic solution with saturated aqueous sodium bicarbonate (3×100 mL), and brine (1×100 mL) and dry with sodium sulfate. Filtration and concentration afford methyl 6-chloropicolinate 4.38 g (100%) as a white solid.

$^1$H NMR (CDCl$_3$): δ 8.05 (m, 1H), 7.73 (m, 1H), 7.42 (m, 1H), 3.95 (s, 3H).

PREPARATION 74

6-Fluoro-pyridine-2-carboxylic acid

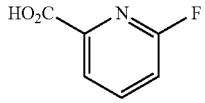

Add potassium permanganate (12.8 g, 81.0 mmol) to a solution of 2-fluoro-5-methylpyridine (3.0 g, 27.0 mmol) in water (135 mL). Heat the reaction to 100° C. for 4 hours. While the reaction is hot, filter through Celite® Rinse the filter cake with hot water (2×50 mL) and concentrate the combined aqueous solutions in vacuo to a volume of 50 mL. Acidify with concentrated HCl and concentrate to dryness in vacuo to provide the title compound as a white solid which is used directly in the next step. MS APCI$^+$ m/e 142 (M+1).

PREPARATION 75

6-Fluoro-pyridine-2-carboxylic acid methoxy-methyl-amide

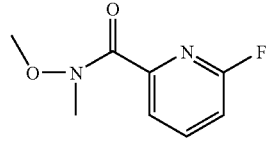

Add N-methylmorpholine (6 mL, 52 mmol) and isobutylchloroformate (3.5 mL, 26.9 mmol) to a solution of 6-fluoropyridine-2-carboxylic acid (3.8 g, 26.9 mmol) in methylene chloride at 0° C. After 15 minutes add O,N-dimethylhydroxylamine hydrochloride (2.6 g, 26.9 mmol) and N-methylmorpholine (3 mL, 26.9 mmol). Stir the reaction at 0° C. for 15 minutes and then room temperature for 17 hours. Dilute the reaction with methylene chloride and wash sequentially with water (1×50 mL), 10% aqueous citric acid (1×50 mL), brine (1×50 mL), saturated aqueous sodium bicarbonate (1×50 mL), and brine (1×50 mL). Dry the resulting organic solution with Na$_2$SO$_4$, filter, and purify by flash column chromatography (Silica Gel, 20% acetone/hexanes) to provide the title compound 0.97 g (18% from 2-fluoro-5-methylpyridine) as a clear, yellow oil.

MS APCI$^+$ m/e 185 (M+1).
TLC (SiO$_2$): Rf 0.40 (1:3 acetone/hexanes).

PREPARATION 76

5-Butyl-pyridine-2-carboxylic acid methoxy-methyl-amide

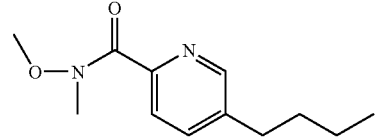

Add N-methylmorpholine (1.22 mL, 11.1 mmol) and isobutylchloroformate (1.44 mL, 11.1 mmol) to a solution of fusaric acid (2.0 g, 11.1 mmol) in methylene chloride at 0° C. After 15 minutes add O,N-dimethylhydroxylamine hydrochloride (1.1 g, 11.1 mmol) and N-methylmorpholine (1.22 mL, 11.1 mmol). Stir the reaction for at 0° C. 15 minutes and then room temperature for 19 hours. Dilute the reaction with methylene chloride and wash with water (1×50 mL), 10% aqueous citric acid (1×50 mL), brine (1×50 mL), saturated aqueous sodium bicarbonate (1×50 mL), and brine (1×50 mL). Dry the organic solution with sodium sulfate, filter, and concentrate in vacuo to provide the title compound 3.2 g (100%) as a clear yellow oil.

MS APCI$^+$ m/e 201 (M+1). TLC (SiO$_2$): R$_f$ 0.70 (1:1 ethyl acetate/methylene chloride).

PREPARATION 77

8-Fluoro-4-methyl-quinoline

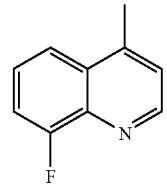

Add H$_2$SO$_4$ (14.4 mL, 270 mmol) to a solution of 2-fluoroaniline (20.0 g, 180 mmol) in 1,4-dioxane (1 L) at room temperature. Heat the mixture to reflux and add methyl vinyl ketone (19.5 mL, 270 mmol) in 1,4-dioxane (50 mL) dropwise over 3 hours. Continue to heat for 1 hour after the addition, then remove the solvent under vacuum. Dissolve the residue in water (100 mL), neutralize with Na$_2$CO$_3$ and extract with CH$_2$Cl$_2$. Wash the combined organic extracts with water and brine, dry with anhydrous Na$_2$SO$_4$ and filter the mixture. Concentrate the filtrate; chromatograph the residue with silica gel (elute with 20% EtOAc in hexanes) to give the title compound 12 g (41%) as a yellowish solid.

$^1$H NMR (CDCl$_3$) δ 8.80-8.75 (m, 1H), 7.85-7.80 (m, 3H), 7.60-7.30 (m, 3H), 3.70 (s, 3H).

By the method of PREPARATION 77 the following compounds were prepared:

| PREP. # | Product (Chemical Name) | Physical Data |
|---|---|---|
| 78 | 6-Bromo-4-methyl-quinoline | $^1$H NMR(CDCl$_3$) δ 8.78-8.75(m, 1H), 8.16-8.11 (m, 1H), 7.99-7.91(m, 1H), 7.81-7.72(m, 1H), 7.28-7.19 9m, 1H), 2.67(s, 3H). |
| 79 | 7-Trifluoromethyl-4-methyl-quinoline | $^1$H NMR(CDCl$_3$) δ 8.80-8.75(m, 1H), 8.15-8.10 (m, 1H), 7.80(s, 1H), 7.60-7.55(m, 1H), 7.30-7.27 (m, 1H), 2.70(s, 3H). |
| 80 | 7-Bromo-4-methyl-quinoline | $^1$H NMR(CDCl$_3$) δ 8.80-8.75 (m, 1H), 8.30 (s, 1H), 7.90-7.85(m, 1H), 7.70-7.65(m, 1H), 7.25-7.20(m, 1H), 2.65(s, 3H). |
| 81 | 4-Methyl-6-trifluoromethyl-quinoline | $^1$H NMR(CDCl$_3$) δ 8.91-8.86(m, 1H), 8.32(s, 1H), 8.27-8.19(m, 1H), 7.91-7.86(m, 1H), 7.39-7.32(m, 1H), 2.69(s, 3H). |
| 82 | 7-Methoxy-4-methyl-quinoline | $^1$H NMR(CDCl$_3$) δ 8.71-8.66(m, 1H), 7.91-7.87 (m, 1H), 7.44-7.40(m, 1H), 7.28-7.18(m, 1H), 7.11-7.06(m, 1H), 3.95(s, 3H), 2.67(s, 3H). |
| 83 | 7-Chloro-4-methyl-quinoline | |
| 84 | 7-Ethoxy-4-methyl-quinoline | TOF MS ES$^+$ exact mass calculated for C$_{12}$H$_{14}$NO (p + 1): m/z = 188.1075 Found: 188.1059 |
| 85 | 6,7-di-Methoxy-4-methyl-quinoline | TOF MS ES$^+$ exact mass calculated for C$_{12}$H$_{14}$NO$_2$ (p + 1): m/z = 204.1025 Found: 204.1010 |
| 86 | 6,7-di-Chloro-4-methyl-quinoline | MS ES$^+$ m/e 212 (M + 1) |
| 87 | 6,7-di-Fluoro-4-methyl-quinoline | MS ES$^+$ m/e 212 (M + 1) |
| 88 | 6-Ethoxy-4-methyl-quinoline | TOF MS ES$^+$ exact mass calculated for C$_{12}$H$_{14}$NO (p + 1): m/z = 188.1075. Found: 188.1079 |

PREPARATION 89

5-Bromo-benzofuran-2-carboxylic acid ethyl ester

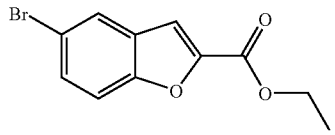

A solution of 5-bromo-salicylaldehyde (5.0 g, 25 mmol) and bromo diethylmalonate (8.9 g, 37 mmol) in methyl ethyl ketone (50 mL) is treated with potassium carbonate (6.8 g, 50 mmol) and heated to reflux. The reaction is stirred over 3 days at reflux. The reaction is then concentrated to a crude solid that is purified by silica gel column chromatography (9:1 hexane/EtOAc) to afford 5.2 g (78%) of the desired product. 1H NMR (CDCl3) 7.81 (d, 1H), 7.26-7.55 (m, 3H), 4.44 (q, 2H), 1.42 (t, 3H).

PREPARATION 90

4-[2-(6-Methyl-pyridin-2-yl)-pyrazolo[1,5-a]pyridin-3-yl]-quinolin-7-ol

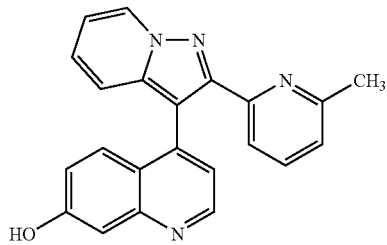

To a solution of 7-methoxy-4-[2-(6-methyl-pyridin-2-yl)-pyrazolo[1,5-a]pyridin-3-yl]-quinoline (1.3 g, 3.57 mmol) in DMF (36 mL), add ethanethiol (5.3 mL, 71.4 mmol), followed by sodium hydride (60% dispersion in mineral oil, 2.9 g, 71.4 mmol). After all of the gas has evolved, the mixture is heated at 80° C. for 4 hours, then cooled to room temperature. Saturated aqueous NH$_4$Cl (5 mL) is added, and the mixture concentrated. The residue is dissolved in methylene chloride, washed with water and concentrated to give the title compound 1.16 g (93%) as a yellow solid.

$^1$H NMR (CD$_3$OD) δ 8.73-8.68 (m, 1H), 8.60-8.56 (m, 1H), 7.56-7.49 (m, 1H), 7.41-7.18 (m, 5H), 7.15-7.01 (m, 3H), 6.89-6.82 (m, 1H), 2.32 (s, 3H).

PREPARATION 91

4-(2-Pyridin-2-yl-pyrazolo[1,5-a]pyridin-3-yl)quinolin-7-ol

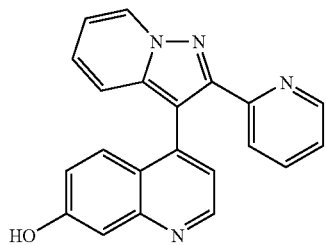

Add ethanethiol (6.8 mL, 92.5 mmol), followed by a sodium hydride (60% dispersion in mineral oil, 3.7 g, 92.5 mmol) to a solution of 7-methoxy-4-(2-pyridin-2-yl-pyrazolo[1,5-a]pyridin-3-yl)-quinoline (1.63 g, 4.6 mmol) in DMF (50 mL) at room temperature. Following the same procedure described above affords the title compound 0.8 g (52%) as a yellow solid.

PREPARATION 92

7-(3-Chloro-propoxy)-4-(2-pyridin-2-yl-pyrazolo[1,5-a]pyridin-3-yl)-quinoline

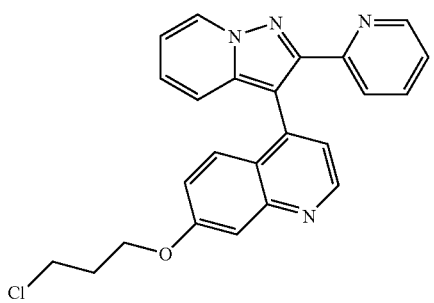

4-(2-Pyridin-2-yl-pyrazolo[1,5-a]pyridin-3-yl)-quinolin-7-ol in a solution of DMF and MeOH is treated with 1-bromo-3-chloropropane (3 equiv) and cesium carbonate (2 equiv). The reaction is heated to 60° C. and stirred overnight. The reaction is then purified on silica gel column (see Prep. 77) chromatography to afford the desired product.

MS ES$^+$ m/e 415.0 (M+1).

PREPARATION 93

7-(2-Chloro-ethoxy)-4-(2-pyridin-2-yl-pyrazolo[1,5-a]pyridin-3-yl)-quinoline

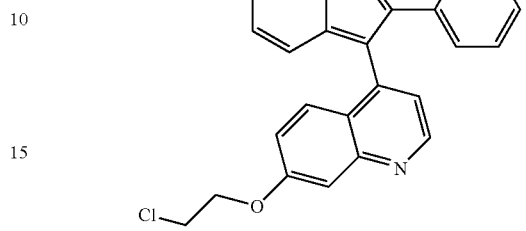

4-(2-Pyridin-2-yl-pyrazolo[1,5-a]pyridin-3-yl)-quinolin-7-ol in a solution of DMF and MeOH was treated with 1-bromo-2-chloroethane (3 equiv) and cesium carbonate (2 equiv). The reaction was heated to 60° C. and stirred overnight. As described above, the desired product was then obtained upon chromatographic purification (EtOAc, followed by MeOH, then 2 M NH$_3$ in MeOH). Yield; 30% overall from Prep. 90. MS ES$^+$ m/e 401.0 (M+1).

EXAMPLE 1

3-(4-Fluoro-phenyl)-2-(6-methyl-pyridin-2-yl)-pyrazolo[1,5-a]pyridine

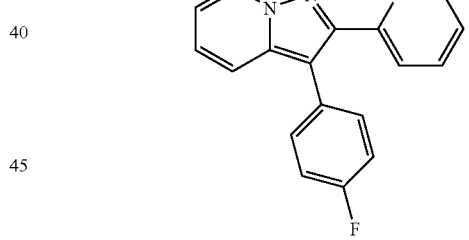

A solution of 3-bromo-2-(6-methyl-pyridin-2-yl)-pyrazolo[1,5-a]pyridine (0.25 g, 0.9 mmol) and p-fluorophenylboronic acid (0.15 g, 1.04 mmol), in DME (10 mL) is purged with argon. The solution is treated with NaOH (0.07 g, 1.7 mmol) and (PPh$_3$)$_4$Pd (0.05 g, 0.04 mmol) then heated at reflux overnight. The reaction is then cooled, diluted in EtOAc, and washed with water and brine. The organic solution is dried over MgSO$_4$ and the solvent removed in vacuo. The residue is purified by silica gel column chromatography using a mixture of hexanes/EtOAc to afford 0.164 g (62%) of desired product as a white solid. UV (95% EtOH) $\lambda_{max}$ 248 nm ($\epsilon$ 20386). TOF MS ES$^+$ exact mass calculated for C$_{19}$H$_{14}$FN$_3$ (p+1): m/z=304.1250. Found: 304.1249. Anal. Calcd for C$_{19}$H$_{14}$FN$_3$: C, 75.23; H, 4.65; N, 13.85. Found: C, 75.10; H, 4.76; N, 13.70.

By the method of EXAMPLE 1 the following compounds were prepared:

| EX # | Product (Chemical Name) | Starting Material A | Starting Material B | Physical Data | Comments |
|---|---|---|---|---|---|
| 2 | Dimethyl-{4-[2-(6-methyl-pyridin-2-yl)-pyrazolo[1,5-a]pyridin-3-yl]-phenyl}-amine | 3-Bromo-2-(6-methyl-pyridin-2-yl)-pyrazolo[1,5-a]pyridine (Prep. 17) | 4-(N,N-Dimethylamino)Phenyl boronic acid | TOF MS ES$^+$ exact mass calculated for $C_{21}H_{120}N_4$ (p + 1): m/z = 329.1766. Found: 329.1768. | |
| 3 | 3-(4-Methoxy-phenyl)-2-(6-methyl-pyridin-2-yl)-pyrazolo[1,5-a]pyridine | 3-Bromo-2-(6-methyl-pyridin-2-yl)-pyrazolo[1,5-a]pyridine (Prep. 17) | p-methoxyphenylboronic acid | Anal. Calcd for $C_{20}H_{17}N_3O$: C, 76.17; H, 5.43; N, 13.32. Found: C, 75.84; H, 5.42; N, 13.07. | |
| 4 | 3-(4-Methanesulfonyl-phenyl)-2-(6-methyl-pyridin-2-yl)-pyrazolo[1,5-a]pyridine | 3-Bromo-2-(6-methyl-pyridin-2-yl)-pyrazolo[1,5-a]pyridine (Prep. 17) | 4-(Methanesulfonyl)benzeneboronic acid | TOF MS ES$^+$ exact mass calculated for $C_{20}H_{18}N_3O_2S$ (p + 1): m/z = 364.1120. Found: 364.1134 | |
| 5 | 2-(6-Methyl-pyridin-2-yl)-3-phenyl-pyrazolo[1,5-a]pyridine | 3-Bromo-2-(6-methyl-pyridin-2-yl)-pyrazolo[1,5-a]pyridine (Prep. 17) | Phenylboronic acid | Anal. Calcd for $C_{19}H_{15}N_3$: C, 79.98; H, 5.30; N, 14.73. Found: C, 79.94; H, 5.40; N, 14.59. | Use 5:1 Toluene:MeOH instead of DME as solvent. Use Na2CO3 instead of NaOH. |
| 6 | 2-(6-Methyl-pyridin-2-yl)-3-pyridin-4-yl-pyrazolo[1,5-a]pyridine | 3-Bromo-2-(6-methyl-pyridin-2-yl)-pyrazolo[1,5-a]pyridine (Prep. 17) | Pyridine-4-boronic acid | MS ES$^+$ m/e 287.2 (M + 1). | Use 5:1 Toluene:MeOH instead of DME as solvent. Use Na2CO3 instead of NaOH. |
| 7 | 3-(4-Fluoro-phenyl)-2-(6-methyl-pyridin-2-yl)-6-phenyl-pyrazolo[1,5-a]pyridine | 3-Bromo-2-(6-methyl-pyridin-2-yl)-6-phenyl-pyrazolo[1,5-a]pyridine (Prep. 18) | p-Fluorophenylboronic acid | MS ES$^+$ m/e 380.2 (M + 1). | Use 5:1 Toluene:MeOH instead of DME as solvent. Use Na2CO3 instead of NaOH. |
| 8 | 3-(4-Fluoro-phenyl)-6-methanesulfonyl-2-(6-methyl-pyridin-2-yl)-pyrazolo[1,5-a]pyridine | 3-Bromo-6-methanesulfonyl-2-(6-methyl-pyridin-2-yl)-pyrazolo[1,5-a]pyridine (Prep. 20) | p-Fluorophenylboronic acid | MS ES$^+$ m/e 382.1 (M + 1). | Use 5:1 Toluene:MeOH instead of DME as solvent. Use Na2CO3 instead of NaOH. |
| 9 | 2-(6-Methyl-pyridin-2-yl)-3-(4-trifluoromethyl-phenyl)- | 3-Bromo-2-(6-methyl-pyridin-2-yl)-pyrazolo[1,5-a] | 4-Trifluoromethylphenyl-boronic acid | MS ES$^+$ m/e 354.0 (M + 1). | Use 5:1 Toluene:MeOH instead of |

-continued

| EX # | Product (Chemical Name) | Starting Material A | Starting Material B | Physical Data | Comments |
|---|---|---|---|---|---|
| | pyrazolo[1,5-a]pyridine | a]pyridine (Prep. 17) | | | DME as solvent. Use Na2CO3 instead of NaOH. |
| 10 | 3-(6-Methoxy-pyridin-3-yl)-2-(6-methyl-pyridin-2-yl)-pyrazolo[1,5-a]pyridine | 3-Bromo-2-(6-methyl-pyridin-2-yl)-pyrazolo[1,5-a]pyridine (Prep. 17) | 2-Methoxy-5-Pyridineboronic acid | TOF MS ES+ exact mass calculated for $C_{19}H_{16}N_4O$ (p + 1): m/z = 317.1402. Found: 317.1416. | Use 5:1 Toluene:MeOH instead of DME as solvent. Use Na2CO3 instead of NaOH. |
| 11 | 3-Benzo[1,3]diox-olyl-2-(6-methyl-pyridin-2-yl)-pyrazolo[1,5-a]pyridine | 3-Bromo-2-(6-methyl-pyridin-2-yl)-pyrazolo[1,5-a]pyridine (Prep. 17) | 3,4-Methylenedioxybenzene-boronic acid | TOF MS ES+ exact mass calculated for $C_{20}H_{15}N_3O_2$ (p + 1): m/z = 330.1243. Found: 330.1243. | Use 5:1 Toluene:MeOH instead of DME as solvent. Use Na2CO3 instead of NaOH. |
| 12 | 3-(3,5-Difluoro-phenyl)-2-(6-methyl-pyridin-2-yl)-pyrazolo[1,5-a]pyridine | 3-Bromo-2-(6-methyl-pyridin-2-yl)-pyrazolo[1,5-a]pyridine (Prep. 17) | 3,5-Difluorophenylboronic acid | TOF MS ES+ exact mass calculated for $C_{19}H_{13}F_2N_3$ (p + 1): m/z = 322.1156. Found: 322.1147. | Use 5:1 Toluene:MeOH instead of DME as solvent. Use Na2CO3 instead of NaOH. |
| 13 | 2-(6-Methyl-pyridi 2-yl)-3-p-tolyl-pyrazolo[1,5-a]pyridine | 3-Bromo-2-(6-methyl-pyridin-2-yl)-pyrazolo[1,5-a]pyridine (Prep. 17) | p-Tolylbornic acid | TOF MS ES+ exact mass calculated for $C_{20}H_{17}N_3$ (p + 1): m/z = 300.1501. Found: 300.1522 | Use 5:1 Toluene:MeOH instead of DME as solvent. Use Na2CO3 instead of NaOH. |
| 14 | 3-(1H-Indol-5-yl)-2-(6-methyl-pyridin-2-yl)-pyrazolo[1,5-a]pyridine | 3-Bromo-2-(6-methyl-pyridin-2-yl)-pyrazolo[1,5-a]pyridine (Prep. 17) | 5-Indolylboronic acid | TOF MS ES+ exact mass calculated for $C_{21}H_{16}N_4$ (p + 1): m/z = 325.1453. Found: 325.1465 | Use 5:1 Toluene:MeOH instead of DME as solvent. Use Na2CO3 instead of NaOH. |
| 15 | 3-[2-(6-Methyl-pyridin-2-yl)-pyrazolo[1,5-a]pyridin-3-yl]-benzamide | 3-Bromo-2-(6-methyl-pyridin-2-yl)-pyrazolo[1,5-a]pyridine (Prep. 17) | Benzamide-3-boronic acid | MS ES+ m/e 329.1 (M + 1). | Use 5:1 Toluene:MeOH instead of DME as solvent. Use Na2CO3 instead of NaOH. |
| 16 | 3-(3,4-Dimethoxy-phenyl)-2-(6-methyl-pyridin-2-yl)-pyrazolo[1,5-a]pyridine | 3-Bromo-2-(6-methyl-pyridin-2-yl)-pyrazolo[1,5-a]pyridine (Prep. 17) | 3,4-Dimethoxyphenylboron-ic acid | MS ES+ m/e 346.2 (M + 1). | Use 5:1 Toluene:MeOH instead of DME as solvent. Use Na2CO3 |

| EX # | Product (Chemical Name) | Starting Material A | Starting Material B | Physical Data | Comments |
|---|---|---|---|---|---|
| 17 | N,N-Dimethyl-3-[2-(6-methyl-pyridin-2-yl)-pyrazolo[1,5-a]pyridin-3-yl]-benzamide | PREP. 17 | N,N-Dimethylbenzamide-3-boronic acid | MS ES$^+$ m/e 357.2 (M + 1). | instead of NaOH. Use 5:1 Toluene:MeOH instead of DME as solvent. Use Na2CO3 instead of NaOH. |
| 18 | 2-Fluoro-5-[2-(6-methyl-pyridin-2-yl)-pyrazolo[1,5-a]pyridin-3-yl]-benzaldehyde | PREP. 17 | 4-Fluoro-3-formylbenzene boronic acid | TOF MS ES$^+$ exact mass calculated for $C_{12}H_{14}NO$ (p + 1): m/z = 332.1199. Found: 332.1211 | Use 5:1 Toluene:MeOH instead of DME as solvent. Use Na2CO3 instead of NaOH. |
| 19 | 4-[2-(6-Methyl-pyridin-2-yl)-pyrazolo[1,5-a]pyridin-3-yl]-phenylamine | 3-Bromo-2-(6-methyl-pyridin-2-yl)-pyrazolo[1,5-a]pyridine (Prep. 17) | 4-(4,4,5,5-Tetramethyl-1,3,2-dioxaborolan-2-yl) aniline | MS ES$^+$ m/e 301.1 (M + 1). | Use 5:1 Toluene:MeOH instead of DME as solvent. Use Na2CO3 instead of NaOH. |
| 20 | N-{4-[2-(6-Methyl-pyridin-2-yl)-pyrazolo[1,5-a]pyridin-3-yl]-phenyl}-acetamide | 3-Bromo-2-(6-methyl-pyridin-2-yl)-pyrazolo[1,5-a]pyridine (Prep. 17) | 4-(4,4,5,5-Tetramethyl-1,3,2-dioxaborolan-2-yl) acetamide | MS ES$^+$ m/e 343.1 (M + 1). | Use 5:1 Toluene:MeOH instead of DME as solvent. Use Na2CO3 instead of NaOH. |
| 21 | 4-[2-(6-Methyl-pyridin-2-yl)-pyrazolo[1,5-a]pyridin-3-yl]-phenol | 3-Bromo-2-(6-methyl-pyridin-2-yl)-pyrazolo[1,5-a]pyridine (Prep. 17) | 4-(4,4,5,5-Tetramethyl-1,3,2-dioxaborolan-2-yl) phenol | MS ES$^+$ m/e 302.0 (M + 1). | Use 5:1 Toluene:MeOH instead of DME as solvent. Use Na2CO3 instead of NaOH. |
| 22 | 3-(2,3-Dihydro-benzo[1,4]dioxin-6-yl)-2-(6-methyl-pyridin-2-yl)-pyrazolo[1,5-a]pyridine | 3-Bromo-2-(6-methyl-pyridin-2-yl)-pyrazolo[1,5-a]pyridine (Prep. 17) | 1,4-Benzodioxane-6-boronic acid | TOF MS ES$^+$ exact mass calculated for $C_{21}H_{18}N_3O_2$ (p + 1): m/z = 344.1399. Found: 344.1412. | Use 5:1 Toluene:MeOH instead of DME as solvent. Use Na2CO3 instead of NaOH. |
| 23 | 3-(3-Methoxy-phenyl)-2-(6-methyl-pyridin-2-yl)-pyrazolo[1,5-a]pyridine | 3-Bromo-2-(6-methyl-pyridin-2-yl)-pyrazolo[1,5-a]pyridine (Prep. 17) | 3-Methoxyphenyl boronic acid | MS ES$^+$ m/e 316.0 (M + 1). | |
| 24 | 3-(3-Fluoro-phenyl)-2-(6-methyl-pyridin-2-yl)-pyrazolo[1,5-a]pyridine | 3-Bromo-2-(6-methyl-pyridin-2-yl)-pyrazolo[1,5-a]pyridine (Prep. 17) | 3-Fluorophenylboronic acid | MS ES$^+$ m/e 304.0 (M + 1). | |

-continued

| Product EX # (Chemical Name) | Starting Material A | Starting Material B | Physical Data | Comments |
|---|---|---|---|---|
| 25 2-(6-Ethyl-pyridin-2-yl)-3-(4-methoxy-phenyl)-pyrazolo[1,5-a]pyridine | 3-Bromo-2-(6-ethyl-pyridin-2-yl)-pyrazolo[1,5-a]pyridine (Prep. 22) | 4-Methoxyphenylboronic acid | TOF MS ES$^+$ exact mass calculated for $C_{21}H_{19}N_3O$ (p + 1): m/z = 330.1606. Found: 330.1602 | |
| 26 4-[2-(6-Ethyl-pyridin-2-yl)-pyrazolo[1,5-a]pyridin-3-yl]-phenol | (6-ethyl-pyridin-2-yl)-pyrazolo[1,5-a]pyridine (Prep. 22) | 4-(4,4,5,5-Tetramethyl-1,3,2-dioxaborolan-2-yl) phenol | TOF MS ES$^+$ exact mass calculated for $C_{20}H_{17}N_3O$ (p + 1): m/z = 316.1450. Found: 316.1435 | |

EXAMPLE 27

N'-{2-Fluoro-5-[2-(6-methyl-pyridin-2-yl)-pyrazolo[1,5-a]pyridin-3-yl]-benzyl}-N,N-dimethyl-ethane-1,2-diamine

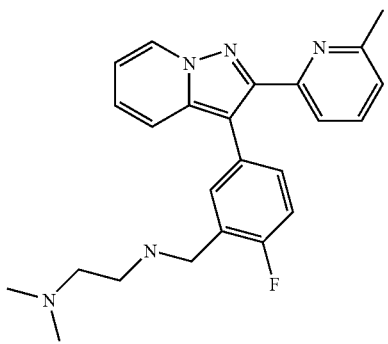

A solution of 2-fluoro-5-[2-(6-methyl-pyridin-2-yl)-pyrazolo[1,5-a]pyridin-3-yl]-benzaldehyde (0.05 g, 0.15 mmol), N,N-dimethyl-ethylenediamine (0.013 g, 0.15 mmol), trimethyl orthoformate (2 mL) in MeOH (5 mL) is stirred for 2 hours at room temperature. The reaction is then treated with sodium borohydride (6.8 mg, 0.18 mmol) and stirred overnight. The reaction is then quenched with 2N NaOH and stirred for 30 minutes. The solution is diluted in $CH_2Cl_2$ and washed with saturated aqueous $NaHCO_3$, brine, and dried over sodium sulfate. The solvent is removed in vacuo to afford 0.06 g (100%) of desired product. MS ES$^+$ m/e 404.1 (M+1).

EXAMPLE 28

4-[2-(6-Chloro-pyridin-2-yl)-pyrazolo[1,5-a]pyridin-3-yl]-quinoline

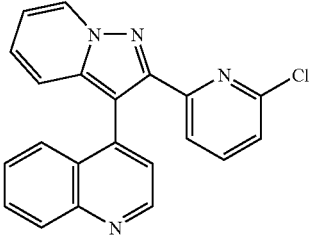

Add 1-aminopyridinium iodide (780 mg, 3.53 mmol), N,N-diisopropylethylamine (0.62 mL, 3.53 mmol), 1-(6-chloro-pyridin-2-yl)-2-quinolin-4-yl-ethanone (500 mg, 1.77 mmol), and ethanol (8 mL) to a sealed tube apparatus. The sealed vessel is heated at 110° C. for 5 hours. After cooling, the crude is concentrated in vacuo. Purification by flash column chromatography (Silica Gel, 25-40% acetone/hexanes) provides the title compound 119 mg (19%) as an orange solid.

MS APCI$^+$ m/e 357 (M+1).

By the method of EXAMPLE 28 the following compounds were prepared:

| EX. # Product Name | Physical Data | Pyridinium Salt |
|---|---|---|
| 29 3-(4-Fluoro-phenyl)-2-pyridin-2-yl-pyrazolo[1,5-a]pyridine | MS ES$^+$ m/e 290 (M + 1). | 1-Amino-pyridinium; iodide |

-continued

| EX. # | Product Name | Physical Data | Pyridinium Salt |
|---|---|---|---|
| 30 | 7-Ethoxy-4-(4-phenyl-2-pyridin-2-yl-pyrazolo[1,5-a]pyridin-3-yl)-quinoline | MS ES$^+$ m/e 443 (M + 1). | 1-Amino-3-phenyl-pyridinium; 2,4,6-trimethyl-benzenesulfonate |
| 31 | 7-Ethoxy-4-(2-pyridin-2-yl-pyrazolo[1,5-a]pyridin-3-yl)-quinoline | MS ES$^+$ m/e 367 (M + 1). | 1-Amino-pyridinium; iodide |
| 32 | 4-[2-(6-Methyl-pyridin-2-yl)-pyrazolo[1,5-a]pyridin-3-yl]-quinoline | TOF MS ES$^+$ exact mass calculated for $C_{22}H_{17}N_4$ (p + 1): m/z = 337.1453. Found: 337. | 1-Amino-pyridinium; iodide |
| 33 | 7-Ethoxy-4-[2-(6-methyl-pyridin-2-yl)-pyrazolo[1,5-a]pyridin-3-yl]-quinoline | TOF MS ES$^+$ exact mass calculated for $C_{24}H_{21}N_4O$ (p + 1): m/z = 381.1715. Found: 381.1722 | 1-Amino-pyridinium; iodide |
| 34 | 4-[2-(6-Ethyl-pyridin-2-yl)-pyrazolo[1,5-a]pyridin-3-yl]-quinoline | TOF MS ES$^+$ exact mass calculated for $C_{23}H_{19}N_4$ (p + 1): m/z = 351.1610. Found: 351.1628 | 1-Amino-pyridinium; iodide |
| 35 | 6,7-Dimethoxy-4-[2-(6-methyl-pyridin-2-yl)-pyrazolo[1,5-a]pyridin-3-yl]-quinoline | TOF MS ES$^+$ exact mass calculated for $C_{24}H_{21}N_4O2$ (p + 1): m/z = 397.1665. Found: 397.1665 | 1-Amino-pyridinium; iodide |
| 36 | 7-Chloro-4-[2-(6-methyl-pyridin-2-yl)-pyrazolo[1,5-a]pyridin-3-yl]-quinoline | MS ES$^+$ m/e 371 (M + 1). | 1-Amino-pyridinium; iodide |
| 37 | 6-Ethoxy-4-[2-(6-methyl-pyridin-2-yl)-pyrazolo[1,5-a]pyridin-3-yl]-quinoline | MS ES$^+$ m/e 381 (M + 1). | 1-Amino-pyridinium; iodide |
| 38 | 3-(4-Fluoro-naphthalen-1-yl)-2-(6-methyl-pyridin-2-yl)-pyrazolo[1,5-a]pyridine | MS ES$^+$ m/e 354 (M + 1). | 1-Amino-pyridinium; iodide |
| 39 | 4-(2-Furan-2-yl-pyrazolo[1,5-a]pyridin-3-yl)-quinoline | TOF MS ES$^+$ exact mass calculated for $C_{20}H_{14}N_3O$ (p + 1): m/z = 312.1137. Found: 312.1126 | 1-Amino-pyridinium; iodide |
| 40 | 4-(2-Thiophen-2-yl-pyrazolo[1,5-a]pyridin-3-yl)-quinoline | TOF MS ES$^+$ exact mass calculated for C20H14N3S $C_{20}H_{14}N_3S$ (p + 1): m/z = 328.0908. Found: 328.0914 | 1-Amino-pyridinium; iodide |
| 41 | 7-Methoxy-4-[2-(6-methyl-pyridin-2-yl)-pyrazolo[1,5-a]pyridin-3-yl]-quinoline | MS ES$^+$ m/e 367 (M + 1). | 1-Amino-pyridinium; iodide |
| 42 | 6,7-Difluoro-4-[2-(6-methyl-pyridin-2-yl)-pyrazolo[1,5-a]pyridin-3-yl]-quinoline | MS ES$^+$ m/e 373 (M + 1). | 1-Amino-pyridinium; iodide |
| 43 | 6,7-Dichloro-4-[2-(6-ethyl-pyridin-2-yl)-pyrazolo[1,5-a]pyridin-3-yl]-quinoline | MS ES$^+$ m/e 419 (M + 1). | 1-Amino-pyridinium; iodide |
| 44 | 4-[2-(6-Ethyl-pyridin-2-yl)-pyrazolo[1,5-a]pyridin-3-yl]-6,7-dimethoxy-quinoline | TOF MS ES$^+$ exact mass calculated for $C_{25}H_{23}N_4O2$ (p + 1): m/z = 411.1821. Found: 411.1828 | 1-Amino-pyridinium; iodide |
| 45 | 6,7-Dichloro-4-[2-(6-methyl-pyridin-2-yl)-pyrazolo[1,5-a]pyridin-3-yl]-quinoline | MS ES$^+$ m/e 405.0 (M + 1). | 1-Amino-pyridinium; iodide |
| 46 | 7-Ethoxy-4-[2-(6-ethyl-pyridin-2-yl)-pyrazolo[1,5-a]pyridin-3-yl]-quinoline | TOF MS ES$^+$ exact mass calculated for $C_{25}H_{23}N_4O$ (p + 1): m/z = 395.1872. Found: 394.1794 | 1-Amino-pyridinium; iodide |
| 47 | 2-(6-Ethyl-pyridin-2-yl)-3-(4-fluoro-naphthalen-1-yl)-pyrazolo[1,5-a]pyridine | TOF MS ES$^+$ exact mass calculated for $C_{24}H_{19}FN_3$ (p + 1): m/z = 368.1563. Found: 368.1569 | 1-Amino-pyridinium; iodide |
| 48 | 3-(4-Fluoro-phenyl)-2-(6-methyl-pyridin-2-yl)- | TOF MS ES$^+$ exact mass calculated for | 1-Amino-3-methoxycarbonyl- |

| EX. # | Product Name | Physical Data | Pyridinium Salt |
|---|---|---|---|
| | pyrazolo[1,5-a]pyridine-6-carboxylic acid ethyl ester | $C_{22}H_{19}FN_3O_2$ (p + 1): m/z = 376.1461. Found: 376.1457 | pyridinium; 2,4,6-trimethyl-benzenesulfonate |
| 49 | 3-(4-Fluoro-phenyl)-2-(6-methyl-pyridin-2-yl)-pyrazolo[1,5-a]pyridine-4-carboxylic acid ethyl ester | TOF MS ES⁺ exact mass calculated for $C_{22}H_{19}FN_3O_2$ (p + 1): m/z = 376.1461. Found: 376.1464 | 1-Amino-3-methoxycarbonyl-pyridinium; 2,4,6-trimethyl-benzenesulfonate |
| 50 | 3-(4-Fluoro-phenyl)-4-iodo-2-(6-methyl-pyridin-2-yl)-pyrazolo[1,5-a]pyridine | TOF MS ES⁺ exact mass calculated for C19H14FIN3 $C_{19}H_{14}FIN_3$ (p + 1): m/z = 430.0216. Found: 430.0241 | 1-Amino-3-iodo-pyridinium; 2,4,6-trimethyl-benzenesulfonate |
| 51 | 3-(4-Fluoro-phenyl)-2-(6-propyl-pyridin-2-yl)-pyrazolo[1,5-a]pyridine | TOF MS ES⁺ exact mass calculated for C21H19FN3 $C_{21}H_{19}FN_3$ (p + 1): m/z = 332.1563. Found: 332.1563 | 1-Amino-pyridinium; iodide |
| 52 | 2-(6-Ethyl-pyridin-2-yl)-3-(4-fluoro-phenyl)-pyrazolo[1,5-a]pyridine | TOF MS ES⁺ exact mass calculated for $C_{20}H_{17}FN_3$ (p + 1): m/z = 318.1406. Found: 318.1404 | 1-Amino-pyridinium; iodide |
| 53 | 3-Pyridin-4-yl-2-pyridin-2-yl-pyrazolo[1,5-a]pyridine | MS ES⁺ m/e 273.3 (M + 1). | 1-Amino-pyridinium; iodide |
| 54 | 4-(2-Pyridin-2-yl-pyrazolo[1,5-a]pyridin-3-yl)-quinoline | MS ES⁺ m/e 323 (M + 1). | 1-aminopyridinium iodide |
| 55 | 4-[2-(6-Fluoro-pyridin-2-yl)-pyrazolo[1,5-a]pyridin-3-yl]-quinoline | MS APCI⁺ m/e 340 (M + 1). | 1-aminopyridinium iodide |
| 56 | 4-[2-(5-Butyl-pyridin-2-yl)-pyrazolo[1,5-a]pyridin-3-yl]-quinoline | MS APCI⁺ m/e 379 (M + 1). | 1-aminopyridinium iodide |
| 57 | 8-Fluoro-4-[2-(6-methyl-pyridin-2-yl)-pyrazolo[1,5-a]pyridin-3-yl]-quinoline | MS APCI⁺ m/e 355 (M + 1). | 1-aminopyridinium iodide |
| 58 | 4-[2-(6-Methyl-pyridin-2-yl)-pyrazolo[1,5-a]pyridin-3-yl]-6-trifluoromethyl-quinoline | MS APCI⁺ m/e 405 (M + 1). | 1-aminopyridinium iodide |
| 59 | 7-Bromo-4-[2-(6-methyl-pyridin-2-yl)-pyrazolo[1,5-a]pyridin-3-yl]-quinoline | MS APCI⁺ m/e 415, 417 (M + 1). | 1-aminopyridinium iodide |
| 60 | 4-[2-(6-Methyl-pyridin-2-yl)-pyrazolo[1,5-a]pyridin-3-yl]-7-trifluoromethyl-quinoline | MS APCI⁺ m/e 405 (M + 1). | 1-aminopyridinium iodide |
| 61 | 3-(3-Chloro-4-fluoro-phenyl)-2-(6-methyl-pyridin-2-yl)-pyrazolo[1,5-a]pyridine | MS APCI⁺ m/e 338 (M + 1). | 1-aminopyridinium iodide |
| 62 | 2-(6-Methyl-pyridin-2-yl)-3-(2,4,5-trifluoro-phenyl)-pyrazolo[1,5-a]pyridine | MS APCI⁺ m/e 340 (M + 1). | 1-aminopyridinium iodide |
| 63 | 3-(4-Fluoro-3-trifluoromethyl-phenyl)-2-(6-methyl-pyridin-2-yl)-pyrazolo[1,5-a]pyridine | MS APCI⁺ m/e 372 (M + 1). | 1-aminopyridinium iodide |
| 64 | 2-(6-Chloro-pyridin-2-yl)-3-(4-fluoro-phenyl)-pyrazolo[1,5-a]pyridine | MS APCI⁺ m/e 324 (M + 1). | 1-aminopyridinium iodide |
| 65 | 4-[2-(5-Bromo-pyridin-2-yl)-pyrazolo[1,5-a]pyridin-3-yl]-quinoline | MS APCI⁺ m/e 401 (M + 1). | 1-aminopyridinium iodide |
| 66 | 4-(5-Benzyl-2-pyridin-2-yl-pyrazolo[1,5-a]pyridin-3-yl)-quinoline | MS APCI⁺ m/e 413 (M + 1). | 4-Benzyl-pyridin-1-yl-ammonium 2,4,6-trimethyl-benzenesulfonate |
| 67 | 4-[5-Benzyl-2-(6-methyl-pyridin-2-yl)-pyrazolo[1,5-a]pyridin-3-yl]-7-bromo-quinoline | MS APCI⁺ m/e 505 (M + 1). | 4-Benzyl-pyridin-1-yl-ammonium 2,4,6-trimethyl-benzenesulfonate |
| 68 | 4-(5-Benzyl-2-pyridin-2-yl-pyrazolo[1,5-a]pyridin-3-yl)-7-bromo-quinoline | MS APCI⁺ m/e 491 (M + 1). | 4-Benzyl-pyridin-1-yl-ammonium 2,4,6-trimethyl-benzenesulfonate |

-continued

| EX. # | Product Name | Physical Data | Pyridinium Salt |
|---|---|---|---|
| 69 | 2-Pyridin-2-yl-3-quinolin-4-yl-pyrazolo[1,5-a]pyridine-5-carboxylic acid ethyl ester | MS APCI$^+$ m/e 395 (M + 1). | 4-Methoxycarbonyl-pyridin-1-yl-ammonium 2,4,6-trimethyl-benzenesulfonate |
| 70 | 2-(Pyridin-2-yl)-3-(quinolin-4-yl)-pyrazolo[1,5-a]pyridine-6-carboxylic acid ethyl ester | MS APCI$^+$ m/e 395 (M + 1). | 3-Ethoxycarbonyl-pyridin-1-yl-ammonium 2,4,6-trimethyl-benzenesulfonate |
| 71 | 7-Methoxy-4-[2-(6-methyl-pyridin-2-yl)-pyrazolo[1,5-a]pyrazol-3-yl]-quinoline | $^1$H NMR(CDCl$_3$) δ 8.87-8.84(m, 1H), 8.69-8.63(m, 1H), 7.58-7.53 (m, 1H), 7.51-7.48(m, 1H), 7.37-7.06(m, 5H), 7.02-6.95(m, 2H), 6.92-6.85(m, 1H), 3.50(s, 3H), 2.44(s, 3H). | 1-aminopyridinium iodide |
| 72 | 7-Methoxy-4-(2-pyridin-2-yl-pyrazolo[1,5-a]pyridin-3-yl)-quinoline | MS APCI$^+$ m/e 353 (M + 1). | 1-aminopyridinium iodide |

EXAMPLE 73

4-[2-(6-Methyl-pyridin-2-yl)-pyrazolo[1,5-a]pyridin-3-yl]-quinoline-7-carboxylic acid methyl ester

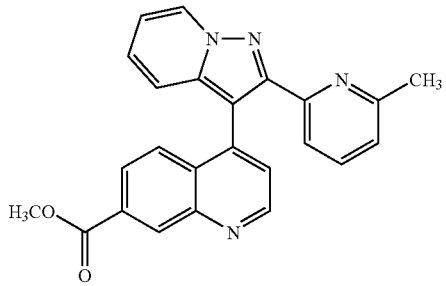

Combine 7-bromo-4-[2-(6-methyl-pyridin-2-yl)-pyrazolo[1,5-a]pyridin-3-yl]-quinoline (0.18 g, 0.43 mmol), triphenylphosphine (36 mg, 0.14 mmol), sodium acetate (0.05 g, 0.61 mmol), methanol (2.7 mL), and DMF (2.7 mL). Bubble nitrogen gas through the solution for 10 minutes. Add palladium acetate (0.03 g, 0.13 mmol). Bubble nitrogen gas through the solution for another 10 minutes. Connect a carbon monoxide balloon to the reaction vessel and heat at 80° C. for 24 hours. Evaporate the solvent in vacuo. Chromatograph the residue on silica gel (elute with 50% ethyl acetate/hexanes then 75% ethyl acetate/hexanes) to afford the title compound 72 mg (42%) as a yellowish solid.

MS APCI$^+$ m/e 395 (M+1).

EXAMPLE 74

4-[2-(6-Methyl-pyridin-2-yl)-pyrazolo[1,5-a]pyridin-3-yl]-quinoline-6-carboxylic acid methyl ester

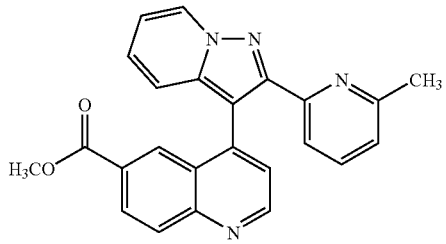

Using a method similar to EXAMPLE 73, using 6-bromo-4-[2-(6-methyl-pyridin-2-yl)-pyrazolo[1,5-a]pyridin-3-yl]-quinoline (0.14 g, 0.35 mmol) affords the title compound 0.11 g (82%) as a yellowish solid.

MS APCI$^+$ m/e 395 (M+1).

EXAMPLE 75

4-(5-Benzyl-2-pyridin-2-yl-pyrazolo[1,5-a]pyridin-3-yl)-quinoline-7-carboxylic acid methyl ester

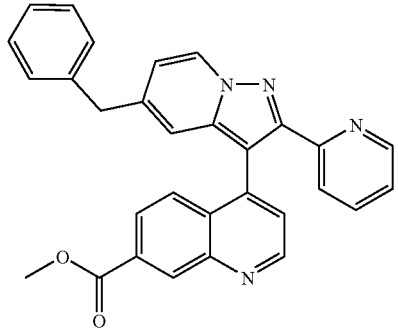

To a solution of 4-(5-benzyl-2-pyridin-2-yl-pyrazolo-[1,5-a]-pyridin-3-yl)-7-bromo-quinoline (118 mg, 0.24 mmol) in DMF (4 mL) and methanol (4 mL), add triphenylphosphine (20 mg, 0.07 mmol) and sodium acetate (28 mg, 0.36 mmol). Bubble nitrogen for 10 minutes. Add palladium acetate (16 mg, 0.07 mmol) and bubble nitrogen for another 10 minutes. Bubble carbon monoxide through the solution for 5 minutes and attach a carbon monoxide balloon. Heat the reaction mixture at 80° C. for 2 days. Cool the reaction mixture to room temperature. Add water (20 mL) and extract the aqueous solution with ethyl acetate (3×20 mL). Dry the combined organic layers with sodium sulfate and concentrate. Purify by flash column chromatography (SiO$_2$, 20-50% ethyl acetate/hexanes) to give the title compound 84 mg (75%) as a yellow solid.

MS APCI$^+$ m/e 471 (M+1). TLC (SiO$_2$): R$_f$ 0.25 (30% ethyl acetate/hexanes)

EXAMPLE 76

3-(4-Fluoro-phenyl)-2-(6-methyl-pyridin-2-yl)-pyrazolo[1,5-a]pyridine-6-carboxylic acid (2-dimethylamino-ethyl)-amide

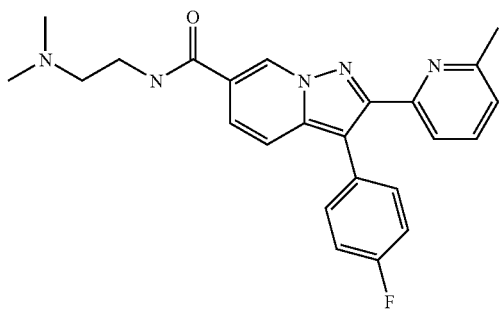

Heat 3-(4-fluoro-phenyl)-2-(6-methyl-pyridin-2-yl)-pyrazolo[1,5-a]pyridine-6-carboxylic acid ethyl ester (75 mg, 0.2 mmol) in 2 ml of N,N-dimethylethylenediamine at 90° C. for 6 hr in a sealed glass tube with stirring. Extract reaction solution once with water/methylene chloride and concentrate the organic layer in vacuo. Purify using preparative TLC (Silica Gel, 90:10 methylene chloride/methanol) to give 12 mg (10%) of the title compound MS ES$^+$ m/e 418.2 (M+1).

By the method of EXAMPLE 76 the following compounds were prepared:

EXAMPLE 81

4-[2-(6-Methoxy-pyridin-2-yl)-pyrazolo[1,5-a]pyridin-3-yl]-quinoline

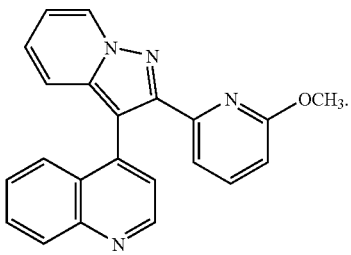

Add methanol (19 mg, 0.59 mmol) and sodium hydride (14 mg, 60% dispersion, 0.35 mmol) to a solution of 4-[2-(6-chloro-pyridin-2-yl)-pyrazolo[1,5-a]pyridin-3-yl]-quinoline (42 mg, 0.118 mmol) in DMF (0.6 mL) at room temperature. Heat to 110° C. for 3 hours, cool to room temperature, and quench with saturated aqueous ammonium chloride (0.5 mL). Concentrate in vacuo, filter, and purify by flash column chromatography (Silica Gel, 20-40% acetone/hexanes) to provide the title compound 30 mg (73%) as a white solid.

MS APCI$^+$ m/e 353 (M+1). TLC (SiO$_2$): R$_f$ 0.20 (1:1 acetone/hexanes)

EXAMPLE 82

4-[2-(6-Ethoxy-pyridin-2-yl)-pyrazolo[1,5-a]pyridin-3-yl]-quinoline

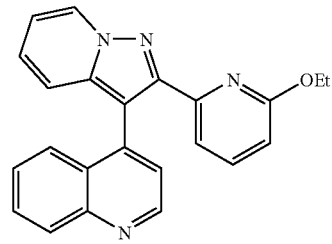

Add sodium hydride (25.5 mg, 0.64 mmol) to a solution of 4-[2-(6-chloro-pyridin-2-yl)-pyrazolo[1,5-a]pyridin-3-

| EX. # | Product Name | Physical Data |
|---|---|---|
| 77 | 4-[2-(6-Methyl-pyridin-2-yl)-pyrazolo[1,5-a]pyridin-3-yl]-quinoline-6-carboxylic acid(2-dimethylamino-ethyl)-amide | MS APCI$^+$ m/e 451 (M + 1). |
| 78 | 4-[2-(6-Methyl-pyridin-2-yl)-pyrazolo[1,5-a]pyridin-3-yl]-quinoline-7-carboxylic acid(2-dimethylamino-ethyl)-amide | MS APCI$^+$ m/e 451 (M + 1). |
| 79 | 5-[2-(6-Methyl-pyridin-2-yl)-pyrazolo[1,5-a]pyridin-3-yl]-benzofuran-2-carboxylic acid(2-dimethyl amino-ethyl)-amide | TOF MS ES$^+$ exact mass calculated for C$_{26}$H$_{26}$N$_5$O$_2$ (p + 1): m/z = 440.2086. Found: 440.2110. |
| 80 | 4-[2-(6-Methyl-pyridin-2-yl)-pyrazolo[1,5-a]pyridin-3-yl]-quinoline-7-carboxylic acid [3-(4-methyl-piperazin-1-yl)-propyl]-amide | MS APCI$^+$ m/e 520 (M + 1). | yl]-quinoline (50 mg, 0.14 mmol) in ethanol (2.5 mL) at 0° C. Stir the reaction mixture at 0° C. for 10 minutes, room temperature for 10 minutes more, and reflux overnight. Cool the reaction mixture to room temperature, quench with saturated aqueous ammonium chloride (3 mL). Add water (20 mL) and extract the aqueous solution with methylene chloride (3×20 mL). Dry the combined organic layers with sodium sulfate and purify by flash column chromatography (SiO$_2$, 50% ethyl acetate/hexanes) to give the title compound 48 mg (94%) as an off-white solid.

MS APCI$^+$ m/e 367 (M+1).

EXAMPLE 83

3-(4-Fluoro-phenyl)-2-(6-methoxy-pyridin-2-yl)-pyrazolo[1,5-a]pyridine

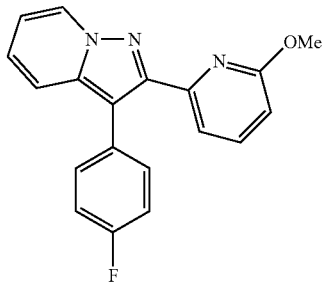

Add sodium hydride (20.7 mg, 60% dispersion in mineral oil, 0.52 mmol) to a solution of 2-(6-chloro-pyridin-2-yl)-3-(4-fluoro-phenyl)-pyrazolo[1,5-a]pyridine (33.5 mg, 0.10 mmol) in DMF (2.5 mL) and methanol (2.5 mL) at room temperature. Stir the reaction mixture at room temperature for 4 hours and at 80° C. for 48 hours. Cool to room temperature and concentrate in vacuo. Add water (20 mL) and extract the aqueous solution with methylene chloride (3×20 mL). Dry the combined organic layers with sodium sulfate and concentrate. Purify by flash column chromatography (SiO$_2$, 50% ethyl acetate/hexanes) to give the title compound 31 mg (97%) as an off-white solid.

MS APCI$^+$ m/e 320 (M+1).

EXAMPLE 84

2-(6-Ethoxy-pyridin-2-yl)-3-(4-fluoro-phenyl)-pyrazolo[1,5-a]pyridine

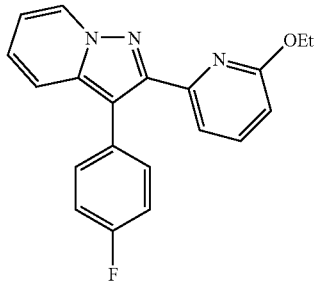

Add sodium hydride (20.7 mg, 0.52 mmol) to a solution of 2-(6-chloro-pyridin-2-yl)-3-(4-fluoro-phenyl)-pyrazolo[1,5-a]pyridine (33.5 mg, 0.10 mmol) in ethanol (2.5 mL) at 0° C. Stir the reaction mixture at 0° C. for 30 minutes and at 80° C. for 48 hours. Cool the reaction mixture to room temperature and concentrate in vacuo Using the same procedure as above afforded the title compound 31 mg (93%) as an off-white solid.

MS APCI$^+$ m/e 334 (M+1).

EXAMPLE 85

7-Benzyl-4-[2-(6-methyl-pyridin-2-yl)-pyrazolo[1,5-a]pyridin-3-yl]-quinoline

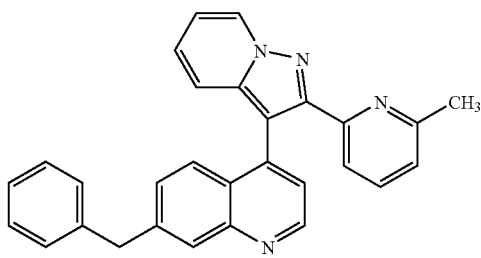

Bubble nitrogen gas through 1 mL of THF for 10 minutes. Add benzyl magnesium chloride (2M in THF, 0.12 mL, 0.24 mmol), zinc chloride (1M in diethyl ether, 0.26 mL, 0.26 mmol). Bubble with nitrogen gas for 15 minutes. Add Pd(PPh$_3$)$_2$Cl$_2$ (4 mg, 0.006 mmol), 7-bromo-4-[2-(6-methyl-pyridin-2-yl)-pyrazolo[1,5-a]pyridin-3-yl]-quinoline (0.05 g, 0.12 mmol). Stir at room temperature for 48 hours. Quench with aqueous saturated NH$_4$Cl solution. Evaporate the solvent in vacuo. Add methylene chloride. Filter the mixture and concentrate the filtrate in vacuo. Chromatograph the residue on silica gel (elute with 50% ethyl acetate/hexanes then 100% ethyl acetate). Final purification by preparative HPLC affords the title compound 20 mg (40%) as a yellow foam.

MS APCI$^+$ m/e 427 (M+1).

EXAMPLE 86

3-{4-[2-(6-Methyl-pyridin-2-yl)-pyrazolo[1,5-a]pyridin-3-yl]-quinolin-7-yl}-acrylic acid methyl ester

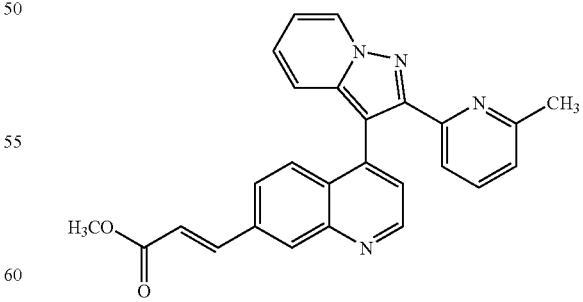

Combine 7-bromo-4-[2-(6-methyl-pyridin-2-yl)-pyrazolo[1,5-a]pyridin-3-yl]-quinoline (0.15 g, 0.36 mmol), tri-o-tolylphosphine (0.38 g, 1.26 mmol), tribuytlamine (0.12 mL, 0.5 mmol), methyl acrylate (0.065 ml, 0.72 mmol), anhydrous toluene (3 mL), and DMF (1.5 mL). Bubble nitrogen gas through the solution for 20 minutes. Add palladium acetate (4.0 mg, 0.018 mmol). Heat the reaction mixture at 80° C. for 48 hours. Chromatograph the residue on silica gel (elute with 2% methanol/methylene chloride, then 4% methanol/methylene chloride). Further purification by preparative HPLC affords the title compound 42 mg (28%) as a yellowish solid.

MS APCI$^+$ m/e 421 (M+1).

EXAMPLE 87

3-{4-[2-(6-Methyl-pyridin-2-yl)-pyrazolo[1,5-a]pyridin-3-yl]-quinolin-7-yl}-acrylic acid

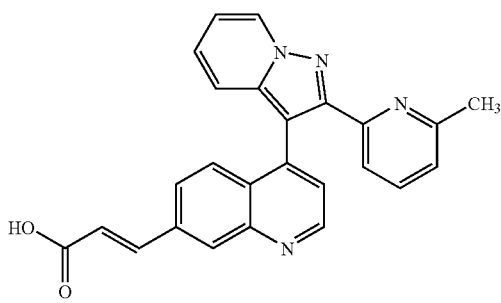

To a solution of 3-{4-[2-(6-methyl-pyridin-2-yl)-pyrazolo[1,5-a]pyridin-3-yl]-quinolin-7-yl}-acrylic methyl ester (0.03 g, 0.07 mmol), THF (1 mL), and H$_2$O (0.5 mL), add LiOH (0.012 g, 0.29 mmol). Stir the reaction mixture at room temperature for 24 hours. Evaporate the solvents in vacuo. Chromatograph the residue on SCX ion-exchange resin (elute with 95% methanol/ethyl acetate, then 100% methanol, then 2M NH$_3$ in methanol) to afford the title compound 26 mg (93%) as a yellowish solid.

MS APCI$^+$ m/e 407 (M+1).

EXAMPLE 88

4-[2-(6-Ethylsulfanyl-pyridin-2-yl)-pyrazolo[1,5-a]-pyridin-3-yl]-quinoline

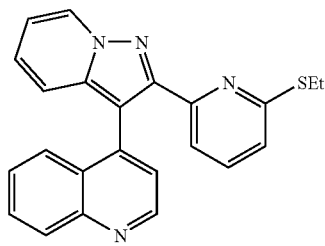

Add ethanethiol (0.71 mL, 0.96 mmol) to a solution of 4-[2-(6-chloro-pyridin-2-yl)-pyrazolo[1,5-a]pyridin-3-yl]-quinoline (37 mg, 0.1 mmol) in DMF (2.5 mL) at 0° C. Add sodium hydride (38 mg, 0.96 mmol), stir the mixture at room temperature for 72 hours. Dilute the reaction mixture with methylene chloride (50 mL) and wash with water (2×50 mL), brine (1×50 mL). Dry the combined organic layers with sodium sulfate and concentrate. Purify the residue by flash column chromatography (SiO$_2$, 50% ethyl acetate/hexanes) to give the title compound 35 mg (91%) as an off-white solid.

MS APCI$^+$ m/e 383 (M+1).

By the method of EXAMPLE 88 the following compounds were prepared:

| EX. # | Product Name | Physical Data |
|---|---|---|
| 89 | 4-[2-(6-Phenylsulfanyl-pyridin-2-yl)-pyrazolo[1,5-a]pyridin-3-yl]-quinoline | MS APCI$^+$ m/e 431 (M + 1). |
| 90 | 4-[2-(6-Morpholin-4-yl-pyridin-2-yl)-pyrazolo[1,5-a]pyridin-3-yl]-quinoline | MS APCI$^+$ m/e 408 (M + 1). |
| 91 | 3-(4-Fluoro-phenyl)-2-(6-methylsulfanyl-pyridin-2-yl)-pyrazolo[1,5-a]pyridine | MS APCI$^+$ m/e 336 (M + 1). |
| 92 | 3-(4-Methylsulfanyl-phenyl)-2-(6-methylsulfanyl-pyridin-2-yl)-pyrazolo[1,5-a]pyridine | MS APCI$^+$ m/e 364 (M + 1). |
| 93 | Dimethyl-(2-{4-[2-(6-methyl-pyridin-2-yl)-pyrazolo[1,5-a]pyridin-3-yl]-quinolin-7-ylsulfanyl}-ethyl)-amine | MS ES$^+$ m/e 440 (M + 1). |

EXAMPLE 94

2-(Pyridin-2-yl)-3-(quinolin-4-yl)-pyrazolo[1,5-a]pyridine-5-carboxylic acid dimethylamide

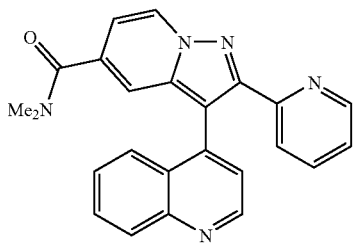

Add trimethylaluminium (0.54 mL, 1.08 mmoL) dropwise to a solution of dimethylamine (0.45 mL, 0.90 mmoL) in methylene chloride (1 mL) at 0° C. Warm to room temperature and stir for 1 hour. Add 2-pyridin-2-yl-3-quinolin-4-yl-pyrazolo[1,5-a]pyridine-5-carboxylic acid ethyl ester (177 mg, 0.45 mmol) in methylene chloride (4 mL), and stir at room temperature for 1 hour and at 80° C. for 24 hours. Cool the reaction mixture to room temperature. Add aqueous solution of potassium sodium tartarate (20 mL) and stir the solution for 1 hour. Separate the organic layers and extract the aqueous solution with methylene chloride (2×20 mL). Dry the combined organic layers with sodium sulfate and concentrate. Purify by flash column chromatography (SiO$_2$, 20-30% methanol/methylene chloride) to give the title compound 54 mg (31%) as a yellow solid.

MS APCI$^+$ m/e 394 (M+1).

EXAMPLE 95

2-(Pyridin-2-yl)-3-(quinolin-4-yl)-pyrazolo[1,5-a]pyridine-6-carboxylic acid dimethylamide

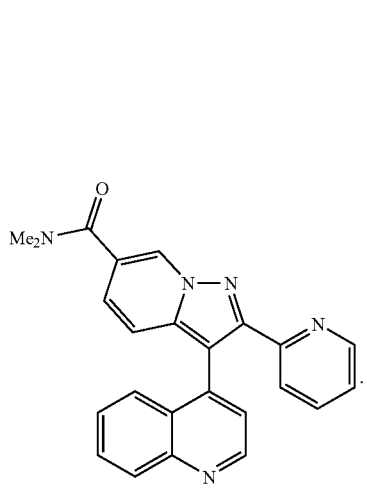

In the same manner as in the previous example 2-pyridin-2-yl-3-quinolin-4-yl-pyrazolo[1,5-a]pyridine-6-carboxylic acid ethyl ester (160 mg, 0.4 mmol) afforded the title compound 21 mg (13%) as a brownish-yellow foam.

MS APCI$^+$ m/e 394 (M+1).

EXAMPLE 96

4-[2-(6-Vinyl-pyridin-2-yl)-pyrazolo[1,5-a]pyridin-3-yl]-quinoline

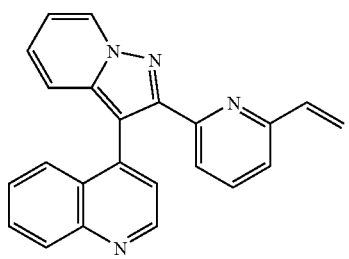

Add tributylvinylstanane (0.056 mL, 0.182 mmol) to a solution of 4-[2-(6-chloro-pyridin-2-yl)-pyrazolo[1,5-a]pyridin-3-yl]-quinoline (59 mg, 0.165 mmol) in toluene (0.83 mL) at room temperature and bubble nitrogen through the solution for 5 minutes. Add tetrakis(triphenylphosphine) palladium (0) (9 mg, 0.008 mmol) and bubble nitrogen through the solution for 1 minute. Heat the reaction to 110° C. for 15 hours. Purify by flash column chromatography (Silica Gel, 20-40% acetone/hexanes) to provide the title compound 11.5 mg (20%) as a white solid.

MS APCI$^+$ m/e 349 (M+1).

EXAMPLE 97

6-[2-(6-Methyl-pyridin-2-yl)-pyrazolo[1,5-a]pyridin-3-yl]-imidazo[1,2-a]pyridin-2-ylamine

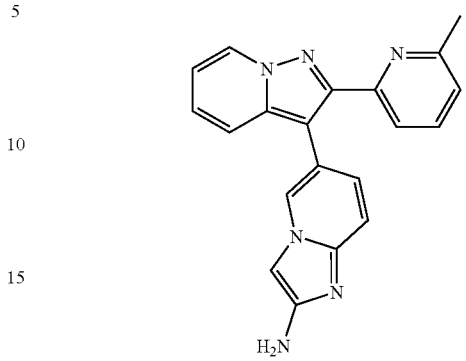

Stir 3-bromo-2-(6-methyl-pyridin-2-yl)-pyrazolo[1,5-a]pyridine (500 mg, 1.74 mmol) in THF (20 ml) at −60° C. and add t-butyl lithium (4 ml, 6.94 mmol, 1.7M in pentane). Stir for 1 hour, then add tri-isopropyl borate (1.2 ml, 5.2 mmol) and warm to 0° C. for 1 hour. Quench with 1M HCl (5 ml). Concentrate in vacuo and redissolve in a 2:1 toluene/methanol mixture (30 ml). Adjust to pH 8 with aqueous 2M Na$_2$CO$_3$. Add 100 mg Pd(PPh$_3$)$_4$ and 2,2,2-trifluoro-N-(6-iodo-imidazo[1,2-a]pyridin-2-yl)-acetamide (200 mg, 563 mmol) and heat to 90° C. for 18 hours. Acidify with 1M HCl and extract with ethyl acetate (3×100 ml). Neutralize aqueous layer with 5N NaOH and extract with ethyl acetate (3×100 ml). Concentrate organic layer in vacuo and purify on Silica gel (eluting with 70/30 Hexane/EtOAc). MS ES$^+$ m/e 341.1 (M+1).

EXAMPLE 98

6-[2-(6-Methyl-pyridin-2-yl)-pyrazolo[1,5-a]pyridin-3-yl]-1H-benzoimidazol-2-ylamine

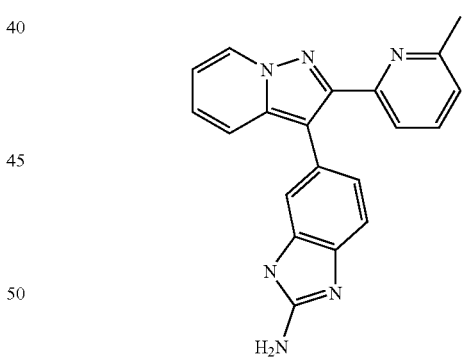

A solution of 2-(6-methyl-pyridin-2-yl)-pyrazolo[1,5-a]pyridine-3-boronic acid (0.5 g, crude) and 6-iodo-1-[(1-methylethyl)sulfonyl-1H-benzimidazol-2-amine (0.2 g, 1.04 mmol) in toluene (20 mL) and MeOH (4 mL) is treated with Na$_2$CO$_3$ (1.0M aqueous, 10 mL) and (PPh$_3$)$_4$Pd (100 mg) and then heated to reflux overnight. The reaction mixture is then cooled, diluted in EtOAc, and the organic phase is washed with water and then brine. The organic solution is dried over MgSO$_4$, filtered, and the solvent removed in vacuo. The residue is purified by silica gel column chromatography to afford 0.026 g of 6-[2-(6-methyl-pyridin-2-yl)-pyrazolo[1,5-a]pyridin-3-yl]-1-propane-2-sulfonyl)-1H-benzimidazol-2-ylamine MS ES$^+$ m/e 447.1 (M+1). This material (13 mg, 0.029 mmol) is desulfonylated by heating in 1:1 acetonitrile: 0.5 NaOH (10 ml) at 60° C. for 30 minutes. Dilution with water and extraction with methylene chloride (3×20 ml), followed by concentration of the organic layer in vacuo. Provides the desired product: MS ES⁺ m/e 341.0 (M+1).

EXAMPLE 99

[3-(4-Fluoro-phenyl)-2-(6-methyl-pyridin-2-yl)-pyrazolo[1,5-a]pyridin-6-yl]-methanol

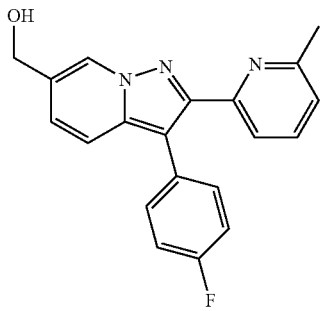

Stir EXAMPLE 49 (150 mg, 0.4 mmol) in ether at room temperature Add lithium aluminum hydride (100 mg) slowly and stir for 1 hour. Quench with EtOAc (10 ml) and filter. Concentrate filtrate in vacuo and purify on silica gel (eluted with 90/10 methylene chloride). MS ES⁺ m/e 334.1 (M+1).

EXAMPLE 100

6-Allyloxymethyl-3-(4-fluoro-phenyl)-2-(6-methyl-pyridin-2-yl)-pyrazolo[1,5-a]pyridine

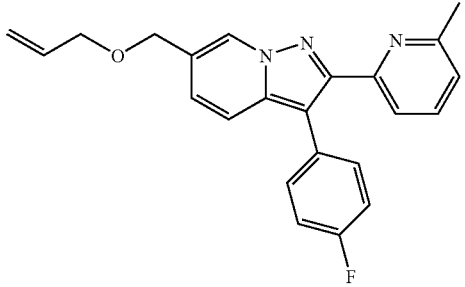

A solution of EXAMPLE 99 (0.13 g, 0.39 mmol) and 1-bromo-3-chloropropane (0.06 g, 0.39 mmol) in DMF (10 mL) was treated with cesium carbonate (0.14 g, 0.43 mmol) and heated to 80° C. The reaction is stirred overnight and is diluted with EtOAc and water. The organic phase is separated and washed with brine. After drying over Na₂SO₄, the organic phase is filtered, and the solvent removed to afford 0.04 g (27%) of product. MS ES⁺ m/e 374.0 (M+1).

EXAMPLE 101

4-[2-(6-Methyl-pyridin-2-yl)-pyrazolo[1,5-a]pyridin-3-yl]-quinoline-7-carboxylic acid (3-pyrrolidin-1-yl-propyl)-amide

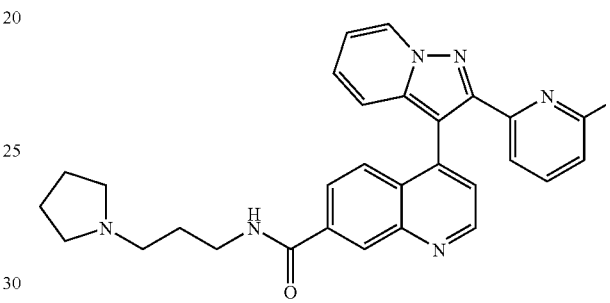

Dissolve EXAMPLE 75 (0.065 g, 0.16 mmol) in 3-pyrrolidin-1-yl-propylamine (8 mL). Heat the solution to 80-100° C. for 48 hours. Concentrate the mixture. Add dichloromethane (25 mL) and water (20 mL) to the residue. Separate the organic layer and wash with water (2×20 mL) and brine (20 mL). Dry the organic layer with sodium sulfate. Filter and concentrate to afford crude product. Chromatograph (SiO₂, 1.5-4% MeOH in CH₂Cl₂) to give the title compound 37 mg (33%) as a pale yellow solid.

TLC: Rf=0.17 (silica gel, 10% CH2Cl2/MeOH) MS ES⁺ m/e 491 (M+1).

By the method of EXAMPLE 101 the following compounds were prepared:

| EXAMPLE # | Product (Chemical Name) | Physical Data |
|---|---|---|
| 102 | 3-{4-[2-(6-Methyl-pyridin-2-yl)-pyrazolo[1,5-a]pyridin-3-yl]-quinolin-7-yl}-propionamide | MS ES⁺ m/e 408 (M + 1). |
| 103 | 3-{4-[2-(6-Methyl-pyridin-2-yl)-pyrazolo[1,5-a]pyridin-3-yl]-quinolin-7-yl}-N-(3-pyrrolidin-1-yl-propyl)-propionamide | MS ES⁺ m/e 479 (M + 1). |
| 104 | N-(2-Dimethylamino-ethyl)-3-{4-[2-(6-methyl-pyridin-2-yl)-pyrazolo[1,5-a]pyridin-3-yl]-quinolin-7-yl}-propionamide | MS ES⁺ m/e 479 (M + 1). |
| 105 | 2-Pyridin-2-yl-3-quinolin-4-yl-pyrazolo[1,5-a]pyridine-5-carboxylic acid (3-dimethylamino-propyl)-amide | MS ES⁺ m/e 450 (M + 1). |
| 106 | 4-[2-(6-Methyl-pyridin-2-yl)-pyrazolo[1,5-a]pyridin-3-yl]-quinoline-7-carboxylic acid (2-hydroxy-ethyl)-amide | |

-continued

| EXAMPLE # | Product (Chemical Name) | Physical Data |
|---|---|---|
| 107 | 4-[2-(6-Methyl-pyridin-2-yl)-pyrazolo[1,5-a]pyridin-3-yl]-quinoline-7-carboxylic acid hydrazide | MS ES+ m/e 395 (M + 1). |
| 108 | 4-[2-(6-Methyl-pyridin-2-yl)-pyrazolo[1,5-a]pyridin-3-yl]-quinoline-7-carboxylic acid (3-hydroxy-propyl)-amide | MS ES+ m/e 438 (M + 1). |
| 109 | 4-[2-(6-Methyl-pyridin-2-yl)-pyrazolo[1,5-a]pyridin-3-yl]-quinoline-7-carboxylic acid methylamide | MS ES+ m/e 394 (M + 1). |
| 110 | 4-[2-(6-Methyl-pyridin-2-yl)-pyrazolo[1,5-a]pyridin-3-yl]-quinoline-7-carboxylic acid (3-ethoxy-propyl)-amide | MS ES+ m/e 466 (M + 1). |
| 111 | 4-[2-(6-Methyl-pyridin-2-yl)-pyrazolo[1,5-a]pyridin-3-yl]-quinoline-7-carboxylic acid (3-morpholin-4-yl-propyl)-amide | MS ES+ m/e 507 (M + 1). |
| 112 | 4-[2-(6-Methyl-pyridin-2-yl)-pyrazolo[1,5-a]pyridin-3-yl]-quinoline-7-carboxylic acid (3-imidazol-1-yl-propyl)-amide | MS ES+ m/e 488 (M + 1). |
| 113 | 4-[2-(6-Methyl-pyridin-2-yl)-pyrazolo[1,5-a]pyridin-3-yl]-quinoline-7-carboxylic acid (3-dimethylamino-propyl)-amide | MS ES+ m/e 465 (M + 1). |
| 114 | 4-[2-(6-Methyl-pyridin-2-yl)-pyrazolo[1,5-a]pyridin-3-yl]-quinoline-7-carboxylic acid [2-(2-methoxy-phenyl)-ethyl]-amide | MS ES+ m/e 514 (M + 1). |
| 115 | 4-[2-(6-Methyl-pyridin-2-yl)-pyrazolo[1,5-a]pyridin-3-yl]-quinoline-7-carboxylic acid (2-morpholin-4-yl-ethyl)-amide | MS ES+ m/e 493 (M + 1). |
| 116 | 4-[2-(6-Methyl-pyridin-2-yl)-pyrazolo[1,5-a]pyridin-3-yl]-quinoline-7-carboxylic acid amide | MS ES+ m/e 380 (M + 1). |

EXAMPLE 117

Dimethyl-(3-{4-[2-(6-methyl-pyridin-2-yl)-pyrazolo[1,5-a]pyridin-3-yl]-quinolin-7-yloxy}-propyl)-amine

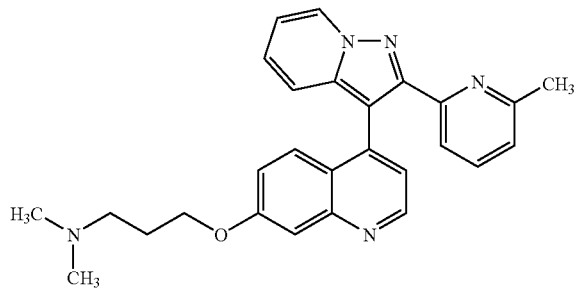

To a solution of 4-[2-(6-methyl-pyridin-2-yl)-pyrazolo[1,5-a]pyridin-3-yl]-quinolin-7-ol (0.1 g, 0.28 mmol) in DMF (7 mL) add 3-dimethylaminopropyl chloride hydrochloride (0.14 g, 0.86 mmol) and cesium carbonate (0.56 g, 1.71 mmol). Stir at room temperature for 48 hour. Evaporate the DMF. Add methylene chloride. Wash with water and then brine. Dry the organic layer over anhydrous Na$_2$SO$_4$, filter the mixture, and concentrate the mixture in vacuo. Chromatograph the residue on silica gel (elute with 100% ethyl acetate, then 1% NH$_4$OH/5% methanol/94% methylene chloride, then 10% methanol in methylene chloride) to give the title compound 63 mg (52%) as an off-white solid.

MS APCI+ m/e 438 (M+1).

By the method of EXAMPLE 117 the following compounds were prepared:

| EXAMPLE # | Product (Chemical Name) | Physical Data |
|---|---|---|
| 118 | 4-[2-(6-Methyl-pyridin-2-yl)-pyrazolo[1,5-a]pyridin-3-yl]-7-(2-morpholin-4-yl-ethoxy)-quinoline | MS APCI+ m/e 466 (M + 1). |
| 119 | Diisopropyl-(2-{4-[2-(6-methyl-pyridin-2-yl)-pyrazolo[1,5-a]pyridin-3-yl]-quinolin-7-yloxy}-ethyl)-amine | MS APCI+ m/e 480 (M + 1). |
| 120 | 4-[2-(6-Methyl-pyridin-2-yl)-pyrazolo[1,5-a]pyridin-3-yl]-7-(2-pyrrol-1-yl-ethoxy)-quinoline | MS APCI+ m/e 446 (M + 1). |

| EXAMPLE # | Product (Chemical Name) | Physical Data |
|---|---|---|
| 121 | Dimethyl-(1-methyl-2-{4-[2-(6-methyl-pyridin-2-yl)-pyrazolo[1,5-a]pyridin-3-yl]-quinolin-7-yloxy}-ethyl)-amine | MS APCI+ m/e 438 (M + 1). |
| 122 | Methyl-(3-{4-[2-(6-methyl-pyridin-2-yl)-pyrazolo[1,5-a]pyridin-3-yl]-quinolin-7-yloxy}-propyl)-amine | MS APCI+ m/e 424 (M + 1). |
| 123 | 4-[2-(6-Methyl-pyridin-2-yl)-pyrazolo[1,5-a]pyridin-3-yl]-7-(2-piperidin-1-yl-ethoxy)-quinoline | MS APCI+ m/e 464 (M + 1). |
| 124 | Diethyl-(2-{4-[2-(6-methyl-pyridin-2-yl)-pyrazolo[1,5-a]pyridin-3-yl]-quinolin-7-yloxy}-ethyl)-amine | MS APCI+ m/e 452 (M + 1). |
| 125 | Dimethyl-{3-[4-(2-pyridin-2-yl-pyrazolo[1,5-a]pyridin-3-yl)-quinolin-7-yloxy]-propyl}-amine | MS APCI+ m/e 424 (M + 1). |
| 126 | 7-(2-Morpholin-4-yl-ethoxy)-4-(2-pyridin-2-yl-pyrazolo[1,5-a]pyridin-3-yl)-quinoline | MS ES+ m/e 452 (M + 1). |
| 127 | Diisopropyl-{2-[4-(2-pyridin-2-yl-pyrazolo[1,5-a]pyridin-3-yl)-quinolin-7-yloxy]-ethyl}-amine | MS ES+ m/e 466 (M + 1). |
| 128 | 4-[2-(6-Methyl-pyridin-2-yl)-pyrazolo[1,5-a]pyridin-3-yl]-7-(3-morpholin-4-yl-propoxy)-quinoline | MS ES+ m/e 480 (M + 1). |
| 129 | 1-(3-{4-[2-(6-Methyl-pyridin-2-yl)-pyrazolo[1,5-a]pyridine-3-yl]-quinolin-7-yloxy}-propyl)-1,3-dihydro-benzoimidazol-2-one | MS APCI+ m/e 527 (M + 1). |

EXAMPLE 130

3-{4-[2-(6-Methyl-pyridin-2-yl)-pyrazolo[1,5-a]pyridin-3-yl]-quinolin-7-yl}-propionic acid methyl ester

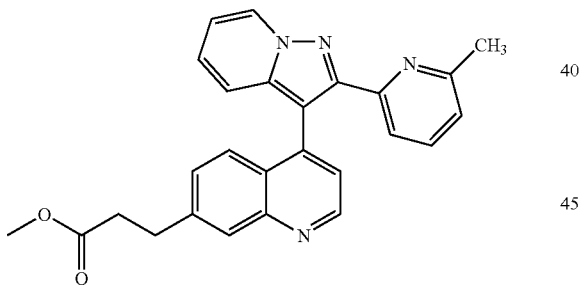

Add Pd/C (10%, 0.46 g) to a solution of 3-{4-[2-(6-methyl-pyridin-2-yl)-pyrazolo[1,5-a]pyridin-3-yl]-quinolin-7-yl}-acrylic acid methyl ester (0.462 g, 1.1 mmol) in MeOH (10 mL) and dichloromethane (10 mL). Bubble nitrogen for 15 minutes. Connect the hydrogen balloon to the reaction flask and stir overnight. Filter through celite and wash the celite pad with dichloromethane (50 mL). Remove the solvent. Chromatograph the residue (elute with 2% MeOH in dichloromethane) to give the desired product as a pale yellow solid 0.27 g (59%).

$^1$H NMR (CDCl$_3$) δ 9.22-9.14 (m, 1H), 8.69-8.61 (m, 1H), 8.37-8.30 (m, 1H), 7.84-7.74 (m, 2H), 7.73-7.65 (m, 1H), 7.63-7.54 (m, 1H), 7.47-7.37 (m, 1H), 7.35-7.29 (m, 2H), 7.08-6.98 (m, 2H), 3.68 (s, 3H), 3.25-3.16 (m, 2H), 2.82-2.71 (m, 2H), 2.03 (s, 3H). TLC: R$_f$=0.4 (silica gel, 10% CH$_2$Cl$_2$/MeOH) MS ES+ m/e 423 (M+1).

EXAMPLE 131

Diethyl-{3-[4-(2-pyridin-2-yl-pyrazolo[1,5-a]pyridin-3-yl)-quinolin-7-yloxy]-propyl}-amine

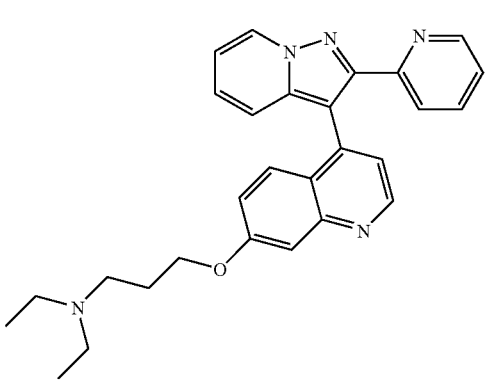

A solution of 7-(3-chloro-propoxy)-4-(2-pyridin-2-yl-pyrazolo[1,5-a]pyridin-3-yl)-quinoline (0.1 g, 0.24 mmol) in DMF was treated with N,N-diethylamine (excess) and KI (catalytic). The reaction was heated to 60° C. in a sealed tube and stirred overnight. The reaction was quenched with water and extracted with CH$_2$Cl$_2$. The organic was dried and the solvent removed. The crude was purified by silica gel column to afford the desired product. MS ES+ m/e 452 (M+1).

By the method of EXAMPLE 131 the following compounds were prepared:

| EX # | Product (Chemical Name) | Starting Material A | Starting Material B | Physical Data | Comments |
|---|---|---|---|---|---|
| 132 | Ethyl-methyl-{3-[4-(2-pyridin-2-yl-pyrazolo[1,5-a]pyridin-3-yl)-quinolin-7-yloxy]-propyl}-amine | 7-(3-Chloro-propoxy)-4-(2-pyridin-2-yl-pyrazolo[1,5-a]pyridin-3-yl)-quinoline | N-Ethyl-N-methylamine | MS ES+ m/e 438.1 (M + 1). | |
| 133 | 4-(2-Pyridin-2-yl-pyrazolo[1,5-a]pyridin-3-yl)-7-(3-pyrrolidin-1-yl-propoxy)-quinoline | 7-(3-Chloro-propoxy)-4-(2-pyridin-2-yl-pyrazolo[1,5-a]pyridin-3-yl)-quinoline | Pyrrolidine | MS ES+ m/e 450.1 (M + 1). | |
| 134 | 7-(3-Piperidin-1-yl-propoxy)-4-(2-pyridin-2-yl-pyrazolo[1,5-a]pyridin-3-yl)-quinoline | 7-(3-Chloro-propoxy)-4-(2-pyridin-2-yl-pyrazolo[1,5-a]pyridin-3-yl)-quinoline | Piperidine | MS ES+ m/e 464.1 (M + 1). | |
| 135 | Diethyl-{2-[4-(2-pyridin-2-yl-pyrazolo[1,5-a]pyridin-3-yl)-quinolin-7-yloxy]-ethyl}-amine | 7-(2-Chloro-ethoxy)-4-(2-pyridin-2-yl-pyrazolo[1,5-a]pyridin-3-yl)-quinoline | N,N-Diethylamine | MS ES+ m/e 438.0 (M + 1). | |
| 136 | Dimethyl-{2-[4-(2-pyridin-2-yl-pyrazolo[1,5-a]pyridin-3-yl)-quinolin-7-yloxy]-ethyl}-amine | 7-(2-Chloro-ethoxy)-4-(2-pyridin-2-yl-pyrazolo[1,5-a]pyridin-3-yl)-quinoline | N,N-Dimethylamine | MS ES+ m/e 410.2 (M + 1). | |

TGF-β RECEPTOR I AND II PURIFICATION AND IN VITRO KINASE REACTIONS

For TGF-β Type I (RIT204D) and Type II (RII WT) Receptor Kinases:

The 6×-HIS tagged cytoplasmic kinase domain of each receptor was expressed and purified from Sf9 insect cell lysates as briefly described below:

Cell pellets after 48-72 hrs of infection were lysed in lysis buffer (LB: 50 mM Tris pH 7.5, 150 mM NaCl, 50 mM NaF, 0.5% NP40 with freshly added 20 mM β-mercaptoethanol, 10 mM imidazole, 1 mM PMSF, 1×EDTA-free Complete Protease Inhibitor (Boehringer Mannheim).

Cell lysates were clarified by centrifugation and 0.45 uM filtered prior to purification by Ni/NTA affinity chromatography (Qiagen).

Chromatography Protocol:

Equilibrate with 10 CV of LB, load sample, wash with 10 CV RIPA buffer (50 mM Tris pH 7.5, 150 mM NaCl, 1% NP40, 1 mM EDTA, 0.25% sodium deoxycholate, added fresh 20 mM β-mercaptoethanol, 1 mM PMSF), wash with 10 CV LB, wash with 10 CV 1× KB (50 mM Tris pH 7.5, 150 mM NaCl, 4 mM MgCl$_2$, 1 mM NaF, 2 mM βmercaptoethanol), elute with a linear gradient of 1× KB containing 200 mM Imidazole.

Both enzymes were approximately 90% pure and had autophosphorylation activity.

Reactions: 170-200 nM enzyme in 1× KB, compound dilution series in 1× KB/16% DMSO (20 uM to 1 mM final concentration with 4% DMSO final concentration), reactions started by adding ATP mix (4 uM ATP/1 uCi $^{33}$P-γ-ATP final concentrations) in 1× KB.

Reactions were incubated at 30° C. for 1 hr RIT204D or 40 min for RII WT. Reactions were stopped and quantitated using standard TCA/BSA precipitation onto Millipore FB glass fiber filter plates and by liquid scintillation counting on a MicroBeta JET.

TGF-β RECEPTOR I

All exemplified compounds were tested essentially as described above and were found to inhibit the TGF-beta Type I Receptor Kinase with an IC50 of at least 10 uM. As representative of the series, Examples 43, 47, 53, and 56, inhibited the TGF-beta Type I kinase with IC50's, of 0.152 uM, 0.175 uM, 0.806 uM, and 0.102 uM, respectively.

TGF-β RECEPTOR II

As above, all exemplified compounds were found to inhibit the TGF-beta Type II Receptor Kinase with an IC50 of at least 20 uM. As representative of the series, Examples 43, 47, 53 and 56 inhibited the TGF-beta Type II kinase with IC50's of 3.17 uM, 5.10 uM, 20 uM, and 0.377 uM, respectively.

p38α IN VITRO KINASE ASSAY

Active p38α/SAPK2α was purchased from Upstate Biotechnology (cat#14-251). A known p38α substrate from EGFR was used in the assay (Young, et al. (1997) JBC 272:12116-12121).

Reactions were performed in 1× kinase buffer (25 mM Tris-HCl pH 7.5, 5 mM β-glycerophosphate, 2 mM DTT, 0.1 mM Na$_3$VO$_4$, 10 mM MgCl$_2$, 1 uM Microcystin) with 5 nM p38α, 62.5 uM substrate, 40 uM to 0.2 nM compound dilution series in 1×KB/16% DMSO (final 4% DMSO concentration). Reactions were started by addition of 100 uM ATP (final concentration) with 1 uCi $^{33}$P-γ-ATP in 1×KB and incubated at 30° C. for 40 min. Reactions were stopped with H$_3$PO$_4$ and quantitated on Millipore PH phosphocellulose filter plates by liquid scintillation counting on a MicroBeta JET.

Representative data for compounds of the current invention with the p38α IC50<20.00 (uM): Examples 45, 46, 78 and 117 gave, respectively, IC$_{50}$'s of 0.390, 0.369, 0.233 and 0.078 uM.

MV1LU p3TP-LUX ASSAY

A stable Mv1Lu clone (C1) containing the p3TP-Lux reporter was created by standard transfection and puromycin selection protocols. This stable clone was used to screen the example compounds for their ability to inhibit TGF-β dependent luciferase production as briefly described below:
1. Plated Mv1Lu C1 cells in Wallac™ Black Isoplates.
2. Allowed cells to adhere overnight.
3. Removed media and replaced with 0.5% FBS DMEM media.
4. Added the compound dilution series in 0.5% FBS/DMEM containing 1% DMSO such that the final compound concentration ranged from 20 uM to 0.1 nM and the final DMSO concentration was 0.2%.
5. Incubated at 37° C./5% CO$_2$ for 2 hrs.
6. Added 0.5% FBS/DMEM as control or TGF-β1 diluted. in 0.5% FBS/DMEM (final concentration of 10 pM) to the −/+TGF-β wells respectively.
7. Incubated for 16-20 hrs. at 37° C./5% CO$_2$.
8. Removed media and rinsed 1× with PBS.
9. Removed PBS and lysed the cells with 1× Passive. Lysis Buffer (Promega) at room temperature.
10. Counted relative luciferase activity on the MicroBeta JET by injecting Luciferase Assay Reagent II (PROMEGA).

The use of the above assay in measuring TGF-β responsive activity is described in Wrana, et al. *Cell* 71: 1003-1014 (1992).

As above, all exemplified compounds were found to inhibit TGF-beta dependent luciferase production with an IC50 of at least 20 uM. As representative of the series, Examples 43, 47, 53 and 56 inhibited luciferase production with IC50's of 0.120 uM, 0.100 uM, 0.487 uM, and 0.135 uM, respectively.

PHARMACEUTICAL COMPOSITIONS

The compositions of the present invention are therapeutically effective TGF-β inhibitors, noted above. The composition may be formulated with common excipients, diluents or carriers, and compressed into tablets, or formulated elixirs or solutions for convenient oral administration or administered by intramuscular intravenous routes. The compounds can be administered transdermally and maybe formulated as sustained relief dosage forms and the like.

The method of treating a human patient according to the present invention includes administration of the TGF-β kinase inhibitors. The TGF-βkinase inhibitors are formulated into formulations which may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to 50 mg in the case of parenteral or inhalation administration, and from about 25 to 500 mg in the case of oral or rectal administration) the compounds. Dosages from about 0.5 to about 300 mg/kg per day, preferably 0.5 to 20 mg/kg, of active ingredient may be administered although it will, of course, readily be understood that the amount of the compound actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations useful for separate administration of the TGF-β inhibitors will normally consist of at least one compound selected from the compounds specified herein mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance. Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, for injection, and for oral ingestion.

We claim:

1. A compound selected from the group consisting of:
   3-(4-Fluoro-phenyl)-2-(6-methyl-pyridin-2-yl)-pyrazolo[1,5-a]pyridine;
   Dimethyl-{4-[2-(6-methyl-pyridin-2-yl)-pyrazolo[1,5-a]pyridin-3-yl]-phenyl}-amine;
   3-(4-Methoxy-phenyl)-2-(6-methyl-pyridin-2-yl)-pyrazolo[1,5-a]pyridine;
   2-(6-Methyl-pyridin-2-yl)-3-phenyl-pyrazolo[1,5-a]pyridine;
   2-(6-Methyl-pyridin-2-yl)-3-pyridin-4-yl-pyrazolo[1,5-a]pyridine;
   3-(4-Fluoro-phenyl)-2-(6-methyl-pyridin-2-yl)-6-phenyl-pyrazolo[1,5-a]pyridine;
   3-(4-Fluoro-phenyl)-6-methanesulfonyl-2-(6-methyl-pyridin-2-yl)-pyrazolo[1,5-a]pyridine;
   2-(6-Methyl-pyridin-2-yl)-3-(4-trifluoromethyl-phenyl)-pyrazolo[1,5-a]pyridine;
   3-(6-Methoxy-pyridin-3-yl)-2-(6-methyl-pyridin-2-yl)-pyrazolo[1,5-a]pyridine;
   3-Benzo[1,3]dioxol-5-yl-2-(6-methyl-pyridin-2-yl)-pyrazolo[1,5-a]pyridine;
   3-(3,5-Difluoro-phenyl)-2-(6-methyl-pyridin-2-yl)-pyrazolo[1,5-a]pyridine;
   2-(6-Methyl-pyridin-2-yl)-3-p-tolyl-pyrazolo[1,5-a]pyridine;
   3-(1H-Indol-5-yl)-2-(6-methyl-pyridin-2-yl)-pyrazolo[1,5-a]pyridine;
   3-[2-(6-Methyl-pyridin-2-yl)-pyrazolo[1,5-a]pyridin-3-yl]-benzamide;
   3-(3,4-Dimethoxy-phenyl)-2-(6-methyl-pyridin-2-yl)-pyrazolo[1,5-a]pyridine;
   N,N-Dimethyl-3-[2-(6-methyl-pyridin-2-yl)-pyrazolo[1,5-a]pyridin-3-yl]-benzamide;
   2-Fluoro-5-[2-(6-methyl-pyridin-2-yl)-pyrazolo[1,5-a]pyridin-3-yl]-benzaldehyde;
   4-[2-(6-Methyl-pyridin-2-yl)-pyrazolo[1,5-a]pyridin-3-yl]-phenylamine;
   N-{4-[2-(6-Methyl-pyridin-2-yl)-pyrazolo[1,5-a]pyridin-3-yl]-phenyl}-acetamide;
   4-[2-(6-Methyl-pyridin-2-yl)-pyrazolo[1,5-a]pyridin-3-yl]-phenol;
   3-(2,3-Dihydro-benzo[1,4]dioxin-6-yl)-2-(6-methyl-pyridin-2-yl)-pyrazolo[1,5-a]pyridine;
   3-(3-Methoxy-phenyl)-2-(6-methyl-pyridin-2-yl)-pyrazolo[1,5-a]pyridine;
   3-(3-Fluoro-phenyl)-2-(6-methyl-pyridin-2-yl)-pyrazolo[1,5-a]pyridine;
   2-(6-Ethyl-pyridin-2-yl)-3-(4-methoxy-phenyl)-pyrazolo[1,5-a]pyridine;
   4-[2-(6-Ethyl-pyridin-2-yl)-pyrazolo[1,5-a]pyridin-3-yl]-phenol;
   N'-{2-Fluoro-5-[2-(6-methyl-pyridin-2-yl)-pyrazolo[1,5-a]pyridin-3-yl]-benzyl}-N,N-dimethyl-ethane-1,2-diamine;
   4-[2-(6-Chloro-pyridin-2-yl)-pyrazolo[1,5-a]pyridin-3-yl]-quinoline;
   3-(4-Fluoro-phenyl)-2-pyridin-2-yl-pyrazolo[1,5-a]pyridine;
   7-Ethoxy-4-(4-phenyl-2-pyridin-2-yl-pyrazolo[1,5-a]pyridin-3-yl)-quinoline;
   7-Ethoxy-4-(2-pyridin-2-yl-pyrazolo[1,5-a]pyridin-3-yl)-quinoline;
   4-[2-(6-Methyl-pyridin-2-yl)-pyrazolo[1,5-a]pyridin-3-yl]-quinoline;
   7-Ethoxy-4-[2-(6-methyl-pyridin-2-yl)-pyrazolo[1,5-a]pyridin-3-yl]-quinoline;
   4-[2-(6-Ethyl-pyridin-2-yl)-pyrazolo[1,5-a]pyridin-3-yl]-quinoline;
   6,7-Dimethoxy-4-[2-(6-methyl-pyridin-2-yl)-pyrazolo[1,5-a]pyridin-3-yl]-quinoline;
   7-Chloro-4-[2-(6-methyl-pyridin-2-yl)-pyrazolo[1,5-a]pyridin-3-yl]-quinoline;
   6-Ethoxy-4-[2-(6-methyl-pyridin-2-yl)-pyrazolo[1,5-a]pyridin-3-yl]-quinoline;
   3-(4-Fluoro-naphthalen-1-yl)-2-(6-methyl-pyridin-2-yl)-pyrazolo[1,5-a]pyridine;
   4-(2-Furan-2-yl-pyrazolo[1,5-a]pyridin-3-yl)-quinoline;
   4-(2-Thiophen-2-yl-pyrazolo[1,5-a]pyridin-3-yl)-quinoline;
   7-Methoxy-4-[2-(6-methyl-pyridin-2-yl)-pyrazolo[1,5-a]pyridin-3-yl]-quinoline;
   6,7-Difluoro-4-[2-(6-methyl-pyridin-2-yl)-pyrazolo[1,5-a]pyridin-3-yl]-quinoline;
   6,7-Dichloro-4-[2-(6-ethyl-pyridin-2-yl)-pyrazolo[1,5-a]pyridin-3-yl]-quinoline;
   4-[2-(6-Ethyl-pyridin-2-yl)-pyrazolo[1,5-a]pyridin-3-yl]-6,7-dimethoxy-quinoline;
   6,7-Dichloro-4-[2-(6-methyl-pyridin-2-yl)-pyrazolo[1,5-a]pyridin-3-yl]-quinoline;
   7-Ethoxy-4-[2-(6-ethyl-pyridin-2-yl)-pyrazolo[1,5-a]pyridin-3-yl]-quinoline;
   2-(6-Ethyl-pyridin-2-yl)-3-(4-fluoro-naphthalen-1-yl)-pyrazolo[1,5-a]pyridine;
   3-(4-Fluoro-phenyl)-2-(6-methyl-pyridin-2-yl)-pyrazolo[1,5-a]pyridine-6-carboxylic acid ethyl ester;
   3-(4-Fluoro-phenyl)-2-(6-methyl-pyridin-2-yl)-pyrazolo[1,5-a]pyridine-4-carboxylic acid ethyl ester;
   3-(4-Fluoro-phenyl)-4-iodo-2-(6-methyl-pyridin-2-yl)-pyrazolo[1,5-a]pyridine;
   3-(4-Fluoro-phenyl)-2-(6-propyl-pyridin-2-yl)-pyrazolo[1,5-a]pyridine;
   2-(6-Ethyl-pyridin-2-yl)-3-(4-fluoro-phenyl)-pyrazolo[1,5-a]pyridine;
   3-Pyridin-4-yl-2-pyridin-2-yl-pyrazolo[1,5-a]pyridine;
   4-(2-Pyridin-2-yl-pyrazolo[1,5-a]pyridin-3-yl)-quinoline;
   4-[2-(6-Fluoro-pyridin-2-yl)-pyrazolo[1,5-a]pyridin-3-yl]-quinoline;

4-[2-(5-Butyl-pyridin-2-yl)-pyrazolo[1,5-a]pyridin-3-yl]-quinoline;
8-Fluoro-4-[2-(6-methyl-pyridin-2-yl)-pyrazolo[1,5-a]pyridin-3-yl]-quinoline;
4-[2-(6-Methyl-pyridin-2-yl)-pyrazolo[1,5-a]pyridin-3-yl]-6-trifluoromethyl-quinoline;
7-Bromo-4-[2-(6-methyl-pyridin-2-yl)-pyrazolo[1,5-a]pyridin-3-yl]-quinoline;
4-[2-(6-Methyl-pyridin-2-yl)-pyrazolo[1,5-a]pyridin-3-yl]-7-trifluoromethyl-quinoline;
3-(3-Chloro-4-fluoro-phenyl)-2-(6-methyl-pyridin-2-yl)-pyrazolo[1,5-a]pyridine;
2-(6-Methyl-pyridin-2-yl)-3-(2,4,5-trifluoro-phenyl)-pyrazolo[1,5-a]pyridine;
3-(4-Fluoro-3-trifluoromethyl-phenyl)-2-(6-methyl-pyridin-2-yl)-pyrazolo[1,5-a]pyridine;
2-(6-Chloro-pyridin-2-yl)-3-(4-fluoro-phenyl)-pyrazolo[1,5-a]pyridine;
4-[2-(5-Bromo-pyridin-2-yl)-pyrazolo[1,5-a]pyridin-3-yl]-quinoline;
4-(5-Benzyl-2-pyridin-2-yl-pyrazolo[1,5-a]pyridin-3-yl)-quinoline;
4-[5-Benzyl-2-(6-methyl-pyridin-2-yl)-pyrazolo[1,5-a]pyridin-3-yl]-7-bromo-quinoline;
4-(5-Benzyl-2-pyridin-2-yl-pyrazolo[1,5-a]pyridin-3-yl)-7-bromo-quinoline;
2-Pyridin-2-yl-3-quinolin-4-yl-pyrazolo[1,5-a]pyridine-5-carboxylic acid ethyl ester;
2-(Pyridin-2-yl)-3-(quinolin-4-yl)-pyrazolo[1,5-a]pyridine-6-carboxylic acid ethyl ester;
7-Methoxy-4-[2-(6-methyl-pyridin-2-yl)-pyrazolo[1,5-a]pyridin-3-yl]-quinoline;
7-Methoxy-4-(2-pyridin-2-yl-pyrazolo[1,5-a]pyridin-3-yl)-quinoline;
4-[2-(6-Methyl-pyridin-2-yl)-pyrazolo[1,5-a]pyridin-3-yl]-quinoline-7-carboxylic acid methyl ester;
4-[2-(6-Methyl-pyridin-2-yl)-pyrazolo[1,5-a]pyridin-3-yl]-quinoline-6-carboxylic acid methyl ester;
4-(5-Benzyl-2-pyridin-2-yl-pyrazolo[1,5-a]pyridin-3-yl)-quinoline-7-carboxylic acid methyl ester;
3-(4-Fluoro-phenyl)-2-(6-methyl-pyridin-2-yl)-pyrazolo[1,5-a]pyridine-6-carboxylic acid (2-dimethylamino-ethyl)-amide;
4-[2-(6-Methyl-pyridin-2-yl)-pyrazolo[1,5-a]pyridin-3-yl]-quinoline-6-carboxylic acid (2-dimethylamino-ethyl)-amide;
4-[2-(6-Methyl-pyridin-2-yl)-pyrazolo[1,5-a]pyridin-3-yl]-quinoline-7-carboxylic acid (2-dimethylamino-ethyl)-amide;
5-[2-(6-Methyl-pyridin-2-yl)-pyrazolo[1,5-a]pyridin-3-yl]-benzofuran-2-carboxylic acid (2-dimethylamino-ethyl)-amide;
4-[2-(6-Methyl-pyridin-2-yl)-pyrazolo[1,5-a]pyridin-3-yl]-quinoline-7-carboxylic acid[3-(4-methyl-piperazin-1-yl)-propyl]-amide;
4-[2-(6-Methoxy-pyridin-2-yl)-pyrazolo[1,5-a]pyridin-3-yl]-quinoline;
4-[2-(6-Ethoxy-pyridin-2-yl)-pyrazolo[1,5-a]pyridin-3-yl]-quinoline;
3-(4-Fluoro-phenyl)-2-(6-methoxy-pyridin-2-yl)-pyrazolo[1,5-a]pyridine;
2-(6-Ethoxy-pyridin-2-yl)-3-(4-fluoro-phenyl)-pyrazolo[1,5-a]pyridine;
7-Benzyl-4-[2-(6-methyl-pyridin-2-yl)-pyrazolo[1,5-a]pyridin-3-yl]-quinoline;
3-{4-[2-(6-Methyl-pyridin-2-yl)-pyrazolo[1,5-a]pyridin-3-yl]-quinolin-7-yl}-acrylic acid methyl ester;
3-{4-[2-(6-Methyl-pyridin-2-yl)-pyrazolo[1,5-a]pyridin-3-yl]-quinolin-7-yl}-acrylic acid;
4-[2-(6-Ethylsulfanyl-pyridin-2-yl)-pyrazolo[1,5-a]-pyridin-3-yl]-quinoline;
4-[2-(6-Phenylsulfanyl-pyridin-2-yl)-pyrazolo[1,5-a]pyridin-3-yl]-quinoline;
4-[2-(6-Morpholin-4-yl-pyridin-2-yl)-pyrazolo[1,5-a]pyridin-3-yl]-quinoline;
3-(4-Fluoro-phenyl)-2-(6-methylsulfanyl-pyridin-2-yl)-pyrazolo[1,5-a]pyridine;
3-(4-Methylsulfanyl-phenyl)-2-(6-methylsulfanyl-pyridin-2-yl)-pyrazolo[1,5-a]pyridine;
Dimethyl-(2-{4-[2-(6-methyl-pyridin-2-yl)-pyrazolo[1,5-a]pyridin-3-yl]-quinolin-7-ylsulfanyl}-ethyl)-amine;
2-(Pyridin-2-yl)-3-(quinolin-4-yl)-pyrazolo[1,5-a]pyridine-5-carboxylic acid dimethylamide;
2-(Pyridin-2-yl)-3-(quinolin-4-yl)-pyrazolo[1,5-a]pyridine-6-carboxylic acid dimethylamide;
4-[2-(6-Vinyl-pyridin-2-yl)-pyrazolo[1,5-a]pyridin-3-yl]-quinoline;
6-[2-(6-Methyl-pyridin-2-yl)-pyrazolo[1,5-a]pyridin-3-yl]-imidazo[1,2-a]pyridin-2-ylamine;
6-[2-(6-Methyl-pyridin-2-yl)-pyrazolo[1,5-a]pyridin-3-yl]-1H-benzoimidazol-2-ylamine;
[3-(4-Fluoro-phenyl)-2-(6-methyl-pyridin-2-yl)-pyrazolo[1,5-a]pyridin-6-yl]-methanol;
6-Allyloxymethyl-3-(4-fluoro-phenyl)-2-(6-methyl-pyridin-2-yl)-pyrazolo[1,5-a]pyridine;
4-[2-(6-Methyl-pyridin-2-yl)-pyrazolo[1,5-a]pyridin-3-yl]-quinoline-7-carboxylic acid (3-pyrrolidin-1-yl-propyl)-amide;
3-{4-[2-(6-Methyl-pyridin-2-yl)-pyrazolo[1,5-a]pyridin-3-yl]-quinolin-7-yl}-propionamide;
3-{4-[2-(6-Methyl-pyridin-2-yl)-pyrazolo[1,5-a]pyridin-3-yl]-quinolin-7-yl}-N-(3-pyrrolidin-1-yl-propyl)-propionamide;
N-(2-Dimethylamino-ethyl)-3-{4-[2-(6-methyl-pyridin-2-yl)-pyrazolo[1,5-a]pyridin-3-yl]-quinolin-7-yl}-propionamide;
2-Pyridin-2-yl-3-quinolin-4-yl-pyrazolo[1,5-a]pyridine-5-carboxylic acid (3-dimethylamino-propyl)-amide;
4-[2-(6-Methyl-pyridin-2-yl)-pyrazolo[1,5-a]pyridin-3-yl]-quinoline-7-carboxylic acid (2-hydroxy-ethyl)-amide;
4-[2-(6-Methyl-pyridin-2-yl)-pyrazolo[1,5-a]pyridin-3-yl]-quinoline-7-carboxylic acid hydrazide;
4-[2-(6-Methyl-pyridin-2-yl)-pyrazolo[1,5-a]pyridin-3-yl]-quinoline-7-carboxylic acid (3-hydroxy-propyl)-amide;
4-[2-(6-Methyl-pyridin-2-yl)-pyrazolo[1,5-a]pyridin-3-yl]-quinoline-7-carboxylic acid methylamide;
4-[2-(6-Methyl-pyridin-2-yl)-pyrazolo[1,5-a]pyridin-3-yl]-quinoline-7-carboxylic acid (3-ethoxy-propyl)-amide;
4-[2-(6-Methyl-pyridin-2-yl)-pyrazolo[1,5-a]pyridin-3-yl]-quinoline-7-carboxylic acid (3-morpholin-4-yl-propyl)-amide;
4-[2-(6-Methyl-pyridin-2-yl)-pyrazolo[1,5-a]pyridin-3-yl]-quinoline-7-carboxylic acid (3-imidazol-1-yl-propyl)-amide;
4-[2-(6-Methyl-pyridin-2-yl)-pyrazolo[1,5-a]pyridin-3-yl]-quinoline-7-carboxylic acid (3-dimethylamino-propyl)-amide;
4-[2-(6-Methyl-pyridin-2-yl)-pyrazolo[1,5-a]pyridin-3-yl]-quinoline-7-carboxylic acid[2-(2-methoxy-phenyl)-ethyl]-amide;

4-[2-(6-Methyl-pyridin-2-yl)-pyrazolo[1,5-a]pyridin-3-yl]-quinoline-7-carboxylic acid (2-morpholin-4-yl-ethyl)-amide;

4-[2-(6-Methyl-pyridin-2-yl)-pyrazolo[1,5-a]pyridin-3-yl]-quinoline-7-carboxylic acid amide;

Dimethyl-(3-{4-[2-(6-methyl-pyridin-2-yl)-pyrazolo[1,5-a]pyridin-3-yl]-quinolin-7-yloxy}-propyl)-amine;

4-[2-(6-Methyl-pyridin-2-yl)-pyrazolo[1,5-a]pyridin-3-yl]-7-(2-morpholin-4-yl-ethoxy)-quinoline;

Diisopropyl-(2-{4-[2-(6-methyl-pyridin-2-yl)-pyrazolo[1,5-a]pyridin-3-yl]-quinolin-7-yloxy}-ethyl)-amine;

4-[2-(6-Methyl-pyridin-2-yl)-pyrazolo[1,5-a]pyridin-3-yl]-7-(2-pyrrol-1-yl-ethoxy)-quinoline;

Dimethyl-(1-methyl-2-{4-[2-(6-methyl-pyridin-2-yl)-pyrazolo[1,5-a]pyridin-3-yl]-quinolin-7-yloxy}-ethyl)-amine;

Methyl-(3-{4-[2-(6-methyl-pyridin-2-yl)-pyrazolo[1,5-a]pyridin-3-yl]-quinolin-7-yloxy}-propyl)-amine;

4-[2-(6-Methyl-pyridin-2-yl)-pyrazolo[1,5-a]pyridin-3-yl]-7-(2-piperidin-1-yl-ethoxy)-quinoline;

Diethyl-(2-{4-[2-(6-methyl-pyridin-2-yl)-pyrazolo[1,5-a]pyridin-3-yl]-quinolin-7-yloxy}-ethyl)-amine;

Dimethyl-{3-[4-(2-pyridin-2-yl-pyrazolo[1,5-a]pyridin-3-yl)-quinolin-7-yloxy]-propyl}-amine;

7-(2-Morpholin-4-yl-ethoxy)-4-(2-pyridin-2-yl-pyrazolo[1,5-a]pyridin-3-yl)-quinoline;

Diisopropyl-{2-[4-(2-pyridin-2-yl-pyrazolo[1,5-a]pyridin-3-yl)-quinolin-7-yloxy]-ethyl}-amine;

4-[2-(6-Methyl-pyridin-2-yl)-pyrazolo[1,5-a]pyridin-3-yl]-7-(3-morpholin-4-yl-propoxy)-quinoline;

1-(3-{4-[2-(6-Methyl-pyridin-2-yl)-pyrazolo[1,5-a]pyridine-3-yl]-quinolin-7-yloxy}-propyl)-1,3-dihydro-benzoimidazol-2-one;

3-{4-[2-(6-Methyl-pyridin-2-yl)-pyrazolo[1,5-a]pyridin-3-yl]-quinolin-7-yl}-propionic acid methyl ester;

Diethyl-{3-[4-(2-pyridin-2-yl-pyrazolo[1,5-a]pyridin-3-yl)-quinolin-7-yloxy]-propyl}-amine;

Ethyl-methyl-{3-[4-(2-pyridin-2-yl-pyrazolo[1,5-a]pyridin-3-yl)-quinolin-7-yloxy]-propyl}-amine;

4-(2-Pyridin-2-yl-pyrazolo[1,5-a]pyridin-3-yl)-7-(3-pyrrolidin-1-yl-propoxy)-quinoline;

7-(3-Piperidin-1-yl-propoxy)-4-(2-pyridin-2-yl-pyrazolo[1,5-a]pyridin-3-yl)-quinoline;

Diethyl-{2-[4-(2-pyridin-2-yl-pyrazolo[1,5-a]pyridin-3-yl)-quinolin-7-yloxy]-ethyl}-amine; and Dimethyl-{2-[4-(2-pyridin-2-yl-pyrazolo[1,5-a]pyridin-3-yl)-quinolin-7-yloxy]-ethyl}-amine;

or a pharmaceutically acceptable salt thereof.

2. A pharmaceutical formulation comprising the compound according to claim 1 in admixture with an acceptable pharmaceutical carrier or excipient.

* * * * *